US008742068B2

(12) United States Patent
van Eden et al.

(10) Patent No.: US 8,742,068 B2
(45) Date of Patent: Jun. 3, 2014

(54) TREATMENT AND PREVENTION OF INFLAMMATORY DISEASES AND AUTOIMMUNE DISEASES

(75) Inventors: Willem van Eden, Bilthoven (NL); Ruurd van der Zee, Utrecht (NL)

(73) Assignee: Universiteit Utrecht Holding B.V., Utrecht (NL)

(*) Notice: Subject to any disclaimer, the term of this patent is extended or adjusted under 35 U.S.C. 154(b) by 755 days.

(21) Appl. No.: 12/667,845

(22) PCT Filed: Jul. 7, 2008

(86) PCT No.: PCT/NL2008/050458
§ 371 (c)(1),
(2), (4) Date: Apr. 19, 2010

(87) PCT Pub. No.: WO2009/008719
PCT Pub. Date: Jan. 15, 2009

(65) Prior Publication Data
US 2010/0329985 A1 Dec. 30, 2010

(30) Foreign Application Priority Data

Jul. 6, 2007 (EP) .................................. 07111898
Oct. 16, 2007 (EP) .................................. 07118588

(51) Int. Cl.
*A61K 31/00* (2006.01)

(52) U.S. Cl.
USPC ........... 530/300; 530/326; 514/1.1; 514/21.4; 514/18.7

(58) Field of Classification Search
USPC ....................................................... 530/300
See application file for complete search history.

(56) References Cited

U.S. PATENT DOCUMENTS

| | | | |
|---|---|---|---|
| 6,007,821 A * | 12/1999 | Srivastava et al. | 424/193.1 |
| 6,358,530 B1 | 3/2002 | Eljamal et al. | |
| 2002/0146426 A1 | 10/2002 | Huang et al. | |
| 2004/0224009 A1 | 11/2004 | Albani | |
| 2006/0039918 A1 | 2/2006 | Albani et al. | |
| 2006/0264609 A1* | 11/2006 | Lehner et al. | 530/350 |
| 2008/0039400 A1 | 2/2008 | Van Eden et al. | |
| 2009/0118173 A1 | 5/2009 | Van Eden et al. | |

FOREIGN PATENT DOCUMENTS

| | | |
|---|---|---|
| WO | WO-91/15219 | 10/1991 |
| WO | WO-91/15219 A1 | 10/1991 |
| WO | WO-95/25744 A1 | 9/1995 |
| WO | WO-99/18801 | 4/1999 |
| WO | WO-99/18801 A1 | 4/1999 |
| WO | WO-01/43691 A2 | 6/2001 |
| WO | WO-01/92523 A2 | 12/2001 |
| WO | WO-02/12286 A2 | 2/2002 |
| WO | WO-02/36611 A2 | 5/2002 |
| WO | WO-03/054011 A2 | 7/2003 |
| WO | WO-03/072598 A2 | 9/2003 |
| WO | WO-03/072598 A2 | 9/2003 |
| WO | WO-03/076944 A1 | 9/2003 |
| WO | WO-03/096967 A2 | 11/2003 |
| WO | WO-03/096967 A2 | 11/2003 |
| WO | WO-2005/022160 A2 | 3/2005 |
| WO | WO-2005/048914 A2 | 6/2005 |
| WO | WO-2007/054658 A1 | 5/2007 |
| WO | WO-2007/054658 A1 | 5/2007 |

OTHER PUBLICATIONS

Salvetti et al., Journal of Neuroimmunology (1996) 65, 143-153.*
Arita, Makoto et al., "Resolvin E1, an Endogenous Lipid Mediator Derived from Omega-3 Eicosapentaenoic Acid, Protects Against 2,4,6-Trinitrobenzene Sulfonic Acid-Induced Colitis," Proc Natl Acad Sci USA, vol. 102, May 25, 2005, pp. 7671-7676.
Atherton, E. et al., "Solid Phase Peptide Synthesis: A Practical Approach," IRL Press, London, 1989.
Ausubel et al., "Current Protocols in Molecular Biology," Current Protocols, USA, vol. 1 and 2, 1994.
Bouma, Gerd et al., "The Immunological and Genetic Basis of Inflammatory Bowel Disease," Nature Reviews Immunology, vol. 3, Jul. 2003, pp. 521-533.
Brintnell, W. et al., "The Influence of MHC Class II Molecules Containing the Rheumatoid Arthritis Shared Epitope on the Immune Response to Aggrecan G1 and Its Peptides," Scandinavian Journal of Immunology, vol. 65, 2007, pp. 444-452.
Brown, T.A., "Molecular Biology LabFax," vols. I and II, Second Edition, Academic Press, 1998, 15 pgs.
Chandran, et al., "Inflammatory Bowel Diseas: Dysfunction of GALT and Gur bacterial Flora (II)," Surgen 1, 2003, pp. 125-136.
Chen, Z. et al., "Humanized Transgenic Mice Expressing HLA DR4-DQ3 Haplotype: Reconstituion of Phenotype and HLA-Restricted T-Cell Responses," Tissue Antigens, vol. 68(3), 2006, pp. 210-219.
Chicz et al., "Specificity and Promiscuity among Naturally Processed Peptides Bound to HLA-DR Alleles," J. Exp. Med., vol. 178, 1993, pp. 27-47.
Cooper, Harry S. et al., "Clinicopathologic Study of Dextran Sulfate Sodium Experimental Murine Colitis," Laboratory Investigation, vol. 69, No. 2, 1993, pp. 238-249.
Crotzer, Victoria L. et al., "Autophagy and Intracellular Surveillance: Modulating MHC Class II Antigen Presentation with Stress," PNAS, vol. 102, pp. 7779-7780.
Dengjel, Jorn et al., "Autophagy Promotes MHC Class II Presentation of Peptides from Intracellular Source Proteins," 2005, PNAS US, vol. 102, pp. 7922-7927.
D'Haens, Gert R., et al., "Early Lesions of Recurrent Crohn's Disease Caused by Infusion of Intestinal Contents in Excluded Ileum," Gastroenterology, vol. 114, 1998, pp. 262-267.
Dongre et al., "In vivo MHC Class II Presentation of Cytosolic Proteins Revealed by Rapid Automated Tandem Mass Spectrometry and Functional Analyses," Eur. J. Immunol., vol. 31, 2001, pp. 1485-1494.

(Continued)

*Primary Examiner* — Karlheinz R Skowronek
*Assistant Examiner* — Catherine Mader
(74) *Attorney, Agent, or Firm* — Gilberto M. Villacorta; Sunit Talapatra; Foley & Lardner LLP

(57) ABSTRACT

The present invention relates to the use of fragments of heat shock proteins for the treatment and/or prevention of autoimmune diseases such as arthritis or inflammatory diseases such as Inflammatory Bowel Diseases. Preferably bacterial and/or mammalian heat shock proteins belonging to the HSP70 families are used.

16 Claims, 15 Drawing Sheets

(56) References Cited

OTHER PUBLICATIONS

Figure 2A:
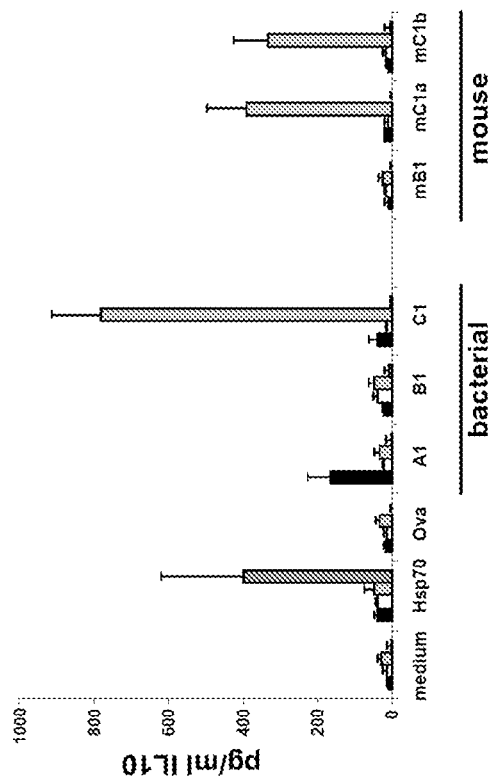

Elsaghier et al., "Disease association of antibodies to human and mycobacterial hsp70 and hsp60 stress proteins," Clin. Exp Immunol., Aug. 1992, pp. 305-309, vol. 89, No. 2, http://www.ncbi.nlm.nih.gov/entrez/query.fcgi?CMD=Display&DB=pubmed , Nov. 23, 2005.

Freed et al., "MHC Class II-Bound Self Peptides from Autoimmune MRL/lpr Mice Reveal Potential T Cell Epitopes for Autoantibody Production in Murine Systemic Lupus Erythematosus," J. Immunol., vol. 164, 2000, pp. 4697-4705.

Friede et al., "Natural Ligand Motifs of Closely Related HLA-DR4 Molecules Predict Features of Rheumatoid Arthritis Associated Peptides," BBA, vol. 1316, 1996, pp. 85-101.

Gaffal, Evelyn et al., "Comparative Evaluation of CD8 + CTL Responses Following Gene Gun Immunization Targeting the Skin with Intracutaneous Injection of Antigen-Transduced Dendritic Cells," European Journal of Cell Biology, vol. 86, 2007, pp. 817-826.

Halder, Thomas et al., "Isolation of Novel HLA-DR Restricted Potential Tumor-Associated Antigens from the Melanoma Cell Line FM3," Cancer Research, vol. 57, Aug. 1, 1997, pp. 3238-3244.

Hanyecz, et al., "Achievement of a Synergistic Adjuvant Effect on Arthritis Induction by Activation of Innate Immunity and Forcing the Immune Response Toward the Th1 Phenotype," Arthritis & Rheumatism, vol. 50, No. 5, 2004, pp. 1665-1676.

Hartmann et al., "Specific Type IV Phosphodiesterase Inhibitor Rolipram Mitigates Experimental Colitis in Mice," JPET, vol. 292, No. 1, 2000, pp. 22-30.

Henikoff et al., "Amino Acid Susbtitution Matrices from Protein Blocks," PNAS, vol. 89, 1992, pp. 10915-10919.

Ho, Steffan N. et al., "Site-Directed Mutagenesis by Overlap Extension Using the Polymerase Chain Reaction," Gene, vol. 77, 1989, pp. 51-59.

Huszti et al., "Low levels of antibodies against E. coli and mycobacterial 65kDa heat shock proteins in patients with inflammatory bowel disease," Inflammation Research, Oct. 2004, pp. 551-555, vol. 53, No. 10, Birkhaeuser Verglag AG, http://www.springerlink.com Nov. 23, 2005.

Jobanputra et al, "The Effectiveness of Infliximab and Etanercept for the Treatment of Rheumatoid Arthritis: A Systematic Review and Economic Evaluation," Health Technology Assessment 2002, vol. 6, No. 21.

Joosten, Irma et al., "Direct Binding of Autoimmune Disease Related T Cell Epitopes to Purified Lewis Rat MHC Class II Molecules," International Immunology, vol. 6, No. 5, 1994, pp. 751-759.

Karlin et al., "Heat shock protein 60 sequence comparisons: Duplications, lateral transfer, and mitochondrial evolution," PNAS, Oct. 10, 2000, pp. 11348-11353, vol. 97, No. 1.

Kingston et al, "A 71-kD Heat Shock Protein (hsp) from *Mycobacterium tuberculosis* has Modulatory Effects on Experimental Rat Arthritis," Clin Exp. Immunol., 1996, vol. 103, pp. 77-82.

Koehm, S. et al., "HLA-DRB1 Alleles Control Allergic Bronchopulmonary Aspergillosis-Like Pulmonary Responses in Humanized Transgenic Mice," J. Allergy Clin Immunol., 2007, vol. 120, No. 3, pp. 570-577.

Langer, Robert, "New Methods of Drug Delivery," Science, vol. 249, Sep. 28, 1990, pp. 1527-1533.

Lippolis et al., "Analysis of MHC Class II Antigen Processing by Quantitation of Peptides that Constitute Nested Sets," J. Imm., vol. 169, 2002, pp. 5089-5097.

Mangalam, Ashutosh et al., "Role of MHC Class II Expressing CD4+ T Cells in Proteolipid Protein$_{91-110}$-Induced EAE in HLA-DR3 Transgenic Mice," Eur. J. Immunol., vol. 36, 2006, pp. 3356-3370.

Marrack et al., "Comparison of Peptides Bound to Spleen and Thymus Class II," J. Exp. Med., vol. 178, 1993, pp. 2173-2183.

Merrifield, R.B., "Solid Phase Peptide Synthesis. I. The Synthesis of a Tetrapeptide," J. Am. Chem. Soc., vol. 85, 1963, pp. 2149-2156.

Mittelman, Abraham et al., "Degenerate Binding of Tyrosinase Peptides to MHC II Ad/Ed Molecules," Journal of Experimental Therapeutics and Oncology, vol. 6, 2007, pp. 231-239.

Mizushima, Noboru et al., "In Vivo Analysis of Autophagy in Response to Nutrient Starvation Using Transgenic Mice Expressing a Fluorescent Autophagosome Marker," Molecular Biology of the Cell, vol. 15, Mar. 2004, pp. 1101-1111.

Muntasell et al., "Dissection of the HLA-DR4 Peptide Repertoire in Endocrine Epithelial Cells: Strong Influence of Invariant Chain and HLA-DM Expression on the Nature of Ligands," J. Immunol., vol. 173, 2004, pp. 1085-1093.

Nelson, et al., "Identification of the Naturally Processed Form of Hen Egg White Lysozyme Bound to the Murine Major Histocompatibility Complex Class II Molecule I-A$^K$," PNAS, vol. 89, 1992, pp. 7380-7383.

Newcomb et al., "Characterization of Endogenous Peptides Bound to Purified HLA-DR Molecules and Their Absence from Invariant Chain-Associated α β Dimers," J. Imm., vol. 150, No. 2, 1993, pp. 499-507.

Paludan, Casper et al., "Endogenous MHC Class II Processing of a Viral Nuclear Antigen After Autophagy," Science 307, 2005, pp. 593-595.

Pizarro, Theresa T. et al., "Mouse Models for the Study of Crohn's Disease," Trends in Molecular Medicine, vol. 9, No. 5, May 2003, pp. 218-222.

Pokorny, C.S. et al. "Association Between Ulverative Colitis and Multiple Sclerosis," Int. Med. Journ., 2007, vol. 37, pp. 721-724.

Reizis et al., "The Peptide Binding Specificity of the MHC Class II I-A Molecule of the Lewis Rat, RT1.B," Intern. Immunol., vol. 8, No. 12, 1996, pp. 1825-1832.

Remington: The Science and Practice of Pharmacy, Lippincott Williams & Wilkins, 21st Rev Ed, 2005.

Remington's Pharmaceutical Sciences, Mack Publishing Company, Philidelphia, Pa., 18th ed. 1990.

Rutgeerts, et al., "Effect of Faecal Stream Diversion on Recurrence of Crohn's Disease in the Neoterminal Ileum," The Lancet, vol. 338, Sep. 28, 1991, pp. 771-774.

Sambrook et al., "Molecular Cloning: A Laboratory Manual", Second Edition, 1989, Cold Spring Harbor Laboratory Press, NY.

Sambrook et al., "Molecular Cloning: A Laboratory Manual", Third Edition, 2001, Cold Spring Harbor Laboratory Press, NY.

Sanjeevi et al., "Molecular Modeling of Eluted Peptides from DQ6 Molecules (DQB1*602 and DQB1*0604) Negatively and Positively Associated with Type 1 Diabetes," Ann. N.Y. Acad. Sci., vol. 958, 2002, pp. 317-320.

Sharif et al., "Characterization of Naturally Processed and Presented Peptides Associated with Bovine Major Histocompatibility Complex (BoLA) Class II DR Molecules," Anim. Genet., vol. 34, 2003, pp. 116-123.

Steinhoff et al., "Autoimmune Intestinal Pathology Induced by hsp60-Specific CD8 T Cells," Immunity, vol. 11, 1999, pp. 349-358.

Strober, et al., "The Immunology of Mucosal Models of Inflammation," Annu. Rev. Immunol., vol. 20, 2002, pp. 495-549.

Suri et al., "Natural Peptides Selected by Diabetogenic DQ8 and Murine I-A$^{g7}$ Molecules Show Common Sequence Specificity," J. Clin. Invest., vol. 115, No. 8, 2005, pp. 2268-2276 (Suppl. Tables 1 and 2, pp. 38-60).

Tanaka et al., "Activation of T Cells Recognizing an Epitope of Heat-Shock Protein 70 Can Protect Against Rat Adjuvant Arthritis," The Journal of Immunology, 1999, vol. 163, pp. 5560-5565.

te Velde, Anje A. et al., "Critical Appraisal of the Current Practice in Murine TNBS-Induced Colitis," Inflamm Bowel Dis., vol. 12, No. 10, Oct. 2006, pp. 995-999.

van Drunen Littel-van 'den Hurk, et al., "Needle-Free Delivery of Veterinary DNA Vaccines," Methods in Molecular Medicine, vol. 127, 2006, pp. 91-105.

van Eden, W. et al., "Arthritis Protective Regulatory Potential of Self-Heat Shock Protein Cross-Reactive T Cells," Cell Stress & Charperones, 2000, vol. 5, No. 5, pp. 452-457.

Verdu, et al., "Oral Administration of Antigens from Intestinal Flora Anaerobic Bacteria Reduces the Severity of Experimental Acute Colitis in BALB/c Mice," Clin Exp Immunol, vol. 120, 2000, pp. 46-50.

Verreck et al., "Natural Peptides Isolated from Gly$^{86}$/Val$^{86}$-Containing Variants of HLA-DR1,-DR11,-DR13, and -DR52," Immunogenetics, vol. 43, 1996, pp. 392-397.

(56) References Cited

OTHER PUBLICATIONS

White, Thomas J. et al., "The Polymerase Chain Reaction," Trends in Genet., vol. 5, No. 6, 1989, pp. 185-189.
Wooley, Paul, "Animal Models of Rheumatoid Arthritis," Current Opinion in Rheumatology, 1991, vol. 3, pp. 407-420.
Berlo S. E. et al, "HSP70-specific Immune Responses are Anti-Inflammatory and Inhibit Arthritis" Annals of the Rheumatic Diseases, vol. 65, no. Suppl. 2, Jul. 2006, pp. 125-126.
Berlo S. E. et al "Hsp70 Immunization Inhibits Proteoglycan-Induced Arthritis in BALB/c Mice" Immunobiology, vol. 209, No. 4-6, 2004, p. 303.
Hickman-Miller et al., "The Immune Response Under Stress: the Role of HSP-derived Peptides" 2004, Trends in Immunology, vol. 25: 427-433.
Huang, et al. "In Vivo Cytotoxic T Lymphocyte Elicitation by Mycobacterial Heat Shock Protein 70 Fusion Proteins Maps to a Discrete Domain and Is CD4 T Cell Independent" J. Exp. Med, 2000, vol. 191, No. 2, pp. 403-408.
International Search Report (PCT/NL2008/050458) dated Sep. 29, 2009.
Janeway and Travers, 1997, Immunobiology, p. 4:7-4:8.
Tokuyama, et al. "The Simultaneous Blockade of Chemokine Receptors CCR2, CCR5 and CXCR3 by a Non-Peptide Chemokine Receptor Antagonist Protects Mice from Dextran Sodium Sulfate-Mediated Colitis" International Immunology, 2005, vol. 17, No. 8, pp. 1023-1034.
Van Eden et al. "Heat-Shock Proteins Induce T-Cell Regulation of Chronic Inflammation" Nature Reivews. Immunology, Apr. 2005, vol. 5, No. 4, pp. 318-330.
Wendling U. et al. "A Conserved Mycobaterial Heat Shock Protein (hsp) 70 Sequence Prevents Adjuvant Arthritis upon Nasal Administration and Induces IL-10-Producing T Cells That Cross-React with the Mammalian Self-hsp70 Homologue" Journal of Immunology, Mar. 1, 2000, pp. 2711-2717.
Whittall et al. "Interaction Between the CCR5 Chemokine Receptors and Microbial HSP70" Eur. J. Immunol., 2006, vol. 36, pp. 2304-2314.
Yagita et al., "Mouse Colitis Induced by *Escherichia coli* Producing *Yersinia enterocolitica* 60-Kilodalton Heat-Shock Protein" 1999, Digestive Diseases & Sci. vol. 44: No. 2, pp. 445-451.
Yung et al, "Heat Shock Proteins (HSP) for Immunotherapy of Rheumatoid Arthritis (RA)" 2003, Inflamm. Res. vol. 52: 443-451.
NCBI Reference Sequence GenBank access No. NP_214864; molecular chaperone DnaK [*Mycobacterium tuberculosis* H37Rv] (2 pages).
Database UniProt [Online] UniProt; May 1, 1997, "70-kDa heat shock protein—unidentified soil organism", Database accession No. P97965, 2 pgs.
Database UniProt [Online] UniProt; May 2, 2006, "Heat shock protein 9B—*Ictalurus punctatus* (Channel catfish)", Database accession No. Q1WCE7, 2 pgs.
Examination Report mailed May 7, 2012 in corresponding European Appln. No. 08766879.
Berlo, S.E. et al., "Hsp70-Specific Immune Responses are Anti-Inflammatory and Inhibit Arthritis," Ann. Rheum. Dis., Jul. 22, 2006, vol. 65, Suppl. II, p. 125.
Berlo, S.E., et al. HSP 70 immunization inhibits proteoglycan-induced arthritis in BALB/c mice, Immunobiology, 2004, vol. 209, p. 303.
Schwarzenberg et al., "Type 1 Diabetes and Celiac Disease: Overview and Medical Nutrition Therapy," 2005, Diab. Spect. vol. 15; 197-201.
Translation of Office Action mailed Jun. 11, 2013 in Japan Application No. 2010-515990, 7 pgs.
UniprotKB accession P32723, 2004, pp. 1-2.
US Office Action in U.S. Appl. No. 11/774,405 mailed Jun. 4, 2013.
Wendling et al. "A Conserved Mycobaterial Heat Shock Protein (Hsp) 70 Sequence Prevents Adjuvant Arthritis upon Nasal Administration and Induces IL-10-Producing T Cells That Cross-React with the Mammalian Self-hsp70 Homologue," Journal of Immunology, Mar. 1, 2000, vol. 164, No. 5, p. 2711-2717.

\* cited by examiner

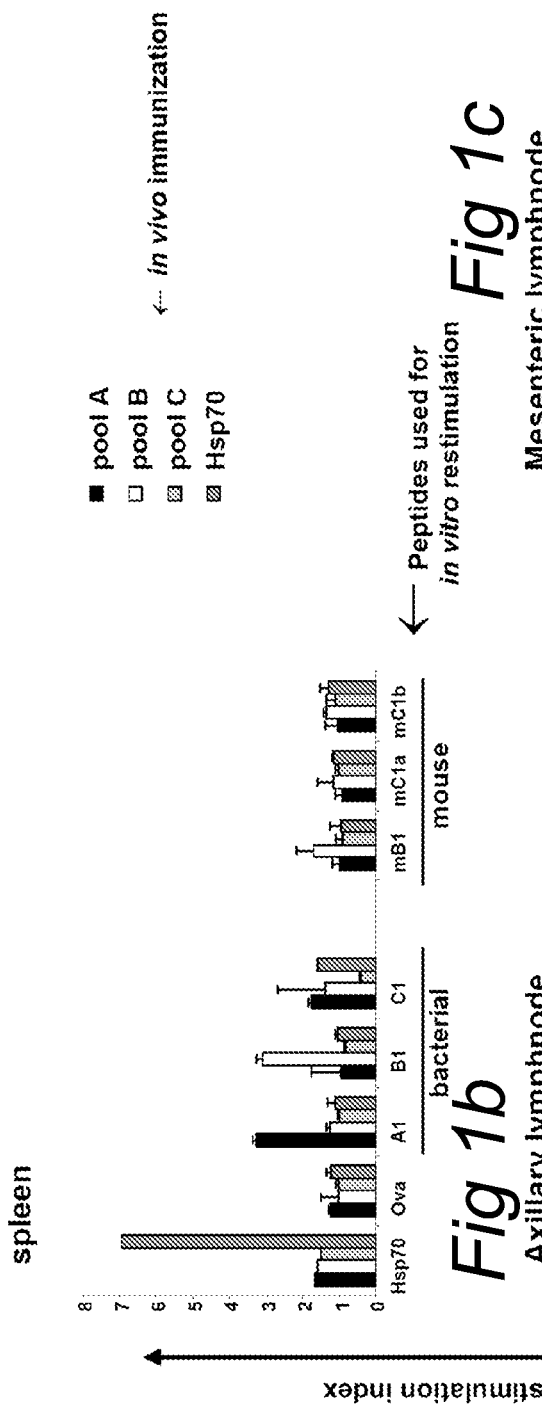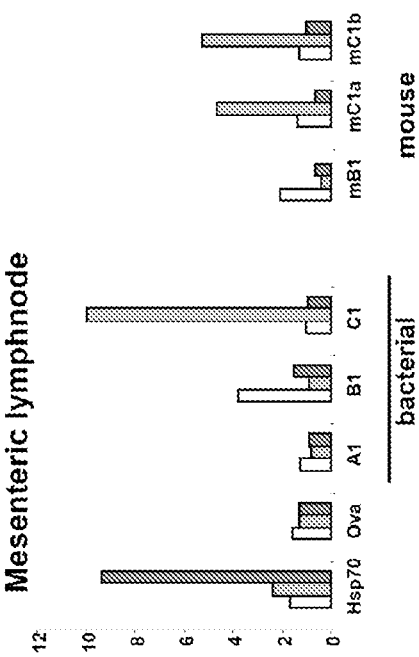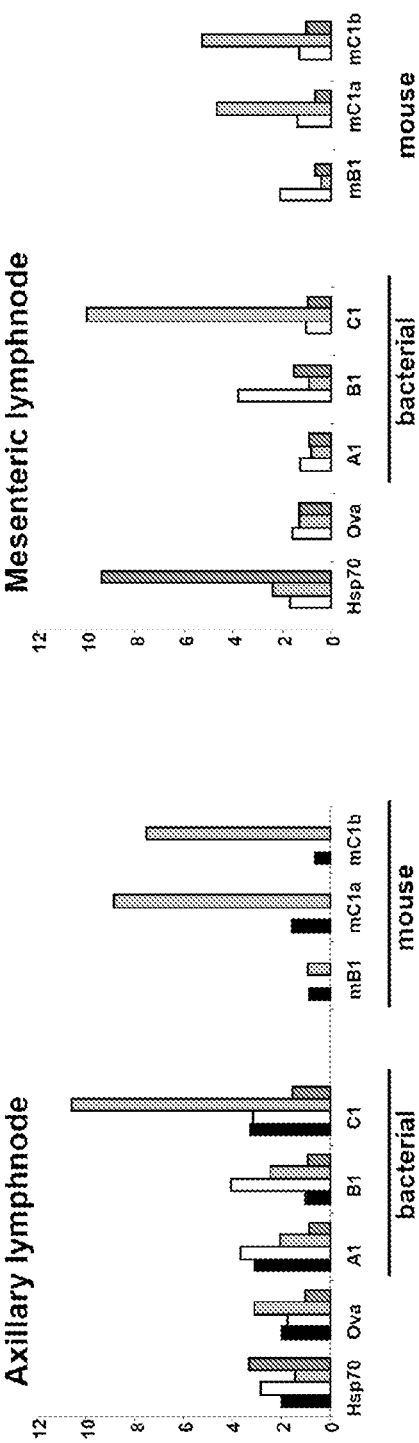

T-cell proliferation

IFN-gamma production

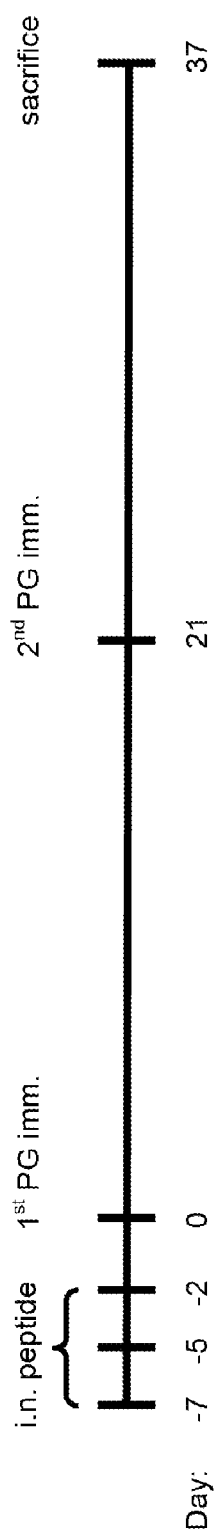
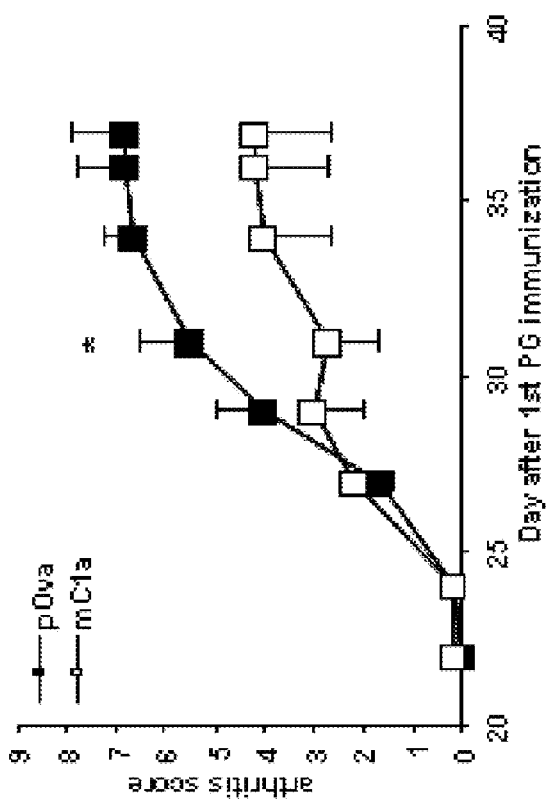
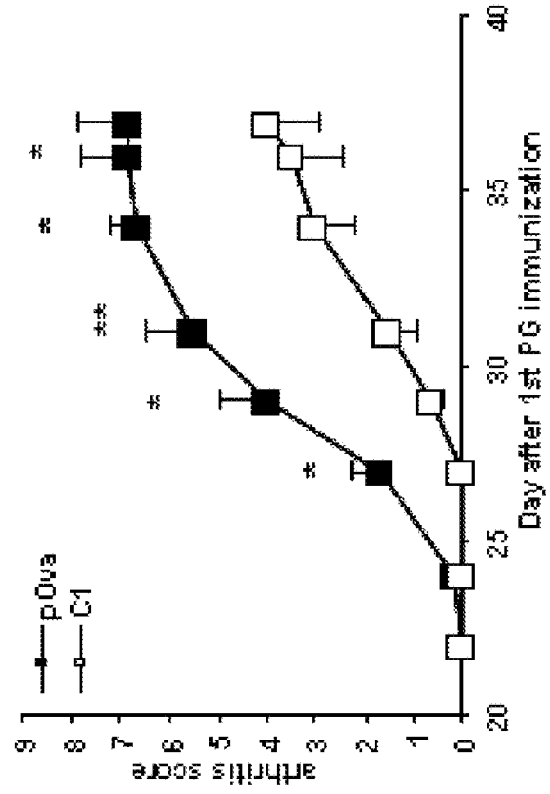

SEQUENCE LISTING

<160> NUMBER OF SEQ ID NOS: 132

<210> SEQ ID NO 1
<211> LENGTH: 15
<212> TYPE: PRT
<213> ORGANISM: Mycobacterium tuberculosis

<400> SEQUENCE: 1

Asp Glu Val Val Ala Val Gly Ala Ala Leu Gln Ala Gly Val Leu
1               5                   10                  15

<210> SEQ ID NO 2
<211> LENGTH: 15
<212> TYPE: PRT
<213> ORGANISM: Mus musculus

<400> SEQUENCE: 2

Asp Glu Ala Val Ala Ile Gly Ala Ala Ile Gln Gly Gly Val Leu
1               5                   10                  15

<210> SEQ ID NO 3
<211> LENGTH: 15
<212> TYPE: PRT

<213> ORGANISM: Mycobacterium tuberculosis

<400> SEQUENCE: 3

Val Leu Arg Ile Val Asn Glu Pro Thr Ala Ala Ala Leu Ala Tyr
1 5 10 15

<210> SEQ ID NO 4
<211> LENGTH: 15
<212> TYPE: PRT
<213> ORGANISM: Mus musculus

<400> SEQUENCE: 4

Val Leu Arg Val Ile Asn Glu Pro Thr Ala Ala Ala Leu Ala Tyr
1 5 10 15

<210> SEQ ID NO 5
<211> LENGTH: 15
<212> TYPE: PRT
<213> ORGANISM: Mus musculus

<400> SEQUENCE: 5

Val Leu Arg Ile Ile Asn Glu Pro Thr Ala Ala Ala Ile Ala Tyr
1 5 10 15

<210> SEQ ID NO 6
<211> LENGTH: 15
<212> TYPE: PRT
<213> ORGANISM: Mycobacterium tuberculosis

<400> SEQUENCE: 6

Lys Pro Phe Gln Ser Val Ile Ala Asp Thr Gly Ile Ser Val Ser
1 5 10 15

<210> SEQ ID NO 7
<211> LENGTH: 15
<212> TYPE: PRT
<213> ORGANISM: Mycobacterium tuberculosis

<400> SEQUENCE: 7

Tyr Thr Ala Pro Glu Ile Ser Ala Arg Ile Leu Met Lys Leu Lys
1 5 10 15

<210> SEQ ID NO 8
<211> LENGTH: 15
<212> TYPE: PRT
<213> ORGANISM: Mycobacterium tuberculosis

<400> SEQUENCE: 8

Ala Glu Gly Gly Ser Lys Val Pro Glu Asp Thr Leu Asn Lys Val
1 5 10 15

<210> SEQ ID NO 9
<211> LENGTH: 15
<212> TYPE: PRT
<213> ORGANISM: Mycobacterium tuberculosis

<400> SEQUENCE: 9

Ala Gln Ala Ala Ser Gln Ala Thr Gly Ala Ala His Pro Gly Gly
1 5 10 15

<210> SEQ ID NO 10
<211> LENGTH: 15
<212> TYPE: PRT
<213> ORGANISM: Mycobacterium tuberculosis

<400> SEQUENCE: 10

```
Glu Gly Ser Arg Thr Thr Pro Ser Ile Val Ala Phe Ala Arg Asn
1               5                   10                  15

<210> SEQ ID NO 11
<211> LENGTH: 15
<212> TYPE: PRT
<213> ORGANISM: Mycobacterium tuberculosis

<400> SEQUENCE: 11

Met Gln Arg Leu Arg Glu Ala Ala Glu Lys Ala Lys Ile Glu Leu
1               5                   10                  15

<210> SEQ ID NO 12
<211> LENGTH: 15
<212> TYPE: PRT
<213> ORGANISM: Mycobacterium tuberculosis

<400> SEQUENCE: 12

Gly Gly Lys Glu Pro Asn Lys Gly Val Asn Pro Asp Glu Val Val
1               5                   10                  15

<210> SEQ ID NO 13
<211> LENGTH: 15
<212> TYPE: PRT
<213> ORGANISM: Mycobacterium tuberculosis

<400> SEQUENCE: 13

Leu Asp Val Thr Pro Leu Ser Leu Gly Ile Glu Thr Lys Gly Gly
1               5                   10                  15

<210> SEQ ID NO 14
<211> LENGTH: 15
<212> TYPE: PRT
<213> ORGANISM: Mycobacterium tuberculosis

<400> SEQUENCE: 14

Ile Leu Val Phe Asp Leu Gly Gly Gly Thr Phe Asp Val Ser Leu
1               5                   10                  15

<210> SEQ ID NO 15
<211> LENGTH: 15
<212> TYPE: PRT
<213> ORGANISM: Mycobacterium tuberculosis

<400> SEQUENCE: 15

Arg Gly Ile Pro Gln Ile Glu Val Thr Phe Asp Ile Asp Ala Asn
1               5                   10                  15

<210> SEQ ID NO 16
<211> LENGTH: 15
<212> TYPE: PRT
<213> ORGANISM: Mycobacterium tuberculosis

<400> SEQUENCE: 16

Gln Ile Glu Val Thr Phe Asp Ile Asp Ala Asn Gly Ile Val His
1               5                   10                  15

<210> SEQ ID NO 17
<211> LENGTH: 14
<212> TYPE: PRT
<213> ORGANISM: Mus musculus

<400> SEQUENCE: 17

Ile Ile Ala Asn Asp Gln Gly Asn Arg Thr Thr Pro Ser Tyr
1               5                   10
```

```
<210> SEQ ID NO 18
<211> LENGTH: 15
<212> TYPE: PRT
<213> ORGANISM: Mus musculus

<400> SEQUENCE: 18

Ile Thr Pro Ser Tyr Val Ala Phe Thr Pro Glu Gly Glu Arg Leu
1               5                   10                  15

<210> SEQ ID NO 19
<211> LENGTH: 15
<212> TYPE: PRT
<213> ORGANISM: Homo sapiens

<400> SEQUENCE: 19

Thr Pro Ser Tyr Val Ala Phe Thr Asp Thr Glu Arg Leu Ile Gly
1               5                   10                  15

<210> SEQ ID NO 20
<211> LENGTH: 17
<212> TYPE: PRT
<213> ORGANISM: Homo sapiens

<400> SEQUENCE: 20

Thr Pro Ser Tyr Val Ala Phe Thr Asp Thr Glu Arg Leu Ile Gly Asp
1               5                   10                  15

Ala

<210> SEQ ID NO 21
<211> LENGTH: 13
<212> TYPE: PRT
<213> ORGANISM: Mus musculus

<400> SEQUENCE: 21

Asp Ala Ala Lys Asn Gln Leu Thr Ser Asn Pro Glu Asn
1               5                   10

<210> SEQ ID NO 22
<211> LENGTH: 18
<212> TYPE: PRT
<213> ORGANISM: Homo sapiens

<400> SEQUENCE: 22

Asn Pro Thr Asn Thr Val Phe Asp Ala Lys Arg Leu Ile Gly Arg Arg
1               5                   10                  15

Phe Asp

<210> SEQ ID NO 23
<211> LENGTH: 18
<212> TYPE: PRT
<213> ORGANISM: Mus musculus

<400> SEQUENCE: 23

Gln Asp Ile Lys Phe Leu Pro Phe Lys Val Val Glu Lys Lys Thr Lys
1               5                   10                  15

Pro Tyr

<210> SEQ ID NO 24
<211> LENGTH: 18
<212> TYPE: PRT
<213> ORGANISM: Rattus norvegicus

<400> SEQUENCE: 24
```

Leu Asn Val Leu Arg Ile Ile Asn Glu Pro Thr Ala Ala Ala Ile Ala
1               5                   10                  15

Tyr Gly

<210> SEQ ID NO 25
<211> LENGTH: 17
<212> TYPE: PRT
<213> ORGANISM: Rattus norvegicus

<400> SEQUENCE: 25

Asn Val Leu Arg Ile Ile Asn Glu Pro Thr Ala Ala Ala Ile Ala Tyr
1               5                   10                  15

Gly

<210> SEQ ID NO 26
<211> LENGTH: 17
<212> TYPE: PRT
<213> ORGANISM: Homo sapiens

<400> SEQUENCE: 26

Asn Val Leu Arg Ile Ile Asn Glu Pro Thr Ala Ala Ala Ile Ala Tyr
1               5                   10                  15

Gly

<210> SEQ ID NO 27
<211> LENGTH: 15
<212> TYPE: PRT
<213> ORGANISM: Homo sapiens

<400> SEQUENCE: 27

Asn Val Leu Arg Ile Ile Asn Glu Pro Thr Ala Ala Ala Ile Ala
1               5                   10                  15

<210> SEQ ID NO 28
<211> LENGTH: 17
<212> TYPE: PRT
<213> ORGANISM: Homo sapiens

<400> SEQUENCE: 28

Asn Val Met Arg Ile Ile Asn Glu Pro Thr Ala Ala Ala Ile Ala Tyr
1               5                   10                  15

Gly

<210> SEQ ID NO 29
<211> LENGTH: 16
<212> TYPE: PRT
<213> ORGANISM: Homo sapiens

<400> SEQUENCE: 29

Val Met Arg Ile Ile Asn Glu Pro Thr Ala Ala Ala Ile Ala Tyr Gly
1               5                   10                  15

<210> SEQ ID NO 30
<211> LENGTH: 15
<212> TYPE: PRT
<213> ORGANISM: Homo sapiens

<400> SEQUENCE: 30

Ile Ile Asn Glu Pro Thr Ala Ala Ala Ile Ala Tyr Gly Leu Asp
1               5                   10                  15

<210> SEQ ID NO 31

```
<211> LENGTH: 14
<212> TYPE: PRT
<213> ORGANISM: Mus musculus

<400> SEQUENCE: 31

Asn Arg Met Val Asn His Phe Ile Ala Glu Phe Lys Arg Lys
1               5                   10

<210> SEQ ID NO 32
<211> LENGTH: 14
<212> TYPE: PRT
<213> ORGANISM: Mus musculus

<400> SEQUENCE: 32

Arg Met Val Asn His Phe Ile Ala Glu Phe Lys Arg Lys His
1               5                   10

<210> SEQ ID NO 33
<211> LENGTH: 15
<212> TYPE: PRT
<213> ORGANISM: Homo sapiens

<400> SEQUENCE: 33

Val Asn His Phe Ile Ala Glu Phe Lys Arg Lys His Lys Lys Asp
1               5                   10                  15

<210> SEQ ID NO 34
<211> LENGTH: 14
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 34

Xaa Asp Phe Tyr Thr Ser Ile Thr Arg Ala Xaa Phe Glu Glu
1               5                   10

<210> SEQ ID NO 35
<211> LENGTH: 17
<212> TYPE: PRT
<213> ORGANISM: Mus musculus

<400> SEQUENCE: 35

Glu Gly Glu Asp Phe Ser Glu Thr Leu Thr Arg Ala Lys Phe Glu Glu
1               5                   10                  15

Leu

<210> SEQ ID NO 36
<211> LENGTH: 13
<212> TYPE: PRT
<213> ORGANISM: Homo sapiens

<400> SEQUENCE: 36

Ala Asp Leu Phe Arg Gly Thr Leu Asp Pro Val Glu Lys
1               5                   10

<210> SEQ ID NO 37
<211> LENGTH: 18
<212> TYPE: PRT
<213> ORGANISM: Rattus rattus
```

```
<400> SEQUENCE: 37

Thr Ile Pro Thr Lys Gln Thr Gln Thr Phe Thr Thr Tyr Ser Asp Asn
1               5                   10                  15

Gln Pro

<210> SEQ ID NO 38
<211> LENGTH: 20
<212> TYPE: PRT
<213> ORGANISM: Homo sapiens

<400> SEQUENCE: 38

Val Pro Thr Lys Lys Ser Gln Ile Phe Ser Thr Ala Ser Asp Asn Gln
1               5                   10                  15

Pro Thr Val Thr
            20

<210> SEQ ID NO 39
<211> LENGTH: 13
<212> TYPE: PRT
<213> ORGANISM: Homo sapiens

<400> SEQUENCE: 39

Gly Glu Arg Ala Met Thr Lys Asp Asn Asn Leu Leu Gly
1               5                   10

<210> SEQ ID NO 40
<211> LENGTH: 16
<212> TYPE: PRT
<213> ORGANISM: Homo sapiens

<400> SEQUENCE: 40

Gly Glu Arg Ala Met Thr Lys Asp Asn Asn Leu Leu Gly Lys Phe Glu
1               5                   10                  15

<210> SEQ ID NO 41
<211> LENGTH: 16
<212> TYPE: PRT
<213> ORGANISM: Homo sapiens

<400> SEQUENCE: 41

Gly Glu Arg Ala Met Thr Lys Asp Asn Asn Leu Leu Gly Arg Phe Glu
1               5                   10                  15

<210> SEQ ID NO 42
<211> LENGTH: 17
<212> TYPE: PRT
<213> ORGANISM: Homo sapiens

<400> SEQUENCE: 42

Ala Asn Gly Ile Leu Asn Val Ser Ala Val Asp Lys Ser Thr Gly Lys
1               5                   10                  15

Glu

<210> SEQ ID NO 43
<211> LENGTH: 14
<212> TYPE: PRT
<213> ORGANISM: Homo sapiens

<400> SEQUENCE: 43

Gly Ile Leu Asn Val Ser Ala Val Asp Lys Ser Thr Gly Lys
1               5                   10

<210> SEQ ID NO 44
```

```
<211> LENGTH: 15
<212> TYPE: PRT
<213> ORGANISM: Homo sapiens

<400> SEQUENCE: 44

Gly Ile Leu Asn Val Ser Ala Val Asp Lys Ser Thr Gly Lys Glu
1               5                   10                  15

<210> SEQ ID NO 45
<211> LENGTH: 12
<212> TYPE: PRT
<213> ORGANISM: Homo sapiens

<400> SEQUENCE: 45

Cys Asn Glu Ile Ile Asn Trp Leu Asp Lys Asn Gln
1               5                   10

<210> SEQ ID NO 46
<211> LENGTH: 16
<212> TYPE: PRT
<213> ORGANISM: Mus musculus

<400> SEQUENCE: 46

Ile Ser Trp Leu Asp Lys Asn Gln Thr Ala Glu Lys Glu Glu Phe Glu
1               5                   10                  15

<210> SEQ ID NO 47
<211> LENGTH: 20
<212> TYPE: PRT
<213> ORGANISM: Mus musculus

<400> SEQUENCE: 47

Tyr Gly Ser Gly Gly Pro Pro Thr Gly Glu Glu Asp Thr Ser Glu
1               5                   10                  15

Lys Asp Glu Leu
            20

<210> SEQ ID NO 48
<211> LENGTH: 641
<212> TYPE: PRT
<213> ORGANISM: Homo sapiens

<400> SEQUENCE: 48

Met Ala Lys Ala Ala Ala Ile Gly Ile Asp Leu Gly Thr Thr Tyr Ser
1               5                   10                  15

Cys Val Gly Val Phe Gln His Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140
```

```
Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ile Ala Tyr Gly Leu Asp Arg Thr Gly Lys Gly Glu
        180                 185                 190

Arg Asn Val Leu Ile Phe Asp Leu Gly Gly Gly Thr Phe Asp Val Ser
            195                 200                 205

Ile Leu Thr Ile Asp Asp Gly Ile Phe Glu Val Lys Ala Thr Ala Gly
        210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
                260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
                340                 345                 350

Phe Phe Asn Gly Arg Asp Leu Asn Lys Ser Ile Asn Pro Asp Glu Ala
            355                 360                 365

Val Ala Tyr Gly Ala Ala Val Gln Ala Ile Leu Met Gly Asp Lys
        370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
                420                 425                 430

Asp Asn Gln Pro Gly Val Leu Ile Gln Val Tyr Glu Gly Glu Arg Ala
            435                 440                 445

Met Thr Lys Asp Asn Asn Leu Leu Gly Arg Phe Glu Leu Ser Gly Ile
        450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
                500                 505                 510

Glu Glu Ile Glu Arg Met Val Gln Glu Ala Lys Tyr Lys Ala Glu
        515                 520                 525

Asp Glu Val Gln Arg Glu Arg Val Ser Ala Lys Asn Ala Leu Glu Ser
530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575
```

-continued

Val Ile Ser Trp Leu Asp Ala Asn Thr Leu Ala Glu Lys Asp Glu Phe
                580                 585                 590

Glu His Lys Arg Lys Glu Leu Glu Gln Val Cys Asn Pro Ile Ile Ser
            595                 600                 605

Gly Leu Tyr Gln Gly Ala Gly Pro Gly Pro Gly Phe Gly Ala
        610                 615                 620

Gln Gly Pro Lys Gly Gly Ser Gly Ser Gly Pro Thr Ile Glu Glu Val
625                 630                 635                 640

Asp

<210> SEQ ID NO 49
<211> LENGTH: 641
<212> TYPE: PRT
<213> ORGANISM: Homo sapiens

<400> SEQUENCE: 49

Met Ala Thr Ala Lys Gly Ile Ala Ile Gly Ile Asp Leu Gly Thr Thr
1               5                   10                  15

Tyr Ser Cys Val Gly Val Phe Gln His Gly Lys Val Glu Ile Ile Ala
                20                  25                  30

Asn Asp Gln Gly Asn Arg Thr Thr Pro Ser Tyr Val Ala Phe Thr Asp
            35                  40                  45

Thr Glu Arg Leu Ile Gly Asp Ala Ala Lys Asn Gln Val Ala Met Asn
50                  55                  60

Pro Gln Asn Thr Val Phe Asp Ala Lys Arg Leu Ile Gly Arg Lys Phe
65                  70                  75                  80

Asn Asp Pro Val Val Gln Ala Asp Met Lys Leu Trp Pro Phe Gln Val
                85                  90                  95

Ile Asn Glu Gly Gly Lys Pro Lys Val Leu Val Ser Tyr Lys Gly Glu
            100                 105                 110

Asn Lys Ala Phe Tyr Pro Glu Glu Ile Ser Ser Met Val Leu Thr Lys
        115                 120                 125

Leu Lys Glu Thr Ala Glu Ala Phe Leu Gly His Pro Val Thr Asn Ala
130                 135                 140

Val Ile Thr Val Pro Ala Tyr Phe Asn Asp Ser Gln Arg Gln Ala Thr
145                 150                 155                 160

Lys Asp Ala Gly Val Ile Ala Gly Leu Asn Val Leu Arg Ile Ile Asn
                165                 170                 175

Glu Pro Thr Ala Ala Ala Ile Ala Tyr Gly Leu Asp Lys Gly Gly Gln
            180                 185                 190

Gly Glu Arg His Val Leu Ile Phe Asp Leu Gly Gly Gly Thr Phe Asp
        195                 200                 205

Val Ser Ile Leu Thr Ile Asp Asp Gly Ile Phe Glu Val Lys Ala Thr
210                 215                 220

Ala Gly Asp Thr His Leu Gly Gly Glu Asp Phe Asp Asn Arg Leu Val
225                 230                 235                 240

Ser His Phe Val Glu Glu Phe Lys Arg Lys His Lys Lys Asp Ile Ser
                245                 250                 255

Gln Asn Lys Arg Ala Val Arg Arg Leu Arg Thr Ala Cys Glu Arg Ala
            260                 265                 270

Lys Arg Thr Leu Ser Ser Ser Thr Gln Ala Asn Leu Glu Ile Asp Ser
        275                 280                 285

Leu Tyr Glu Gly Ile Asp Phe Tyr Thr Ser Ile Thr Arg Ala Arg Phe
290                 295                 300

Glu Glu Leu Cys Ala Asp Leu Phe Arg Gly Thr Leu Glu Pro Val Glu
305                 310                 315                 320

Lys Ala Leu Arg Asp Ala Lys Met Asp Lys Ala Lys Ile His Asp Ile
                325                 330                 335

Val Leu Val Gly Gly Ser Thr Arg Ile Pro Lys Val Gln Arg Leu Leu
            340                 345                 350

Gln Asp Tyr Phe Asn Gly Arg Asp Leu Asn Lys Ser Ile Asn Pro Asp
        355                 360                 365

Glu Ala Val Ala Tyr Gly Ala Ala Val Gln Ala Ala Ile Leu Met Gly
    370                 375                 380

Asp Lys Ser Glu Lys Val Gln Asp Leu Leu Leu Leu Asp Val Ala Pro
385                 390                 395                 400

Leu Ser Leu Gly Leu Glu Thr Ala Gly Gly Val Met Thr Ala Leu Ile
                405                 410                 415

Lys Arg Asn Ser Thr Ile Pro Thr Lys Gln Thr Gln Ile Phe Thr Thr
                420                 425                 430

Tyr Ser Asp Asn Gln Pro Gly Val Leu Ile Gln Val Tyr Glu Gly Glu
        435                 440                 445

Arg Ala Met Thr Lys Asp Asn Asn Leu Leu Gly Arg Phe Asp Leu Thr
450                 455                 460

Gly Ile Pro Pro Ala Pro Arg Gly Val Pro Gln Ile Glu Val Thr Phe
465                 470                 475                 480

Asp Ile Asp Ala Asn Gly Ile Leu Asn Val Thr Ala Thr Asp Lys Ser
                485                 490                 495

Thr Gly Lys Val Asn Lys Ile Thr Ile Thr Asn Asp Lys Gly Arg Leu
                500                 505                 510

Ser Lys Glu Glu Ile Glu Arg Met Val Leu Asp Ala Glu Lys Tyr Lys
        515                 520                 525

Ala Glu Asp Glu Val Gln Arg Glu Lys Ile Ala Ala Lys Asn Ala Leu
    530                 535                 540

Glu Ser Tyr Ala Phe Asn Met Lys Ser Val Val Ser Asp Glu Gly Leu
545                 550                 555                 560

Lys Gly Lys Ile Ser Glu Ser Asp Lys Asn Lys Ile Leu Asp Lys Cys
                565                 570                 575

Asn Glu Leu Leu Ser Trp Leu Glu Val Asn Gln Leu Ala Glu Lys Asp
                580                 585                 590

Glu Phe Asp His Lys Arg Lys Glu Leu Glu Gln Met Cys Asn Pro Ile
        595                 600                 605

Ile Thr Lys Leu Tyr Gln Gly Gly Cys Thr Gly Pro Ala Cys Gly Thr
    610                 615                 620

Gly Tyr Val Pro Gly Arg Pro Ala Thr Gly Pro Thr Ile Glu Glu Val
625                 630                 635                 640

Asp

<210> SEQ ID NO 50
<211> LENGTH: 639
<212> TYPE: PRT
<213> ORGANISM: Homo sapiens

<400> SEQUENCE: 50

Met Ser Ala Arg Gly Pro Ala Ile Gly Ile Asp Leu Gly Thr Thr Tyr
1               5                   10                  15

Ser Cys Val Gly Val Phe Gln His Gly Lys Val Glu Ile Ile Ala Asn
            20                  25                  30

Asp Gln Gly Asn Arg Thr Thr Pro Ser Tyr Val Ala Phe Thr Asp Thr

```
                    35                  40                  45
Glu Arg Leu Ile Gly Asp Ala Ala Lys Asn Gln Val Ala Met Asn Pro
 50                  55                  60

Thr Asn Thr Ile Phe Asp Ala Lys Arg Leu Ile Gly Arg Lys Phe Glu
 65                  70                  75                  80

Asp Ala Thr Val Gln Ser Asp Met Lys His Trp Pro Phe Arg Val Val
                     85                  90                  95

Ser Glu Gly Gly Lys Pro Lys Val Gln Val Tyr Lys Gly Glu Thr
                    100                 105                 110

Lys Thr Phe Phe Pro Glu Glu Ile Ser Ser Met Val Leu Thr Lys Met
                    115                 120                 125

Lys Glu Ile Ala Glu Ala Tyr Leu Gly Gly Lys Val His Ser Ala Val
                    130                 135                 140

Ile Thr Val Pro Ala Tyr Phe Asn Asp Ser Gln Arg Gln Ala Thr Lys
 145                 150                 155                 160

Asp Ala Gly Thr Ile Thr Gly Leu Asn Val Leu Arg Ile Ile Asn Glu
                    165                 170                 175

Pro Thr Ala Ala Ala Ile Ala Tyr Gly Leu Asp Lys Lys Gly Cys Ala
                    180                 185                 190

Gly Gly Glu Lys Asn Val Leu Ile Phe Asp Leu Gly Gly Thr Phe
                    195                 200                 205

Asp Val Ser Ile Leu Thr Ile Glu Asp Gly Ile Phe Glu Val Lys Ser
                    210                 215                 220

Thr Ala Gly Asp Thr His Leu Gly Gly Glu Asp Phe Asp Asn Arg Met
 225                 230                 235                 240

Val Ser His Leu Ala Glu Glu Phe Lys Arg Lys His Lys Lys Asp Ile
                    245                 250                 255

Gly Pro Asn Lys Arg Ala Val Arg Arg Leu Arg Thr Ala Cys Glu Arg
                    260                 265                 270

Ala Lys Arg Thr Leu Ser Ser Thr Gln Ala Ser Ile Glu Ile Asp
                    275                 280                 285

Ser Leu Tyr Glu Gly Val Asp Phe Tyr Thr Ser Ile Thr Arg Ala Arg
                    290                 295                 300

Phe Glu Glu Leu Asn Ala Asp Leu Phe Arg Gly Thr Leu Glu Pro Val
 305                 310                 315                 320

Glu Lys Ala Leu Arg Asp Ala Lys Leu Asp Lys Gly Gln Ile Gln Glu
                    325                 330                 335

Ile Val Leu Val Gly Gly Ser Thr Arg Ile Pro Lys Ile Gln Lys Leu
                    340                 345                 350

Leu Gln Asp Phe Phe Asn Gly Lys Glu Leu Asn Lys Ser Ile Asn Pro
                    355                 360                 365

Asp Glu Ala Val Ala Tyr Gly Ala Ala Val Gln Ala Ala Ile Leu Ile
                    370                 375                 380

Gly Asp Lys Ser Glu Asn Val Gln Asp Leu Leu Leu Leu Asp Val Thr
 385                 390                 395                 400

Pro Leu Ser Leu Gly Ile Glu Thr Ala Gly Gly Val Met Thr Pro Leu
                    405                 410                 415

Ile Lys Arg Asn Thr Thr Ile Pro Thr Lys Gln Thr Gln Thr Phe Thr
                    420                 425                 430

Thr Tyr Ser Asp Asn Gln Ser Ser Val Leu Val Gln Val Tyr Glu Gly
                    435                 440                 445

Glu Arg Ala Met Thr Lys Asp Asn Asn Leu Leu Gly Lys Phe Asp Leu
                    450                 455                 460
```

-continued

```
Thr Gly Ile Pro Pro Ala Pro Arg Gly Val Pro Gln Ile Glu Val Thr
465                 470                 475                 480

Phe Asp Ile Asp Ala Asn Gly Ile Leu Asn Val Thr Ala Ala Asp Lys
            485                 490                 495

Ser Thr Gly Lys Glu Asn Lys Ile Thr Ile Thr Asn Asp Lys Gly Arg
        500                 505                 510

Leu Ser Lys Asp Asp Ile Asp Arg Met Val Gln Glu Ala Glu Arg Tyr
    515                 520                 525

Lys Ser Glu Asp Glu Ala Asn Arg Asp Arg Val Ala Ala Lys Asn Ala
530                 535                 540

Leu Glu Ser Tyr Thr Tyr Asn Ile Lys Gln Thr Val Glu Asp Glu Lys
545                 550                 555                 560

Leu Arg Gly Lys Ile Ser Glu Gln Asp Lys Asn Lys Ile Leu Asp Lys
                565                 570                 575

Cys Gln Glu Val Ile Asn Trp Leu Asp Arg Asn Gln Met Ala Glu Lys
            580                 585                 590

Asp Glu Tyr Glu His Lys Gln Lys Glu Leu Glu Arg Val Cys Asn Pro
        595                 600                 605

Ile Ile Ser Lys Leu Tyr Gln Gly Gly Pro Gly Gly Gly Ser Gly Gly
    610                 615                 620

Gly Gly Ser Gly Ala Ser Gly Gly Pro Thr Ile Glu Glu Val Asp
625                 630                 635

<210> SEQ ID NO 51
<211> LENGTH: 654
<212> TYPE: PRT
<213> ORGANISM: Homo sapiens

<400> SEQUENCE: 51

Met Lys Leu Ser Leu Val Ala Ala Met Leu Leu Leu Leu Ser Ala Ala
1               5                   10                  15

Arg Ala Glu Glu Glu Asp Lys Lys Glu Asp Val Gly Thr Val Val Gly
            20                  25                  30

Ile Asp Leu Gly Thr Thr Tyr Ser Cys Val Gly Val Phe Lys Asn Gly
        35                  40                  45

Arg Val Glu Ile Ile Ala Asn Asp Gln Gly Asn Arg Ile Thr Pro Ser
    50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
            85                  90                  95

Arg Leu Ile Gly Arg Thr Trp Asn Asp Pro Ser Val Gln Gln Asp Ile
        100                 105                 110

Lys Phe Leu Pro Phe Lys Val Val Glu Lys Lys Thr Lys Pro Tyr Ile
    115                 120                 125

Gln Val Asp Ile Gly Gly Gly Thr Lys Thr Phe Ala Pro Glu Glu
130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
            165                 170                 175

Asn Asp Ala Gln Arg Gln Ala Thr Lys Asp Ala Gly Thr Ile Ala Gly
        180                 185                 190

Leu Asn Val Met Arg Ile Ile Asn Glu Pro Thr Ala Ala Ala Ile Ala
    195                 200                 205
```

```
Tyr Gly Leu Asp Lys Arg Glu Gly Lys Asn Ile Leu Val Phe Asp
            210                 215                 220

Leu Gly Gly Gly Thr Phe Asp Val Ser Leu Leu Thr Ile Asp Asn Gly
225                 230                 235                 240

Val Phe Glu Val Ala Thr Asn Gly Asp Thr His Leu Gly Gly Glu
                245                 250                 255

Asp Phe Asp Gln Arg Val Met Glu His Phe Ile Lys Leu Tyr Lys Lys
                260                 265                 270

Lys Thr Gly Lys Asp Val Arg Lys Asp Asn Arg Ala Val Gln Lys Leu
            275                 280                 285

Arg Arg Glu Val Glu Lys Ala Lys Arg Ala Leu Ser Ser Gln His Gln
290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
                340                 345                 350

Lys Ser Asp Ile Asp Glu Ile Val Leu Val Gly Gly Ser Thr Arg Ile
            355                 360                 365

Pro Lys Ile Gln Gln Leu Val Lys Glu Phe Phe Asn Gly Lys Glu Pro
370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
                420                 425                 430

Met Thr Lys Leu Ile Pro Arg Asn Thr Val Val Pro Thr Lys Lys Ser
            435                 440                 445

Gln Ile Phe Ser Thr Ala Ser Asp Asn Gln Pro Thr Val Thr Ile Lys
450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
                500                 505                 510

Ala Glu Asp Lys Gly Thr Gly Asn Lys Asn Lys Ile Thr Ile Thr Asn
            515                 520                 525

Asp Gln Asn Arg Leu Thr Pro Glu Glu Ile Glu Arg Met Val Asn Asp
530                 535                 540

Ala Glu Lys Phe Ala Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
                565                 570                 575

Gly Asp Lys Glu Lys Leu Gly Gly Lys Leu Ser Ser Glu Asp Lys Glu
                580                 585                 590

Thr Met Glu Lys Ala Val Glu Glu Lys Ile Glu Trp Leu Glu Ser His
            595                 600                 605

Gln Asp Ala Asp Ile Glu Asp Phe Lys Ala Lys Lys Lys Glu Leu Glu
610                 615                 620

Glu Ile Val Gln Pro Ile Ile Ser Lys Leu Tyr Gly Ser Ala Gly Pro
625                 630                 635                 640
```

```
Pro Pro Thr Gly Glu Glu Asp Thr Ala Glu Lys Asp Glu Leu
            645                 650

<210> SEQ ID NO 52
<211> LENGTH: 643
<212> TYPE: PRT
<213> ORGANISM: Homo sapiens

<400> SEQUENCE: 52

Met Gln Ala Pro Arg Glu Leu Ala Val Gly Ile Asp Leu Gly Thr Thr
1               5                   10                  15

Tyr Ser Cys Val Gly Val Phe Gln Gln Gly Arg Val Glu Ile Leu Ala
            20                  25                  30

Asn Asp Gln Gly Asn Arg Thr Thr Pro Ser Tyr Val Ala Phe Thr Asp
        35                  40                  45

Thr Glu Arg Leu Val Gly Asp Ala Ala Lys Ser Gln Ala Ala Leu Asn
    50                  55                  60

Pro His Asn Thr Val Phe Asp Ala Lys Arg Leu Ile Gly Arg Lys Phe
65                  70                  75                  80

Ala Asp Thr Thr Val Gln Ser Asp Met Lys His Trp Pro Phe Arg Val
                85                  90                  95

Val Ser Glu Gly Gly Lys Pro Lys Val Arg Val Cys Tyr Arg Gly Glu
            100                 105                 110

Asp Lys Thr Phe Tyr Pro Glu Glu Ile Ser Ser Met Val Leu Ser Lys
        115                 120                 125

Met Lys Glu Thr Ala Glu Ala Tyr Leu Gly Gln Pro Val Lys His Ala
    130                 135                 140

Val Ile Thr Val Pro Ala Tyr Phe Asn Asp Ser Gln Arg Gln Ala Thr
145                 150                 155                 160

Lys Asp Ala Gly Ala Ile Ala Gly Leu Asn Val Leu Arg Ile Ile Asn
                165                 170                 175

Glu Pro Thr Ala Ala Ala Ile Ala Tyr Gly Leu Asp Arg Arg Gly Ala
            180                 185                 190

Gly Glu Arg Asn Val Leu Ile Phe Asp Leu Gly Gly Gly Thr Phe Asp
        195                 200                 205

Val Ser Val Leu Ser Ile Asp Ala Gly Val Phe Glu Val Lys Ala Thr
    210                 215                 220

Ala Gly Asp Thr His Leu Gly Gly Glu Asp Phe Asp Asn Arg Leu Val
225                 230                 235                 240

Asn His Phe Met Glu Glu Phe Arg Arg Lys His Gly Lys Asp Leu Ser
                245                 250                 255

Gly Asn Lys Arg Ala Leu Arg Arg Leu Arg Thr Ala Cys Glu Arg Ala
            260                 265                 270

Lys Arg Thr Leu Ser Ser Ser Thr Gln Ala Thr Leu Glu Ile Asp Ser
        275                 280                 285

Leu Phe Glu Gly Val Asp Phe Tyr Thr Ser Ile Thr Arg Ala Arg Phe
    290                 295                 300

Glu Glu Leu Cys Ser Asp Leu Phe Arg Ser Thr Leu Glu Pro Val Glu
305                 310                 315                 320

Lys Ala Leu Arg Asp Ala Lys Leu Asp Lys Ala Gln Ile His Asp Val
                325                 330                 335

Val Leu Val Gly Gly Ser Thr Arg Ile Pro Lys Val Gln Lys Leu Leu
            340                 345                 350

Gln Asp Phe Phe Asn Gly Lys Glu Leu Asn Lys Ser Ile Asn Pro Asp
        355                 360                 365
```

```
Glu Ala Val Ala Tyr Gly Ala Val Gln Ala Val Leu Met Gly
    370                 375                 380

Asp Lys Cys Glu Lys Val Gln Asp Leu Leu Leu Asp Val Ala Pro
385                 390                 395                 400

Leu Ser Leu Gly Leu Glu Thr Ala Gly Gly Val Met Thr Thr Leu Ile
                405                 410                 415

Gln Arg Asn Ala Thr Ile Pro Thr Lys Gln Thr Gln Thr Phe Thr Thr
            420                 425                 430

Tyr Ser Asp Asn Gln Pro Gly Val Phe Ile Gln Val Tyr Glu Gly Glu
            435                 440                 445

Arg Ala Met Thr Lys Asp Asn Asn Leu Leu Gly Arg Phe Glu Leu Ser
    450                 455                 460

Gly Ile Pro Pro Ala Pro Arg Gly Val Pro Gln Ile Glu Val Thr Phe
465                 470                 475                 480

Asp Ile Asp Ala Asn Gly Ile Leu Ser Val Thr Ala Thr Asp Arg Ser
                485                 490                 495

Thr Gly Lys Ala Asn Lys Ile Thr Ile Thr Asn Asp Lys Gly Arg Leu
            500                 505                 510

Ser Lys Glu Glu Val Glu Arg Met Val His Glu Ala Glu Gln Tyr Lys
            515                 520                 525

Ala Glu Asp Glu Ala Gln Arg Asp Arg Val Ala Ala Lys Asn Ser Leu
    530                 535                 540

Glu Ala His Val Phe His Val Lys Gly Ser Leu Gln Glu Glu Ser Leu
545                 550                 555                 560

Arg Asp Lys Ile Pro Glu Asp Arg Arg Lys Met Gln Asp Lys Cys
                565                 570                 575

Arg Glu Val Leu Ala Trp Leu Glu His Asn Gln Leu Ala Glu Lys Glu
            580                 585                 590

Glu Tyr Glu His Gln Lys Arg Glu Leu Glu Gln Ile Cys Arg Pro Ile
            595                 600                 605

Phe Ser Arg Leu Tyr Gly Gly Pro Gly Val Pro Gly Gly Ser Ser Cys
            610                 615                 620

Gly Thr Gln Ala Arg Gln Gly Asp Pro Ser Thr Gly Pro Ile Ile Glu
625                 630                 635                 640

Glu Val Asp

<210> SEQ ID NO 53
<211> LENGTH: 646
<212> TYPE: PRT
<213> ORGANISM: Homo sapiens

<400> SEQUENCE: 53

Met Ser Lys Gly Pro Ala Val Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Met Asn Pro Thr
    50                  55                  60

Asn Thr Val Phe Asp Ala Lys Arg Leu Ile Gly Arg Arg Phe Asp Asp
65                  70                  75                  80

Ala Val Val Gln Ser Asp Met Lys His Trp Pro Phe Met Val Val Asn
                85                  90                  95
```

Asp Ala Gly Arg Pro Lys Val Gln Val Glu Tyr Lys Gly Glu Thr Lys
          100                 105                 110

Ser Phe Tyr Pro Glu Val Ser Ser Met Val Leu Thr Lys Met Lys
        115                 120                 125

Glu Ile Ala Glu Ala Tyr Leu Gly Lys Thr Val Thr Asn Ala Val Val
130                 135                 140

Thr Val Pro Ala Tyr Phe Asn Asp Ser Gln Arg Gln Ala Thr Lys Asp
145                 150                 155                 160

Ala Gly Thr Ile Ala Gly Leu Asn Val Leu Arg Ile Ile Asn Glu Pro
                165                 170                 175

Thr Ala Ala Ala Ile Ala Tyr Gly Leu Asp Lys Lys Val Gly Ala Glu
                180                 185                 190

Arg Asn Val Leu Ile Phe Asp Leu Gly Gly Gly Thr Phe Asp Val Ser
            195                 200                 205

Ile Leu Thr Ile Glu Asp Gly Ile Phe Glu Val Lys Ser Thr Ala Gly
            210                 215                 220

Asp Thr His Leu Gly Gly Glu Asp Phe Asp Asn Arg Met Val Asn His
225                 230                 235                 240

Phe Ile Ala Glu Phe Lys Arg Lys His Lys Lys Asp Ile Ser Glu Asn
                245                 250                 255

Lys Arg Ala Val Arg Arg Leu Arg Thr Ala Cys Glu Arg Ala Lys Arg
                260                 265                 270

Thr Leu Ser Ser Ser Thr Gln Ala Ser Ile Glu Ile Asp Ser Leu Tyr
            275                 280                 285

Glu Gly Ile Asp Phe Tyr Thr Ser Ile Thr Arg Ala Arg Phe Glu Glu
            290                 295                 300

Leu Asn Ala Asp Leu Phe Arg Gly Thr Leu Asp Pro Val Glu Lys Ala
305                 310                 315                 320

Leu Arg Asp Ala Lys Leu Asp Lys Ser Gln Ile His Asp Ile Val Leu
                325                 330                 335

Val Gly Gly Ser Thr Arg Ile Pro Lys Ile Gln Lys Leu Leu Gln Asp
                340                 345                 350

Phe Phe Asn Gly Lys Glu Leu Asn Lys Ser Ile Asn Pro Asp Glu Ala
            355                 360                 365

Val Ala Tyr Gly Ala Ala Val Gln Ala Ala Ile Leu Ser Gly Asp Lys
            370                 375                 380

Ser Glu Asn Val Gln Asp Leu Leu Leu Leu Asp Val Thr Pro Leu Ser
385                 390                 395                 400

Leu Gly Ile Glu Thr Ala Gly Gly Val Met Thr Val Leu Ile Lys Arg
                405                 410                 415

Asn Thr Thr Ile Pro Thr Lys Gln Thr Gln Thr Phe Thr Thr Tyr Ser
                420                 425                 430

Asp Asn Gln Pro Gly Val Leu Ile Gln Val Tyr Glu Gly Glu Arg Ala
            435                 440                 445

Met Thr Lys Asp Asn Asn Leu Leu Gly Lys Phe Glu Leu Thr Gly Ile
        450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Ser Ala Val Asp Lys Ser Thr Gly
                485                 490                 495

Lys Glu Asn Lys Ile Thr Ile Thr Asn Asp Lys Gly Arg Leu Ser Lys
                500                 505                 510

Glu Asp Ile Glu Arg Met Val Gln Glu Ala Glu Lys Tyr Lys Ala Glu
            515                 520                 525

Asp Glu Lys Gln Arg Asp Lys Val Ser Ser Lys Asn Ser Leu Glu Ser
             530                 535                 540

Tyr Ala Phe Asn Met Lys Ala Thr Val Glu Asp Glu Lys Leu Gln Gly
545                 550                 555                 560

Lys Ile Asn Asp Glu Asp Lys Gln Lys Ile Leu Asp Lys Cys Asn Glu
                565                 570                 575

Ile Ile Asn Trp Leu Asp Lys Asn Gln Thr Ala Glu Lys Glu Glu Phe
            580                 585                 590

Glu His Gln Gln Lys Glu Leu Glu Lys Val Cys Asn Pro Ile Ile Thr
        595                 600                 605

Lys Leu Tyr Gln Ser Ala Gly Gly Met Pro Gly Gly Met Pro Gly Gly
    610                 615                 620

Phe Pro Gly Gly Gly Ala Pro Pro Ser Gly Gly Ala Ser Ser Gly Pro
625                 630                 635                 640

Thr Ile Glu Glu Val Asp
                645

<210> SEQ ID NO 54
<211> LENGTH: 679
<212> TYPE: PRT
<213> ORGANISM: Homo sapiens

<400> SEQUENCE: 54

Met Ile Ser Ala Ser Arg Ala Ala Ala Arg Leu Val Gly Ala Ala
1               5                   10                  15

Ala Ser Arg Gly Pro Thr Ala Ala Arg His Gln Asp Ser Trp Asn Gly
            20                  25                  30

Leu Ser His Glu Ala Phe Arg Leu Val Ser Arg Arg Asp Tyr Ala Ser
        35                  40                  45

Glu Ala Ile Lys Gly Ala Val Val Gly Ile Asp Leu Gly Thr Thr Asn
    50                  55                  60

Ser Cys Val Ala Val Met Glu Gly Lys Gln Ala Lys Val Leu Glu Asn
65                  70                  75                  80

Ala Glu Gly Ala Arg Thr Thr Pro Ser Val Val Ala Phe Thr Ala Asp
                85                  90                  95

Gly Glu Arg Leu Val Gly Met Pro Ala Lys Arg Gln Ala Val Thr Asn
            100                 105                 110

Pro Asn Asn Thr Phe Tyr Ala Thr Lys Arg Leu Ile Gly Arg Arg Tyr
        115                 120                 125

Asp Asp Pro Glu Val Gln Lys Asp Ile Lys Asn Val Pro Phe Lys Ile
    130                 135                 140

Val Arg Ala Ser Asn Gly Asp Ala Trp Val Glu Ala His Gly Lys Leu
145                 150                 155                 160

Tyr Ser Pro Ser Gln Ile Gly Ala Phe Val Leu Met Lys Met Lys Glu
                165                 170                 175

Thr Ala Glu Asn Tyr Leu Gly His Thr Ala Lys Asn Ala Val Ile Thr
            180                 185                 190

Val Pro Ala Tyr Phe Asn Asp Ser Gln Arg Gln Ala Thr Lys Asp Ala
        195                 200                 205

Gly Gln Ile Ser Gly Leu Asn Val Leu Arg Val Ile Asn Glu Pro Thr
    210                 215                 220

Ala Ala Ala Leu Ala Tyr Gly Leu Asp Lys Ser Glu Asp Lys Val Ile
225                 230                 235                 240

Ala Val Tyr Asp Leu Gly Gly Gly Thr Phe Asp Ile Ser Ile Leu Glu
                245                 250                 255

-continued

```
Ile Gln Lys Gly Val Phe Glu Val Lys Ser Thr Asn Gly Asp Thr Phe
                260                 265                 270

Leu Gly Gly Glu Asp Phe Asp Gln Ala Leu Leu Arg His Ile Val Lys
            275                 280                 285

Glu Phe Lys Arg Glu Thr Gly Val Asp Leu Thr Lys Asp Asn Met Ala
290                 295                 300

Leu Gln Arg Val Arg Glu Ala Ala Glu Lys Ala Lys Cys Glu Leu Ser
305                 310                 315                 320

Ser Ser Val Gln Thr Asp Ile Asn Leu Pro Tyr Leu Thr Met Asp Ser
                325                 330                 335

Ser Gly Pro Lys His Leu Asn Met Lys Leu Thr Arg Ala Gln Phe Glu
                340                 345                 350

Gly Ile Val Thr Asp Leu Ile Arg Arg Thr Ile Ala Pro Cys Gln Lys
            355                 360                 365

Ala Met Gln Asp Ala Glu Val Ser Lys Ser Asp Ile Gly Glu Val Ile
370                 375                 380

Leu Val Gly Gly Met Thr Arg Met Pro Lys Val Gln Gln Thr Val Gln
385                 390                 395                 400

Asp Leu Phe Gly Arg Ala Pro Ser Lys Ala Val Asn Pro Asp Glu Ala
                405                 410                 415

Val Ala Ile Gly Ala Ala Ile Gln Gly Gly Val Leu Ala Gly Asp Val
                420                 425                 430

Thr Asp Val Leu Leu Leu Asp Val Thr Pro Leu Ser Leu Gly Ile Glu
            435                 440                 445

Thr Leu Gly Gly Val Phe Thr Lys Leu Ile Asn Arg Asn Thr Thr Ile
450                 455                 460

Pro Thr Lys Lys Ser Gln Val Phe Ser Thr Ala Ala Asp Gly Gln Thr
465                 470                 475                 480

Gln Val Glu Ile Lys Val Cys Gln Gly Glu Arg Glu Met Ala Gly Asp
                485                 490                 495

Asn Lys Leu Leu Gly Gln Phe Thr Leu Ile Gly Ile Pro Pro Ala Pro
                500                 505                 510

Arg Gly Val Pro Gln Ile Glu Val Thr Phe Asp Ile Asp Ala Asn Gly
            515                 520                 525

Ile Val His Val Ser Ala Lys Asp Lys Gly Thr Gly Arg Glu Gln Gln
530                 535                 540

Ile Val Ile Gln Ser Ser Gly Gly Leu Ser Lys Asp Asp Ile Glu Asn
545                 550                 555                 560

Met Val Lys Asn Ala Glu Lys Tyr Ala Glu Glu Asp Arg Arg Lys Lys
                565                 570                 575

Glu Arg Val Glu Ala Val Asn Met Ala Glu Gly Ile Ile His Asp Thr
            580                 585                 590

Glu Thr Lys Met Glu Glu Phe Lys Asp Gln Leu Pro Ala Asp Glu Cys
            595                 600                 605

Asn Lys Leu Lys Glu Glu Ile Ser Lys Met Arg Glu Leu Leu Ala Arg
            610                 615                 620

Lys Asp Ser Glu Thr Gly Glu Asn Ile Arg Gln Ala Ala Ser Ser Leu
625                 630                 635                 640

Gln Gln Ala Ser Leu Lys Leu Phe Glu Met Ala Tyr Lys Lys Met Ala
                645                 650                 655

Ser Glu Arg Glu Gly Ser Gly Ser Ser Gly Thr Gly Glu Gln Lys Glu
            660                 665                 670

Asp Gln Lys Glu Glu Lys Gln
```

675

<210> SEQ ID NO 55
<211> LENGTH: 625
<212> TYPE: PRT
<213> ORGANISM: Mycobacterium tuberculosis

<400> SEQUENCE: 55

Met Ala Arg Ala Val Gly Ile Asp Leu Gly Thr Thr Asn Ser Val Val
1               5                   10                  15

Ser Val Leu Glu Gly Gly Asp Pro Val Val Ala Asn Ser Glu Gly
        20                  25                  30

Ser Arg Thr Thr Pro Ser Ile Val Ala Phe Ala Arg Asn Gly Glu Val
            35                  40                  45

Leu Val Gly Gln Pro Ala Lys Asn Gln Ala Val Thr Asn Val Asp Arg
        50                  55                  60

Thr Val Arg Ser Val Lys Arg His Met Gly Ser Asp Trp Ser Ile Glu
65                  70                  75                  80

Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
            100                 105                 110

Asp Ala Val Ile Thr Thr Pro Ala Tyr Phe Asn Asp Ala Gln Arg Gln
        115                 120                 125

Ala Thr Lys Asp Ala Gly Gln Ile Ala Gly Leu Asn Val Leu Arg Ile
130                 135                 140

Val Asn Glu Pro Thr Ala Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
        195                 200                 205

Val Asp Trp Leu Val Asp Lys Phe Lys Gly Thr Ser Gly Ile Asp Leu
        210                 215                 220

Thr Lys Asp Lys Met Ala Met Gln Arg Leu Arg Glu Ala Ala Glu Lys
225                 230                 235                 240

Ala Lys Ile Glu Leu Ser Ser Ser Gln Ser Thr Ser Ile Asn Leu Pro
                245                 250                 255

Tyr Ile Thr Val Asp Ala Asp Lys Asn Pro Leu Phe Leu Asp Glu Gln
            260                 265                 270

Leu Thr Arg Ala Glu Phe Gln Arg Ile Thr Gln Asp Leu Leu Asp Arg
        275                 280                 285

Thr Arg Lys Pro Phe Gln Ser Val Ile Ala Asp Thr Gly Ile Ser Val
        290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Gly Lys Glu Pro Asn
                325                 330                 335

Lys Gly Val Asn Pro Asp Glu Val Ala Val Gly Ala Ala Leu Gln
            340                 345                 350

Ala Gly Val Leu Lys Gly Glu Val Lys Asp Val Leu Leu Leu Asp Val
        355                 360                 365

Thr Pro Leu Ser Leu Gly Ile Glu Thr Lys Gly Gly Val Met Thr Arg

```
                    370                 375                 380
Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
                405                 410                 415

Gly Glu Arg Glu Ile Ala Ala His Asn Lys Leu Leu Gly Ser Phe Glu
                420                 425                 430

Leu Thr Gly Ile Pro Pro Ala Pro Arg Gly Ile Pro Gln Ile Glu Val
                435                 440                 445

Thr Phe Asp Ile Asp Ala Asn Gly Ile Val His Val Thr Ala Lys Asp
450                 455                 460

Lys Gly Thr Gly Lys Glu Asn Thr Ile Arg Ile Gln Glu Gly Ser Gly
465                 470                 475                 480

Leu Ser Lys Glu Asp Ile Asp Arg Met Ile Lys Asp Ala Glu Ala His
                485                 490                 495

Ala Glu Glu Asp Arg Lys Arg Arg Glu Glu Ala Asp Val Arg Asn Gln
                500                 505                 510

Ala Glu Thr Leu Val Tyr Gln Thr Glu Lys Phe Val Lys Glu Gln Arg
                515                 520                 525

Glu Ala Glu Gly Gly Ser Lys Val Pro Glu Asp Thr Leu Asn Lys Val
530                 535                 540

Asp Ala Ala Val Ala Glu Ala Lys Ala Ala Leu Gly Gly Ser Asp Ile
545                 550                 555                 560

Ser Ala Ile Lys Ser Ala Met Glu Lys Leu Gly Gln Glu Ser Gln Ala
                565                 570                 575

Leu Gly Gln Ala Ile Tyr Glu Ala Ala Gln Ala Ala Ser Gln Ala Thr
                580                 585                 590

Gly Ala Ala His Pro Gly Gly Glu Pro Gly Gly Ala His Pro Gly Ser
                595                 600                 605

Ala Asp Asp Val Val Asp Ala Glu Val Val Asp Gly Arg Glu Ala
    610                 615                 620

Lys
625

<210> SEQ ID NO 56
<211> LENGTH: 20
<212> TYPE: PRT
<213> ORGANISM: Home sapiens

<400> SEQUENCE: 56

Leu Asn Val Leu Arg Ile Ile Asn Glu Pro Thr Ala Ala Ala Ile Ala
1               5                   10                  15

Tyr Gly Leu Asp
            20

<210> SEQ ID NO 57
<211> LENGTH: 20
<212> TYPE: PRT
<213> ORGANISM: Homo sapiens

<400> SEQUENCE: 57

Leu Asn Val Met Arg Ile Ile Asn Glu Pro Thr Ala Ala Ala Ile Ala
1               5                   10                  15

Tyr Gly Leu Asp
            20

<210> SEQ ID NO 58
```

```
<211> LENGTH: 20
<212> TYPE: PRT
<213> ORGANISM: Homo sapiens

<400> SEQUENCE: 58

Leu Asn Val Leu Arg Val Ile Asn Glu Pro Thr Ala Ala Ala Leu Ala
1               5                   10                  15

Tyr Gly Leu Asp
            20

<210> SEQ ID NO 59
<211> LENGTH: 20
<212> TYPE: PRT
<213> ORGANISM: Homo sapiens

<400> SEQUENCE: 59

Leu Lys Val Leu Pro Ile Ile Asn Glu Ala Thr Ala Ala Ala Ile Ala
1               5                   10                  15

Tyr Gly Leu Asp
            20

<210> SEQ ID NO 60
<211> LENGTH: 20
<212> TYPE: PRT
<213> ORGANISM: Homo sapiens

<400> SEQUENCE: 60

Phe Asn Val Leu Arg Leu Ile His Glu Pro Ser Ala Ala Leu Leu Ala
1               5                   10                  15

Tyr Gly Ile Gly
            20

<210> SEQ ID NO 61
<211> LENGTH: 20
<212> TYPE: PRT
<213> ORGANISM: Drosophila melanogaster

<400> SEQUENCE: 61

Leu Asn Val Leu Arg Ile Ile Asn Glu Pro Thr Ala Ala Ala Leu Ala
1               5                   10                  15

Tyr Gly Leu Asp
            20

<210> SEQ ID NO 62
<211> LENGTH: 20
<212> TYPE: PRT
<213> ORGANISM: Arabidopsis thaliana

<400> SEQUENCE: 62

Leu Asn Val Ala Arg Ile Ile Asn Glu Pro Thr Ala Ala Ala Ile Ala
1               5                   10                  15

Tyr Gly Leu Asp
            20

<210> SEQ ID NO 63
<211> LENGTH: 20
<212> TYPE: PRT
<213> ORGANISM: Saccharomyces cerevisiae

<400> SEQUENCE: 63

Met Asn Val Leu Arg Ile Ile Asn Glu Pro Thr Ala Ala Ala Ile Ala
1               5                   10                  15

Tyr Gly Leu Asp
```

-continued

```
<210> SEQ ID NO 64
<211> LENGTH: 20
<212> TYPE: PRT
<213> ORGANISM: Saccharomyces cerevisiae

<400> SEQUENCE: 64

Leu Asn Val Leu Arg Ile Ile Asn Glu Pro Thr Ala Ala Ile Ala
1               5                   10                  15

Tyr Gly Leu Gly
            20

<210> SEQ ID NO 65
<211> LENGTH: 20
<212> TYPE: PRT
<213> ORGANISM: Candida albicans

<400> SEQUENCE: 65

Leu Asn Val Leu Arg Val Val Asn Glu Pro Thr Ala Ala Leu Ala
1               5                   10                  15

Tyr Gly Leu Glu
            20

<210> SEQ ID NO 66
<211> LENGTH: 20
<212> TYPE: PRT
<213> ORGANISM: Lactobacillus lactis

<400> SEQUENCE: 66

Leu Glu Val Glu Arg Ile Val Asn Glu Pro Thr Ala Ala Leu Ala
1               5                   10                  15

Tyr Gly Leu Asp
            20

<210> SEQ ID NO 67
<211> LENGTH: 20
<212> TYPE: PRT
<213> ORGANISM: Lactobacillus delbrueckii

<400> SEQUENCE: 67

Leu Asn Val Gln Arg Ile Ile Asn Glu Pro Thr Ala Ser Ala Leu Ala
1               5                   10                  15

Tyr Gly Leu Asp
            20

<210> SEQ ID NO 68
<211> LENGTH: 20
<212> TYPE: PRT
<213> ORGANISM: Lactobacillus helveticus

<400> SEQUENCE: 68

Leu Asn Val Gln Arg Ile Ile Asn Glu Pro Thr Ala Ser Ala Leu Ala
1               5                   10                  15

Phe Gly Leu Asn
            20

<210> SEQ ID NO 69
<211> LENGTH: 20
<212> TYPE: PRT
<213> ORGANISM: Bacillus subtilis

<400> SEQUENCE: 69
```

-continued

Leu Glu Val Glu Arg Ile Ile Asn Glu Pro Thr Ala Ala Ala Leu Ala
1               5                   10                  15

Tyr Gly Leu Asp
            20

<210> SEQ ID NO 70
<211> LENGTH: 20
<212> TYPE: PRT
<213> ORGANISM: Escherichia coli

<400> SEQUENCE: 70

Leu Glu Val Lys Arg Ile Ile Asn Glu Pro Thr Ala Ala Ala Leu Ala
1               5                   10                  15

Tyr Gly Leu Asp
            20

<210> SEQ ID NO 71
<211> LENGTH: 20
<212> TYPE: PRT
<213> ORGANISM: Mycoplasma mycoides

<400> SEQUENCE: 71

Leu Gln Val Glu Arg Ile Ile Asn Glu Pro Thr Ala Ala Ala Leu Ala
1               5                   10                  15

Tyr Gly Leu Asp
            20

<210> SEQ ID NO 72
<211> LENGT

<213> ORGANISM: Arabidopsis thaliana

<400> SEQUENCE: 75

Ile Ile Ala Asn Asp Gln Gly Asn Arg Thr Thr Pro Ser Tyr Val Ala
1               5                   10                  15

Phe Thr Asp Ser
            20

<210> SEQ ID NO 76
<211> LENGTH: 20
<212> TYPE: PRT
<213> ORGANISM: Saccharomyces cerevisiae

<400> SEQUENCE: 76

Ile Ile Ala Asn Asp Gln Gly Asn Arg Thr Thr Pro Ser Tyr Val Ala
1               5                   10                  15

Phe Thr Asp Thr
            20

<210> SEQ ID NO 77
<211> LENGTH: 20
<212> TYPE: PRT
<213> ORGANISM: Saccharomyces cerevisiae

<400> SEQUENCE: 77

Ile Ile Ala Asn Glu Gln Gly Asn Arg Val Thr Pro Ser Phe Val Ala
1               5                   10                  15

Phe Thr Pro Gln
            20

<210> SEQ ID NO 78
<211> LENGTH: 20
<212> TYPE: PRT
<213> ORGANISM: Bacillus halodurans

<400> SEQUENCE: 78

Val Ile Pro Asn Pro Glu Gly Asn Arg Thr Thr Pro Ser Val Val Ala
1               5                   10                  15

Phe Lys Asp Gly
            20

<210> SEQ ID NO 79
<211> LENGTH: 20
<212> TYPE: PRT
<213> ORGANISM: Bacillus subtilis

<400> SEQUENCE: 79

Val Ile Ala Asn Ala Glu Gly Asn Arg Thr Thr Pro Ser Val Val Ala
1               5                   10                  15

Phe Lys Asn Gly
            20

<210> SEQ ID NO 80
<211> LENGTH: 20
<212> TYPE: PRT
<213> ORGANISM: Mycobacterium tuberculosis

<400> SEQUENCE: 80

Val Val Ala Asn Ser Glu Gly Ser Arg Thr Thr Pro Ser Ile Val Ala
1               5                   10                  15

Phe Ala Arg Asn
            20

```
<210> SEQ ID NO 81
<211> LENGTH: 20
<212> TYPE: PRT
<213> ORGANISM: Mycobacterium leprae

<400> SEQUENCE: 81

Val Val Ala Asn Ser Glu Gly Ser Arg Thr Thr Pro Ser Thr Val Ala
1               5                   10                  15

Phe Ala Arg Asn
            20

<210> SEQ ID NO 82
<211> LENGTH: 20
<212> TYPE: PRT
<213> ORGANISM: Mycobacterium gilvum

<400> SEQUENCE: 82

Val Val Ala Asn Ser Glu Gly Ser Arg Thr Thr Pro Ser Val Val Ala
1               5                   10                  15

Phe Ala Arg Asn
            20

<210> SEQ ID NO 83
<211> LENGTH: 20
<212> TYPE: PRT
<213> ORGANISM: Homo sapiens

<400> SEQUENCE: 83

Asn Pro Asp Glu Ala Val Ala Tyr Gly Ala Ala Val Gln Ala Ala Ile
1               5                   10                  15

Leu Met Gly Asp
            20

<210> SEQ ID NO 84
<211> LENGTH: 20
<212> TYPE: PRT
<213> ORGANISM: Homo sapiens

<400> SEQUENCE: 84

Asn Pro Asp Glu Ala Val Ala Tyr Gly Ala Ala Val Gln Ala Ala Ile
1               5                   10                  15

Leu Ile Gly Asp
            20

<210> SEQ ID NO 85
<211> LENGTH: 20
<212> TYPE: PRT
<213> ORGANISM: Homo sapiens

<400> SEQUENCE: 85

Asn Pro Asp Glu Ala Val Ala Tyr Gly Ala Ala Val Gln Ala Gly Val
1               5                   10                  15

Leu Ser Gly Asp
            20

<210> SEQ ID NO 86
<211> LENGTH: 20
<212> TYPE: PRT
<213> ORGANISM: Homo sapiens

<400> SEQUENCE: 86

Asn Pro Asp Glu Ala Val Ala Tyr Gly Ala Ala Val Gln Ala Ala Val
1               5                   10                  15
```

```
<210> SEQ ID NO 87
<211> LENGTH: 20
<212> TYPE: PRT
<213> ORGANISM: Homo sapiens

<400> SEQUENCE: 87

Asn Pro Asp Glu Ala Val Ala Tyr Gly Ala Ala Val Gln Ala Ala Ile
1               5                   10                  15

Leu Ser Gly Asp
            20

<210> SEQ ID NO 88
<211> LENGTH: 20
<212> TYPE: PRT
<213> ORGANISM: Homo sapiens

<400> SEQUENCE: 88

Asn Pro Asp Glu Ala Val Ala Ile Gly Ala Ala Ile Gln Gly Gly Val
1               5                   10                  15

Leu Ala Gly Asp
            20

<210> SEQ ID NO 89
<211> LENGTH: 20
<212> TYPE: PRT
<213> ORGANISM: Arabidopsis thaliana

<400> SEQUENCE: 89

Asn Pro Asp Glu Ala Val Ala Tyr Gly Ala Ala Val Gln Gly Ala Ile
1               5                   10                  15

Leu Ser Gly Glu
            20

<210> SEQ ID NO 90
<211> LENGTH: 20
<212> TYPE: PRT
<213> ORGANISM: Saccharomyces cerevisiae

<400> SEQUENCE: 90

Asn Pro Asp Glu Ala Val Ala Tyr Gly Ala Ala Val Gln Ala Ala Ile
1               5                   10                  15

Leu Thr Gly Asp
            20

<210> SEQ ID NO 91
<211> LENGTH: 20
<212> TYPE: PRT
<213> ORGANISM: Saccharomyces cerevisiae

<400> SEQUENCE: 91

Asn Pro Asp Glu Ala Val Ala Tyr Gly Ala Ala Val Gln Gly Ala Ile
1               5                   10                  15

Leu Thr Gly Gln
            20

<210> SEQ ID NO 92
<211> LENGTH: 20
<212> TYPE: PRT
<213> ORGANISM: Bacillus halodurans
```

(Leu Met Gly Asp / 20 appears at top as continuation of previous sequence)

```
<400> SEQUENCE: 92

Asn Pro Asp Glu Val Val Ala Leu Gly Ala Ala Val Gln Ala Gly Val
1               5                   10                  15

Leu Thr Gly Asp
            20

<210> SEQ ID NO 93
<211> LENGTH: 20
<212> TYPE: PRT
<213> ORGANISM: Mycoplasma mycoides

<400> SEQUENCE: 93

Asn Pro Asp Glu Val Val Ala Met Gly Ala Ala Val Gln Gly

```
<211> LENGTH: 20
<212> TYPE: PRT
<213> ORGANISM: Homo sapiens

<400> SEQUENCE: 98

Thr Ile Pro Thr Lys Gln Thr Gln Thr Phe Thr Thr Tyr Ser Asp Asn
1               5                   10                  15

Gln Pro Gly Val
            20

<210> SEQ ID NO 99
<211> LENGTH: 20
<212> TYPE: PRT
<213> ORGANISM: Homo sapiens

<400> SEQUENCE: 99

Thr Ile Pro Thr Lys Lys Ser Gln Val Phe Ser Thr Ala Ala Asp Gly
1               5                   10                  15

Gln Thr Gln Val
            20

<210> SEQ ID NO 100
<211> LENGTH: 20
<212> TYPE: PRT
<213> ORGANISM: Arabidopsis thaliana

<400> SEQUENCE: 100

Thr Ile Pro Thr Lys Lys Glu Gln Val Phe Ser Thr Tyr Ser Asp Asn
1               5                   10                  15

Gln Pro Gly Val
            20

<210> SEQ ID NO 101
<211> LENGTH: 20
<212> TYPE: PRT
<213> ORGANISM: Saccharomyces cerevisiae

<400> SEQUENCE: 101

Thr Ile Pro Thr Lys Lys Ser Glu Thr Phe Ser Thr Tyr Ala Asp Asn
1               5                   10                  15

Gln Pro Gly Val
            20

<210> SEQ ID NO 102
<211> LENGTH: 20
<212> TYPE: PRT
<213> ORGANISM: Saccharomyces cerevisiae

<400> SEQUENCE: 102

Thr Val Pro Thr Ile Lys Arg Arg Thr Phe Thr Thr Val Ser Asp Asn
1               5                   10                  15

Gln Thr Thr Val
            20

<210> SEQ ID NO 103
<211> LENGTH: 20
<212> TYPE: PRT
<213> ORGANISM: Bacillus halodurans

<400> SEQUENCE: 103

Thr Ile Pro Thr Ser Lys Ser Gln Ile Phe Ser Thr Ala Ala Asp Asn
1               5                   10                  15

Gln Pro Ser Val
```

<210> SEQ ID NO 104
<211> LENGTH: 20
<212> TYPE: PRT
<213> ORGANISM: Mycoplasma mycoides

<400> SEQUENCE:

Glu Gly Glu Arg Ala Met Thr Lys Asp Asn Asn Leu Leu Gly Lys Phe
1               5                   10                  15

Asp Leu Thr Gly
            20

<210> SEQ ID NO 110
<211> LENGTH: 20
<212> TYPE: PRT
<213> ORGANISM: Homo sapiens

<400> SEQUENCE: 110

Glu Gly Glu Arg Pro Leu Thr Lys Asp Asn His Leu Leu Gly Thr Phe
1               5                   10                  15

Asp Leu Thr Gly
            20

<210> SEQ ID NO 111
<211> LENGTH: 20
<212> TYPE: PRT
<213> ORGANISM: Homo sapiens

<400> SEQUENCE: 111

Glu Gly Glu Arg Ala Met Thr Lys Asp Asn Asn Leu Leu Gly Lys Phe
1               5                   10                  15

Glu Leu Thr Gly
            20

<210> SEQ ID NO 112
<211> LENGTH: 20
<212> TYPE: PRT
<213> ORGANISM: Homo sapiens

<400> SEQUENCE: 112

Gln Gly Glu Arg Glu Met Ala Gly Asp Asn Lys Leu Leu Gly Gln Phe
1               5                   10                  15

Thr Leu Ile Gly
            20

<210> SEQ ID NO 113
<211> LENGTH: 20
<212> TYPE: PRT
<213> ORGANISM: Arabidopsis thaliana

<400> SEQUENCE: 113

Glu Gly Glu Arg Ala Arg Thr Lys Asp Asn Asn Leu Leu Gly Lys Phe
1               5                   10                  15

Glu Leu Ser Gly
            20

<210> SEQ ID NO 114
<211> LENGTH: 20
<212> TYPE: PRT
<213> ORGANISM: Saccharomyces cerevisiae

<400> SEQUENCE: 114

Glu Gly Glu Arg Thr Arg Thr Lys Asp Asn Asn Leu Leu Gly Lys Phe
1               5                   10                  15

Glu Leu Ser Gly
            20

<210> SEQ ID NO 115
<211> LENGTH: 20
<212> TYPE: PRT

<213> ORGANISM: Saccharomyces cerevisiae

<400> SEQUENCE: 115

Gln Gly Glu Arg Val Asn Cys Lys Glu Asn Thr Leu Leu Gly Glu Phe
1               5                   10                  15

Asp Leu Lys Asn
            20

<210> SEQ ID NO 116
<211> LENGTH: 20
<212> TYPE: PRT
<213> ORGANISM: Bacillus halodurans

<400> SEQUENCE: 116

Gln Gly Glu Arg Glu Met Ala Ala Asp Asn Lys Thr Leu Gly Arg Phe
1               5                   10                  15

Gln Leu Thr Asp
            20

<210> SEQ ID NO 117
<211> LENGTH: 20
<212> TYPE: PRT
<213> ORGANISM: Mycoplasma mycoides

<400> SEQUENCE: 117

Gln Gly Glu Arg Ala Met Ala Ala Asp Asn Lys Ser Leu Gly Gln Phe
1               5                   10

```
<210> SEQ ID NO 121
<211> LENGTH: 20
<212> TYPE: PRT
<213> ORGANISM: Homo sapiens

<400> SEQUENCE: 121

Asp Ile Asp Ala Asn Gly Ile Leu Asn Val Thr Ala Thr Asp Lys Ser
1               5                   10                  15

Thr Gly Lys Val
            20

<210> SEQ ID NO 122
<211> LENGTH: 20
<212> TYPE: PRT
<213> ORGANISM: Homo sapiens

<400> SEQUENCE: 122

Asp Ile Asp Ala Asn Gly Ile Leu Asn Val Thr Ala Ala Asp Lys Ser
1               5                   10                  15

Thr Gly Lys Glu
            20

<210> SEQ ID NO 123
<211> LENGTH: 20
<212> TYPE: PRT
<213> ORGANISM: Homo sapiens

<400> SEQUENCE: 123

Glu Ile Asp Val Asn Gly Ile Leu Arg Val Thr Ala Glu Asp Lys Gly
1               5                   10                  15

Thr Gly Asn Lys
            20

<210> SEQ ID NO 124
<211> LENGTH: 20
<212> TYPE: PRT
<213> ORGANISM: Homo sapiens

<400> SEQUENCE: 124

Asp Ile Asp Ala Asn Gly Ile Leu Ser Val Thr Ala Thr Asp Arg Ser
1               5                   10                  15

Thr Gly Lys Ala
            20

<210> SEQ ID NO 125
<211> LENGTH: 20
<212> TYPE: PRT
<213> ORGANISM: Homo sapiens

<400> SEQUENCE: 125

Asp Ile Asp Ala Asn Gly Ile Leu Asn Val Ser Ala Val Asp Lys Ser
1               5                   10                  15

Thr Gly Lys Glu
            20

<210> SEQ ID NO 126
<211> LENGTH: 20
<212> TYPE: PRT
<213> ORGANISM: Homo sapiens

<400> SEQUENCE: 126

Asp Ile Asp Ala Asn Gly Ile Val His Val Ser Ala Lys Asp Lys Gly
1               5                   10                  15
```

Thr Gly Arg Glu
        20

<210> SEQ ID NO 127
<211> LENGTH: 20
<212> TYPE: PRT
<213> ORGANISM: Arabidopsis thaliana

<400> SEQUENCE: 127

Asp Ile Asp Ala Asn Gly Ile Leu Asn Val Ser Ala Glu Asp Lys Thr
1               5                   10                  15

Thr Gly Gln Lys
        20

<210> SEQ ID NO 128
<211> LENGTH: 20
<212> TYPE: PRT
<213> ORGANISM: Saccharomyces cerevisiae

<400> SEQUENCE: 128

Asp Ile Asp Ala Asn Gly Ile Leu Asn Val Ser Ala Leu Glu Lys Gly
1               5                   10                  15

Thr Gly Lys Ser
        20

<210> SEQ ID NO 129
<211> LENGTH: 20
<212> TYPE: PRT
<213> ORGANISM: Saccharomyces cerevisiae

<400> SEQUENCE: 129

Glu Val Asp Ala Asn Gly Ile Leu Lys Val Thr Ala Val Glu Lys Ser
1               5                   10                  15

Thr Gly Lys Ser
        20

<210> SEQ ID NO 130
<211> LENGTH: 20
<212> TYPE: PRT
<213> ORGANISM: Bacillus halodurans

<400> SEQUENCE: 130

Asp Ile Asp Ala Asn Gly Ile Val Asn Val Lys Ala Lys Asp Leu Gly
1               5                   10                  15

Thr Asn Lys Glu
        20

<210> SEQ ID NO 131
<211> LENGTH: 20
<212> TYPE: PRT
<213> ORGANISM: Mycoplasma mycoides

<400> SEQUENCE: 131

Glu Ile Asp Ala Asn Gly Ile Val Ser Val Ser Ala Lys Asp Lys Asn
1               5                   10                  15

Thr Asn Glu Glu
        20

<210> SEQ ID NO 132
<211> LENGTH: 20
<212> TYPE: PRT
<213> ORGANISM: Mycobacterium tuberculosis -continued

```
<400> SEQUENCE: 132

Asp Ile Asp Ala Asn Gly Ile Val His Val Thr Ala Lys Asp Lys Gly
1               5                   10                  15

Thr Gly Lys Glu
            20
```

TREATMENT AND PREVENTION OF INFLAMMATORY DISEASES AND AUTOIMMUNE DISEASES

CROSS-REFERENCE TO RELATED APPLICATIONS

This application is a National Stage application of PCT/NL2008/050458, filed Jul. 7, 2008, which claims the benefit and priority of European Patent Application 07111898.8, filed Jul. 6, 2007 and European Patent Application 07118588.8, filed Oct. 16, 2007. The foregoing applications are incorporated by reference herein in their entirety.

FIELD OF THE INVENTION

The present invention relates to the treatment and/or prevention of inflammatory diseases, in particular Inflammatory Bowel Diseases (IBD), including Crohn's disease, granulomatous colitis, ulcerative colitis, lymphocyte colitis, collagenous colitis and Coeliac disease, as well as other inflammatory diseases such as allergic diseases or conditions, such as atopic dermatitis, food allergies, drug allergies and asthma. The invention furthermore relates to the treatment and/or prevention of arthritic diseases (especially rheumatoid arthritis and/or psoriatic arthritis and/or juvenile arthritis) and other autoimmune diseases, such as atherosclerosis, multiple sclerosis, or myasthenia gravis. Especially, the use of human MHC class II eluted fragments of heat shock protein 70 family members and their extended sequences (such as longer fragments and/or a panel of peptides), for the preparation of compositions for the treatment or prevention of IBD and arthritis and other autoimmune or inflammatory diseases is provided, as are methods for therapeutic and/or prophylactic treatment of IBD, arthritis and other autoimmune or inflammatory diseases. Also, specific HSP-70 protein derived peptides are provided herein. Further, a method for identifying and selecting peptides of heat shock protein 70 (HSP70) family members, suitable for the treatment and/or prevention of inflammatory or autoimmune diseases is provided.

BACKGROUND OF THE INVENTION

Heat shock proteins (HSP) have shown to be critical to protect against type 1 diabetes mellitus and rheumatoid arthritis, both of which are prevalent chronic degenerative autoimmune diseases.

The criticality was based on the following findings:
1. Peptides of HSP's can be used as therapeutic agents to prevent or arrest the inflammatory damage in both experimental autoimmune arthritis and in experimental autoimmune diabetes. The peptide treatments (in first clinical trials) are marked by a shift in the cytokine profiles of specific autoimmune T cells from a pro-inflammatory Th-1 response to an anti-inflammatory Th-2 response.
2. Epitopes of HSP's are recognised by the adaptive arm of the immune system (antigen receptors of T cells and B cells).
3. Epitopes of HSP's are targets for regulatory T-cells in both diseases.

In models of type I diabetes and arthritis, immunisation with HSP has been seen to prevent and to suppress disease. The probable mechanism here is the expansion of microbial (commensal) HSP reactive T cells, tolerized in the gut through mechanisms of mucosal tolerance. This expansion of HSP reactive T cells was possible through both oral and parenteral routes of HSP administration. The expanded T cells are cross-reactive with homologous self-HSP over-expressed in the inflamed (stressed) tissue. This cross-reactivity of tolerant T cells leads to regulatory cytokine production at the site of inflammation. For type I diabetes and arthritis, first clinical trials in humans have shown the potential of HSP derived peptides from HSP60 and HSP40 to switch cytokine patterns of disease associated T cell specificities into more regulatory cytokine production.

WO95/25744 describes the use of parts of mycobacterial heat shock proteins (HSP65) having mammalian sequence similarity for protection against or treatment of an inflammatory disease, including autoimmune diseases, such as diabetes, arthritic diseases, atherosclerosis, multiple sclerosis, myasthenia gravis, or inflammatory responses due to tumour or transplant rejection. The document only shows data for HSP65-derived epitopes (a HSP60 family member).

U.S. Pat. No. 6,007,821 describes the use of full length, human heat shock proteins HSP90 and HSP70 for the treatment of autoimmune diseases. Only data for using gp96 (a HSP90 member) to treat insulin dependent diabetes mellitus (IDDM) is provided. The effect is seen only after onset of IDDM and the autoimmune response (i.e. the abnormal immune response to self antigens) is said to be reversed by the treatment with full length human gp96. The heat shock proteins used in the therapeutic treatment in U.S. Pat. No. 6,007,821 are preferably obtained from the patients to be treated, i.e. the patient having developed the autoimmune disease (i.e. they are autologous proteins). There is no indication of the use of non-full-length HSP70 or HSP90 proteins and HSP70 peptides are only mentioned in the context of peptides being complexed with full lengths HSP70 protein. Prophylactic treatment is not included in this document. Erroneously, ulcerative colitis is mentioned as being an autoimmune disease.

Kingston et al. (1996, *Clin. Exp. Immunology* 103: 77) describe that full length recombinant Mycobacterial HSP70 protein can be used to reduce the development of adjuvant arthritis.

Tanaka et al. (1999, *J. Immunology* 163, 5560-5565) describe that peptide 234-252 of Mycobacterial HSP70 suppresses the development of adjuvant arthritis and induces IL-10 production. Epitope specific T cell lines also have a protective effect. Another peptide (amino acids 84-103) is not effective and does not suppress adjuvant arthritis development. Tanaka et al. suggest that the rat homolog of the Mycobacterial peptide 234-252 may also be suitable for protecting against arthritis, as the T cell line specific for the mycobacterial peptide responded in preliminary trials to the conserved rat peptide (which differs in 8 amino acids from the 19 amino acid long bacterial peptide).

Van Eden (2000, *Cell Stress and Chaperones* 5: 452-457) provides a review of the protective potential of self-heat shock proteins in arthritis immunization.

Wendling et al. (2000, *J. Immunology* 164: 2711-2717) tested a panel of overlapping synthetic 15-mer peptides of mycobacterial HSP70 for their ability to induce proliferation of a (full-length) recombinant mycobacterial HSP70-specific T-cell line. Using this approach 4 peptides were identified (amino acids 111-125, 131-145, 397-411 and 490-504). Of these four, peptide 111-125 induced T-cells cross-reactive to the rat homolog of peptide 111-125 (thus to self-HSP70), but parenteral pre-immunization with this mycobacterial peptide did not protect against arthritis development. Nasal administration, on the other hand did result in significant reduction of arthritis.

Dengjel, Schoor et al. (2005, PNAS USA 102: 7922-2927) describe experiments which show that fragments of HSP70 family members are loaded into Major Histo-compatibility Complex class II (MHC class II) molecules when human B cells are cultured under conditions of nutrient deprivation and that this occurs primarily for intracellular cytosolic proteins and not for extracellular proteins. This paper is silent about the use of such HSP fragments for induction of disease suppressive immune regulation.

Crotzer and Blum (2005, PNAS USA 102: 7779-7780) describe the molecular and cell biological basis of the HSP70 uploading of MHC class II and review the evidence that cell stress leads to mechanisms of autophagy and that especially HSP70 family member fragments are loaded into MHC class II molecules by the mechanisms of chaperone mediated autophagy (CMA). There is no mentioning of the possible induction of disease suppressive immune regulation.

Paludan et al. (2005, Science 307: 593-595) describe that lysosomal processing after autophagy contributes to MHC class II-restricted surveillance of long-lived endogenous antigens. In the added supplementary material (Supplemental Table 1) it is described that HSC70 and HSP70 are two of the three most frequent cytosolic/nuclear MHC class II natural ligand sources.

Mizushima, Yamamoto et al. (2004, Mol. Biol. Cell 15: 1101-1111) describe that autophagy is constitutively active and occurs without nutrient deprivation or other cell stress inducing events, in thymic epithelial reticular cells and that such thymic autophagy was more active in newborns. From this one can infer that autophagy contributes to development of T cell repertoire.

Hutszti, Bene et al. (2004, Inflamm. Res. 53: 551-555) describe experiments aimed at supporting the observation that low levels of antibodies against mycobacterial hsp65 are found in patients with IBD.

Elsaghier et al. (1992, Clin. Exp. Immunology 89: 305-309) describe the measurement of antibody levels to mycobacterial and human heat shock proteins in patients with Crohn's disease, ulcerative colitis and non-tuberculous mycobacterial diseases of the lung. They conclude that the data are not sufficient to imply sensitization with mycobacteria in patients with IBD. Thus, other bacterial proteins may be involved in sensitization.

WO 03/072598 describes the use of HSP70 peptides in the diagnosis and treatment of autoimmune disease, in particular type 1 diabetes. Of the diabetes patients tested, most showed proliferative response to eicosapeptides 1-20 (p1), 391-410 (p27) and 511-530 (p35) of the human HSP70. There is no disclosure of the peptides being suitable for use in immune interventions.

WO 2007/054658 discloses the use of certain CD40L and mycobacterial hsp70 sequences for use in the control of immune responses. The hsp70 sequences are the eicosapeptides 407-426, 457-476 and 477-496

There still remains a need for other peptides and compositions suitable for the treatment and/or prevention of IBD and arthritis and/or other autoimmune diseases.

There also remains a need for methods which can be used to identify or select peptides which, when administered in suitable amounts to humans, treat or prevent arthritis and/or other autoimmune diseases or symptoms thereof.

The origin of inflammatory bowel diseases (IBD) is known to depend on the presence of bacterial gut flora and is regarded as an inappropriate hyper-responsiveness to commensal organisms (Bouma and Strober 2003, Nature Rev. Immunol. 3: 521-533). In surgically excluded ileum of Crohn's patients (no fecal stream) lesions were seen to disappear. Infusion of intestinal contents induces recurrent Crohn's disease (D'Haens et al. 1998, Gastroenterology 114: 262-267). Moreover, under germ-free conditions no experimental IBD disease can be induced, unless the gut flora is reconstituted (Chandran et al. 2003, Surgeon 1:125-136, Strober et al. 2002, Ann. Rev. Immunol. 20: 495-549). Therefore, supposedly, bacterial antigens are the trigger leading to the induction of disease. In IBD such as Crohn's disease no causally related auto-antigens are known to exist, which is in contrast to auto-immune diseases. IBD are, therefore, considered not to be auto-immune diseases such rheumatoid arthritis is.

Models of IBD have generated evidence for a primary role of anaerobic bacteria (Clostridium, Bacteroides) in the induction of disease (see Verdu et al. 2000, Clin. Exp. Immunol. 120(1):46-50). Crude sonicates of anaerobic, aerobic gram positive and gram negative bacteria have been administered orally in DSS-induced colitis and only sonicates of anaerobic bacteria were found to reduce severity of experimental colitis.

SUMMARY OF THE INVENTION

The present inventors have found that one or more HSP70 derived peptides can be used for treating and/or preventing arthritis and/or other autoimmune diseases as well Inflammatory Bowel Diseases and other inflammatory diseases. The invention, therefore, relates to the peptides and mixtures thereof, as such, to compositions comprising one or more of these, as well as to methods for identifying protective HSP70 peptides which are capable of activating HSP70 specific regulatory T cells. Also provided are HSP70-peptide specific T cell lines and hybridomas, which can be used in vitro or in vivo as a source of HSP70-peptide specific regulatory T cells, for research purposes and for use of such specific regulatory T cells in treatment and therapy.

After immunizing mice with full length mycobacterial HSP70 protein and epitope mapping analysis, testing proliferation of T-cell responses in the presence of mycobacterial HSP70-derived peptides (in a screen with 123 overlapping HSP70 peptides, see Wendling et al. 2000, J. Immunol. 164: 2711-2717), thirteen mycobacterial 15-mer peptides were identified, which were recognized by mycobacterial HSP70 primed T-cells and were, thus, considered candidates for being involved in the activation of HSP-specific regulatory T-cells. Using a pooling strategy of the 13 peptides (divided into pools based on their homology to mouse homologue HSP70 peptides) in immunizing mice, they found that two of the conserved bacterial peptides (designated 'B1' and 'C1') induced T cells which were cross-reactive with the mouse homologue HSP70 peptides ('mB1' and 'mC1a', 'mC1b', respectively) i.e. the bacterial peptide-primed T cells cross-reacted with the homologous "self" HSP70 peptides of mouse (i.e. the mouse homologue peptides.

In subsequent experiments administering full lengths mycobacterial HSP70 protein or mycobacterial and/or mouse HSP70 peptides (e.g. a mixture of a mycobacterial peptide having amino acids VLRIVNEPTAAALAY (SEQ ID NO: 3) and designated "C1" and mouse homologue HSP70 peptide having amino acid sequence VLRVINEPTAAALAY (SEQ ID NO: 4) and designated "mC1a" or administration of either of these peptides as such; or administration of a mycobacterial peptide having amino acid sequence DEVVAV-GAALQAGVL (SEQ ID NO: 1) and designated peptide "B1" as such) prior to inducing arthritis in mice, the intranasal pre-treatment with the mixture of a bacterial and mammalian homologue HSP70 peptide or treatment with any of these peptides individually, or with the mycobacterial peptide B1, was able to significantly reduce arthritis progression and symptom severity, indicating that conserved HSP70 peptides can be used to treat and/or prevent arthritis.

Thus, bacterial HSP70-derived peptides are able to induce proliferation and expansion of specific protective T-cells, which are cross-reactive with "self" HSP70 epitopes (self HSP70 peptides), such as those derived from HSP70 proteins which are induced—locally—by the arthritic joints or arthritis inflamed regions. In addition to antigen-specific T cell proliferation, both IFN-gamma and IL10 production was significantly stimulated by the peptides and peptide mixture, indicating that the production of IFN-gamma and/or IL10 may play a role in the protective effect.

Furthermore, administering full length mycobacterial HSP70 protein or mycobacterial and/or mouse HSP70 peptides (C1 and mC1a), prior to inducing Colitis in mice, resulted in significant reduction of Colitis progression and symptom severity, indicating that full length HSP70 protein and/or conserved HSP70 peptides can be used to treat and/or prevent Inflammatory Bowel Diseases, such as Colitis. Thus, bacterial HSP70 protein and/or peptides are able to induce proliferation and expansion of specific protective T-cells, which are cross-reactive with "self" HSP70 epitopes (self HSP70 peptides), such as those derived from HSP70 proteins which are induced—locally—by the IBD.

The following peptides and/or mixtures thereof (and composition comprising these or consisting of these) were found to induce a HSP70 specific T-cell response and to be useful in methods for treating and/or preventing arthritis, especially rheumatoid arthritis and/or psoriatic arthritis and/or juvenile arthritis and/or other autoimmune diseases such as but not limited to type 1 diabetes, atherosclerosis, multiple sclerosis, myasthenia gravis or symptoms of any of these, as well as for treating and/or preventing of inflammatory diseases, in particular IBDs, such as Crohn's disease, granulomatous colitis, ulcerative colitis, lymphocyte colitis, collagenous colitis and Coeliac disease:

1) SEQ ID NO: 1—mycobacterial HSP70 peptide designated "B1" and having the amino acid sequence DEVVAVGAALQAGVL; and variants thereof (comprising e.g. at least 70% sequence identity to this peptide) and longer peptides comprising this peptide or the variants. A variant of SEQ ID NO: 1 is, for example, depicted in SEQ ID NO: 2, which shows the mouse HSP70 homologue peptide designated "mB1" and having the amino acid sequence DEAVAIGAAIQGGVL, and in the related parts of SEQ ID No: 83-93.

2) SEQ ID NO: 3—mycobacterial HSP70 peptide designated "C1" and having amino acid sequence VLRIVNEPTAAALAY; and variants thereof (comprising e.g. at least 70% sequence identity to this peptide) and longer peptides comprising this peptide or the variants. Variants of SEQ ID NO: 3 are for example depicted in the following two sequences: SEQ ID NO: 4, depicting the mouse HSP70 homologue peptide designated "mC1a" and having amino acid sequence VLRVINEPTAAALAY; and SEQ ID NO: 5 depicting the mouse HSP70 homologue peptide designated "mC1b" and having amino acid sequence VLRIINEPTAAAIAY, and in the related parts of SEQ ID No: 57-71.

Surprisingly, a peptide having the same amino acid sequence as peptide mC1b identified in the epitope mapping experiment by the inventors (see Examples) had been described in the literature to have been eluted from human MHC class II molecules from a human B cell line kept under stress (nutrient deprivation) conditions to augment autophagy (Dengjel et al. 2005, PNAS 102: 7922-7927, see Table 1, human peptide VLRIINEPTAAAIAY) and overlapping peptides had been described to be present in human MH class II by others (see Examples). The inventors hypothesized, without being bound by any theory, that therefore also other HSP70-derived peptides eluted from MHC class II molecules (and/or their bacterial homologues) are suitable for treating and/or preventing arthritis (especially rheumatoid arthritis and/or psoriatic arthritis and/or juvenile arthritis) and/or other autoimmune diseases such as but not limited to atherosclerosis, multiple sclerosis, myasthenia gravis or symptoms of any of these, as well as one or more IBD, such as Crohn's disease, granulomatous colitis, ulcerative colitis, lymphocyte colitis, collagenous colitis and/or Coeliac disease. Thus, a further group of peptides is provided which are useful according to the invention:

3) HSP70 protein derived peptides which bind the MHC class II on cells of the subject to be treated and which induce T cells that are cross-reactive with the homologous "self" HSP70 peptides of the subject.

Screening the literature for HSP70-derived peptides which are presented on (bind) MHC class II molecules (i.e. accommodated in the MHC class II cleft and which can be eluted therefrom), about 30 peptides were identified (see Examples and SEQ ID NO: 17-47), all of which are encompassed herein as being suitable for the treatment or prevention of autoimmune diseases and IBD's. Thus, in one embodiment of the invention compositions comprising one or more HSP70-derived peptides (and compositions comprising or consisting of these), which are capable of binding mammalian, especially human, MHC class II molecules, are provided herein for the activation of HSP70 specific regulatory T cells and, thus, for the treatment and/or prevention of arthritis, especially rheumatoid arthritis and/or psoriatic arthritis and/or juvenile arthritis and/or other autoimmune diseases such as but not limited to atherosclerosis, multiple sclerosis, myasthenia gravis or symptoms of any of these, as well as IBDs.

Also, a method of using one or more MHC class II-eluted peptides of HSP70 family members for (preparing a medicament for) the treatment or prevention of arthritis and/or other autoimmune diseases such as but not limited to atherosclerosis, multiple sclerosis, myasthenia gravis or symptoms of any of these is provided. Further, a method of using one or more longer HSP70 peptides, comprising these eluted peptides, is provided herein. In another embodiment the use of full length HSP70 protein or complexed HSP70-derived peptides is excluded herein (such as HSP70-peptide complexes as described in U.S. Pat. No. 6,007,821). Thus, preferably, the peptides used herein are free, uncomplexed peptides, which are not bound to other proteins or peptides. The use of peptides has the advantages that they can be made synthetically, which is cheap and avoids contamination of e.g. proteins purified from natural or recombinant sources. Also specificity, stability and homogeneity are high. Similarly, pharmaceutical, nutritional or food supplement compositions comprising one or more HSP70 peptides are provided, which can be used for immunizing or pre-immunizing mammals, especially humans, against arthritis and/or other autoimmune diseases, and/or for treatment of arthritis and/or other autoimmune diseases after onset of symptoms.

Also, a method of using one or more MHC class II-eluted peptides of HSP70 family members for the treatment or prevention of one or more IBDs is provided. In another embodiment a method of using a full length HSP70 protein for (preparing a medicament for) the treatment or prevention of one or more inflammatory bowel diseases (IBD) is provided herein. Similarly, the pharmaceutical, nutritional or food supplement compositions referred to above can be used for immunizing or pre-immunizing mammals, especially humans, against IBDs, and/or for treatment of IBDs after onset of symptoms.

In a further embodiment, a method for identifying HSP70-derived peptides suitable for the treatment and/or prevention of arthritis and/or other autoimmune diseases is provided, comprising:
a) providing one or more HSP70-derived peptides, preferably from a bacterial or mammalian HSP70 protein; and
b) optionally determining whether a HSP70-derived peptide is capable of binding MHC class II molecules, i.e. binding the MHC class II cleft, or being elutable from the MHC class II molecule;
c) optionally testing the capacity of the peptide to induce peptide specific T-cells which are cross-reactive with the homologous self-peptide of a mammal (especially a human or animal model or cell lines) in a cross-reactivity assay and selecting those peptides which do show cross-reactivity; and
d) administering a composition comprising or consisting of one or more of the peptides in an animal model of arthritis (such as adjuvant arthritis, proteoglycan induced arthritis) and/or to an animal model of another autoimmune disease, or in an animal model for of an inflammatory disease, in order to determine the in vivo protective activity, and comparing disease development and/or symptoms between treated and control animals, thereby verifying that the one or more peptides are suitable for treatment and/or prevention of the disease, and
e) using the one or more peptides for the preparation of a medicament for the treatment and/or prevention of arthritis and/or another autoimmune disease and/or an IBD in humans or animals and in a method for treating and/or preventing arthritis and/or another autoimmune disease and/or inflammatory disease in subjects, especially humans or domesticated animals, such as farm animals and companion animals (such as dogs).

Thus, in one embodiment, the peptide is derived from a HSP70 protein and comprises a T cell epitope that protects against experimentally induced arthritis and/or another autoimmune disease in model animals such as mice (see step d). In another embodiment, the peptide comprises or consists of part of the full HSP70 protein, or a panel of peptides of the full HSP70 protein, or a mixture of two or more HSP70 derived peptides and protects against experimental arthritis and/or another autoimmune disease and/or inflammatory disease when administered to mice (see step d).

Also a method for the treatment or prevention of arthritis and/or one or more other autoimmune diseases and/or one or more inflammatory diseases in a human or animal subject is provided, comprising administering to a subject in need thereof a therapeutically or prophylactically effective amount of one or more HSP70-derived peptides (or variants thereof, or longer peptides comprising the shorter peptides) (step (e)).

General Definitions

"Arthritis" refers herein to an inflammatory autoimmune diseases selected from rheumatoid arthritis, psoriatic arthritis and juvenile chronic arthritis.

"Autoimmune diseases" refers to diseases such as arthritis, insulin-dependent diabetes mellitus (type 1 diabetes), atherosclerosis, myasthenia gravis, experimental autoimmune encephalomyelitis, multiple sclerosis, etc. wherein the primary disease initiating and maintaining immune response is directed against auto-antigens (self antigens; i.e. antigens of normal cellular components) of the subject. Autoantibodies and T cells are produced, which are specific for such autoantigens. In particular, autoimmune diseases to be treated or prevented according to the invention, are those diseases which are caused by inflammatory T cells, i.e. MHC class II restricted CD4 T cells. These diseases include atherosclerosis, arthritis, myasthenia gravis, multiple sclerosis etc. These diseases can be considered as distinct from autoimmune disease which are caused by cytotoxic T lymphocytes (MHC class I restricted CD8 T cells), such as diabetes.

"Non autoimmune diseases" refers herein to diseases wherein the primary disease initiating and maintaining immune response is not directed against auto-antigens (self antigens) of the subject, but against non-self antigens (foreign antigens). For example, IBDs (Inflammatory Bowel Diseases) are non autoimmune diseases. In this/the latter case autoimmune responses are not responsible for initiating and/or maintaining the inflammation. In the case of Crohn's disease the non-autoimmune nature of the disease was demonstrated in surgically constructed blind-loops, where removal of fecal content led to resolution of the disease, whereas re-infusion of fecal contents led to disease recurrences (Rutgeerts et al. 1991, *Lancet* 338:771-774).

"Inflammatory disease" refers to any disease where tissue or cell damage or cell dysfunction is caused by the activity of the immune system in the form of plasma humoral mediators or lymphoid (white blood) cells. This includes inflammatory bowel diseases (IBD) and other inflammatory disease. Such other inflammatory diseases include allergic diseases or conditions, such as atopic dermatitis, food allergies, drug allergies and asthma.

"IBD" refers herein to Inflammatory Bowel Diseases, a chronic inflammation of the gastrointestinal tract, comprising or consisting of the following diseases: Crohn's disease, granulomatous colitis, ulcerative colitis, lymphocyte colitis, collagenous colitis and Coeliac disease.

"Subject(s)" are herein mammals, especially humans and/or domesticated animals, especially farm animals (cows, horses, pigs, etc.) or companion animals (dogs, cats, rabbits, etc.). The term 'model animal' usually refers herein to non-human animals, especially non-human mammals such as mice, rats, rabbits, etc.

The term "antigen" (or immunogen) includes reference to a substance capable of eliciting an adaptive immune response, i.e. to induce production of antigen recognition molecules (especially antigen-specific or cross-reactive T cells) to which the antigen is specifically immunoreactive. The specific immunoreactive sites within the antigen are known as "epitopes" (or antigenic determinants). Herein protein fragments (peptides) consisting of, or comprising, one or more epitopes of bacterial and/or mammalian HSP proteins capable of preventing and/or treating arthritis and/or one or more other autoimmune diseases are provided. These epitopes are also referred to as "protective epitopes".

"T cell epitope" refers to the epitopes recognized by the T cell receptors. Upon binding of the epitope, an immune response is mounted in the subject.

"Enteral" refers herein to the delivery directly into the gastrointestinal tract of a subject (e.g. orally or via a tube, catheter or stoma). "Nasal" refers to administration via the nose.

"Percentage" or "average" generally refers to percentages of averages by weight, unless otherwise specified or unless it is clear that another basis is meant.

"Sequence identity" and "sequence similarity" can be determined by alignment of two amino acid sequences or two nucleotide sequences using global or local alignment algorithms. Sequences may then be referred to as "substantially identical" or "essentially similar" or as "variants" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length, maximizing the number of matches and minimises the number of gaps. It is most suitable for aligning sequences of similar lengths. Generally, the GAP default parameters are used, with a gap creation penalty being higher than the extension penalty (e.g. gap opening penalty=10 and gap extension penalty=0.5). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA. Also, EmbossWin version 2.10.0 can be used, using the program 'needle' (which corresponds to GAP) with the same parameters as for GAP above. For sequences of different lengths preferably local alignment algorithms such as the Smith Waterman algorithm are used, such as provided by the program 'water' of e.g. EmbossWin version 2.10.0, using default parameters (gap opening penalty of 10.0 and a gap extension penalty of 0.5) or programs such as BLAST or FASTA.

The terms "protein" or "polypeptide" or "peptide" are used interchangeably and refer to molecules consisting of a chain of amino acids, without reference to a specific mode of action, size, 3 dimensional structure or origin. A "fragment" or "portion" of a protein, or a peptide comprising a fragment of a natural protein, may thus still be referred to as a "protein" or "peptide". An "isolated protein" is used to refer to a protein which is no longer in its natural environment, for example in vitro or in a recombinant bacterial host cell.

Depending on the context, the term "homologue" or "homologous" refers to sequences which are descendent from a common ancestral sequence. If desired, the term can be specified by referring to orthologs and paralogs; see http://www.ncbi.nlm.nih.gov/Education/BLASTinfo/Orthology.html). Orthologs generally retain the same function in a different species. Paralogs, in contrast evolved different (possibly related) functions. Bacterial heat shock proteins and mammalian heat shock proteins of the HSP70 family are, thus, herein referred to as homologues, as are HSP70 proteins of different species of bacteria or of different species of mammals (e.g. mouse and human HSP70 proteins). A "mammalian homologue" of a bacterial HSP70-derived peptide, will therefore be at least 70%, preferably at least 80%, 90% or more identical in amino acid sequence to the bacterial peptide, when aligned pairwise using e.g. a local alignment algorithm (e.g. Smith Waterman).

The terms "homologous" and "heterologous" may also be used to refer to the relationship between a nucleic acid or amino acid sequence and its host cell or organism, especially in the context of transgenic cells/organisms. A homologous sequence is thus naturally found in the host species, while a heterologous sequence is not naturally found in the host cell.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989, Molecular Cloning: a laboratory manual. 2nd ed. N.Y., Cold Spring Harbor Laboratory, Cold Spring Harbor Laboratory Press, 1989. 1659 p. ISBN 0-87969-309-6) and Sambrook and Russell (2001, Molecular Cloning: A Laboratory Manual, Third Edition, Cold Spring Harbor Laboratory Press, NY).

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a cell" refers also to several cells in the form of cell cultures, tissues, whole organism, etc. It is further understood that, when referring to "sequences" herein, generally the actual physical molecules with a certain sequence of subunits (e.g. amino acids) are referred to.

DETAILED DESCRIPTION

The invention pertains to the use of one or more heat shock protein 70 (HSP70) derived peptides eluted from and/or capable of binding to MHC class II molecules for the treatment and/or prevention of arthritis, especially rheumatoid arthritis and/or psoriatic arthritis and/or juvenile arthritis and/or other autoimmune diseases such as but not limited to atherosclerosis, multiple sclerosis, myasthenia gravis or symptoms of any of these. The invention further relates to compositions comprising or consisting of one or more of such peptides. The invention furthermore pertains to the use of the HSP70-derived peptides and/or to one or more full length HSP70 proteins, for the treatment and/or prevention of inflammatory diseases, in particular IBD, especially various forms of Colitis, such as those selected from the group consisting of Crohn's disease, Granulomatous Colitis, Ulcerative Colitis, Lymphocyte Colitis, Collagenous Colitis and Coeliac disease.

Peptides and Proteins for Use According to the Invention

Heat shock proteins are universal proteins, which carry out important housekeeping functions of prokaryotic and eukaryotic cells. They play an important role as chaperones in protein folding and in rescuing the cell from stress conditions. They are classified into different families on the basis of their monomeric molecular weight. Thus proteins of the family HSP70 have a molecular weight of about 70 kDa. The main families are HSP 10, 40, 60, 70, 90 and 100. Many mammalian HSP family members have highly conserved microbial homologues.

The inventors found that peptide fragments of mycobacterial HSP70 and of mammalian HSP70 proteins can be used to treat inflammatory diseases and/or autoimmune diseases in mammals. They found that the human homologue of one of the identified mouse peptides (designated mC1b) had been described in the paper of Dengjel et al. (PNAS 2005, supra) as being presented on MHC class II molecules. In the paper it is shown and argued that cytosolic proteins, especially under conditions of cell stress, are routed into the MHC class II pathway of antigen presentation through autophagy. In autophagy three distinct mechanisms are operative of which chaperone mediated autophagy (CMA) is one mechanism. In CMA HSC70 is a transporter molecule which assists Lamp-2 in its function to transfer cytosolic proteins into the lysosome for MHC class II presentation. Due to this mechanism of CMA, HSC70 (HSP70 family of proteins) fragments are preferentially intersecting with the MHC class II loading compartment and are captured in the MHC class II binding cleft. In the Dengjel et al. paper HSP70 peptides are found to dominate the cytosolic peptide repertoire that is retrieved from MHC class II and are upregulated under conditions that augment autophagy (nutrient starvation). Nowhere in the paper there is any interpretation of what this could mean for HSP specific CD4+ T cell recognition, but having found that similar peptides (designated herein mC1a and C1) are suitable for treatment and/or prevention of autoimmune diseases such as for example arthritis or IBD, the inventors concluded that HSP70-derived peptides which are capable of being bound to MHC class II molecules and which induce CD4+ T-cells that are cross-reactive to the homologous "self" HSP70 peptide can be used to treat and/or prevent arthritis and/or other autoimmune diseases and/or IBD in mammals, especially humans. The term "treatment" refers herein to any reduction or alleviation of disease symptoms and/or progression, after administration of a suitable amount of one or more HSP70-derived peptides, whereby the administration takes place one or more times after arthritis or IBD has been diagnosed. This term encompasses thus a reduction in disease symptoms and/or progression in the treated subject (relative to the untreated subject), as well as a complete healing of the subject. The term "prevention" refers to the prophylactic administration of compounds or compositions according to the invention to subjects which have not yet been diagnosed with arthritis or IBD, but which may, for example, be at risk of developing disease.

The inventors were also guided by the paper of Mizushima et al. (Molecular Biology of the Cell, 2004, Vol. 15: 1101-1111) where it is shown that autophagy takes place at high basal levels in the thymus in the thymic epithelium cells. Younger mammals, and late-stage embryos show even higher autophagy activity in the thymus (ibid, same paper). The inventors reasoned that thymic epithelium cells are involved with positive selection of the T cell repertoire. This would open the possibility that HSP70 becomes uploaded in MHC class II at the location where, and at the time when, positive selection of the T cell repertoire is organised. In other words, from this the inventors inferred that thymic selected HSP70 derived peptides would possibly lead to the formation of a T cell repertoire of regulatory T cells with specificity for HSP70 peptides.

The present inventors have combined these pieces of information with their own experimental data (see Examples) in concluding that HSP70 family members derived peptides in the binding cleft of MHC class II molecules of cell lines subjected to conditions of raised autophagy, such as stress and nutrient deprivation, have the quality of inducing regulatory T cell responses and are suitable for the treatment and/or prevention of arthritis (especially rheumatoid arthritis and/or psoriatic arthritis and/or juvenile arthritis) and/or other autoimmune diseases such as but not limited to type 1 diabetes, atherosclerosis, multiple sclerosis, myasthenia gravis or symptoms of any of these or IBD.

The inventors have tested the mycobacterial HSP70 derived peptide designated C1 (SEQ ID NO: 3), and the cross-reactive mammalian (mouse) homologue thereof (the HSP70 homologue peptide designated mC1a, SEQ ID NO: 4), separately or mixed together, for their capacity to induce regulatory T cell responses (to the homologous mouse HSP70 peptide) in the model of proteoglycan induced arthritis in Balb/c mice. The experiments showed that nasal administration of both peptides alone (or as a mixture of both) suppressed arthritis when administered prior to induction of disease (see Examples). Similar results were also found for peptide "B1".

They also tested C1 for its capacity to induce regulatory T cell responses (to the homologous mouse HSP70 peptide) in the model of TNBS induced colitis in Balb/c mice. The experiment showed that nasal administration of this peptide (peptide mixture) suppressed TNBS induced colitis disease when administered after TNBS skin sensitization and prior to induction of disease by rectal TNBS administration (see Examples).

The inventors have also tested the complete mycobacterial HSP70 molecule in models of experimental IBD. In this case the mycobacterial HSP70 of SEQ ID NO: 55 was tested. For this purpose both the models of TNBS induced IBD and the model of DSS induced IBD were used. In both models the full lengths mycobacterial HSP70 protein, when administered orally and/or nasally, inhibited disease development.

Thus, the present inventors found that nasal and/or oral administration of HSP70 derived peptides and/or complete HSP70 protein in the rodent TNBS and DSS models of colitis is highly disease suppressive (see Examples). Both a prophylactic effect and a treatment effect was observed.

The (nasally administered) effect of the peptides on preventing arthritis was comparable to the protective effect of (nasally administered) full length mycobacterial HSP70 protein (SEQ ID NO: 55). Thus, the inventors found that nasal administration of HSP70 derived peptides in the rodent arthritis model is highly disease suppressive (see Examples).

Thus, in one embodiment a protective epitope or protein fragment (peptide) consisting of or comprising protective epitopes are provided, as are compositions comprising one or more of these. Especially in one embodiment one or more HSP70 peptides, or longer polypeptides comprising such a peptide, are provided for the preparation of a compositions (e.g. a medicament or vaccine) for the treatment and/or prophylaxis of arthritis and/or other autoimmune diseases and/or IBD. Also a panel of HSP70 peptides is provided, whereby a panel includes overlapping peptides, which together cover the full length HSP70 protein. A subpart or all of such a panel may also be used to prepare compositions according to the invention.

The term "HSP70 protein" refers herein to full length proteins such as full length HSP70 proteins of human, animal (e.g. mammalian), bacterial, yeast, plant or other origin and having been classified as belonging to the HSP70 family of proteins. The term also includes "variants" of such proteins, such as proteins having one or more amino acids deleted, replaced or inserted relative to the native protein. Variants may comprise at least 50%, 60%, 70%, 80%, 85%, 90%, 95%, 98% or 99% or more amino acid identity to the native protein (i.e. the HSP70 protein found in nature in the organism), when aligned over the entire length, using preferably a global alignment algorithm. Examples of HSP70 proteins include the Mycobacterial HSP70 protein depicted in SEQ ID NO: 55 and variants thereof, the human HSP70 proteins depicted in SEQ ID NOs: 48-54 and variants thereof, such as proteins comprising at least the above % amino acid sequence identity to SEQ ID NOs: 55 and/or 48-54. HSP70 proteins from other sources are well-known in the art and their amino acid sequences are readily available, e.g. through http://www.expasy.org. Examples include (with UniProtKB/Swiss-Prot entries): bovine HSP70 protein 8 (P19120; HSP7C_BOVIN); murine HSP protein 5 (P20029; GRP78_MOUSE); rat HSP protein 9 (P48721; GRP75_RAT); chicken (P08106; HSP70_CHICK); fruit fly (*Drosophila melanogaster*) (HSP72_DROME); *Arabidopsis thaliana* (P22953, HSP71_ARATH; P22954, HSP72_ARATH; O95719, HSP73_ARATH; Q39043, BIP2_ARATH); *Nicotiana tabacum* (Q40511_TOBAC; Q67BD0_TOBAC; Q67BD1_TOBAC; Q67BD2_TOBAC; Q03685, BIP5_TOBAC); *Saccharomyces cerevisiae* SSQ1 (Q05931, HSP7Q_YEAST), SSB2 (P40150, HSP76 YEAST), SSA3 (P09435, HSP73_YEAST) and SSA4 (P22202, HSP74_YEAST); *Lactobacillus acidophilus* (Q84BU4, DNAK_LACAC); *Mycoplasma mycoides* (Q6MT06; DNAK_MYCMS); and *Mycobacterium leprae* (DNAK_MYCLE, P19993), *M. avium* (A0QLZ6, DNAK_MYCA1), *M. paratuberculosis* (Q00488, DNAK_MYCPA), and *M. gilvum* (DNAK_MYCGI, A4T112); etc.

The term "HSP70 derived peptide" or "HSP70 peptide" or "HSP70 fragment" refers herein to fragments of the above described HSP70 proteins and/or protein variants, such as fragments comprising or consisting of at least 5, 6, 7, 8, 9, 10, preferably at least 11, 12, 13, 14, 15, optionally at least 16, 17, 18, 19, 20, 25, 30, 40, 50, 60, 70 or more consecutive amino acids of a HSP70 protein or variant as defined above. Thus, when aligned with a full length HSP70 protein or variant (as defined above) using a local alignment algorithm the at least 5, 6, 7, 8, 9, 10, 11, etc. consecutive amino acids of the peptide will match the full lengths protein or variant by 100%. A HSP70 derived peptide may further comprise additional amino acids e.g. at one or both ends, or inserted between amino acids. These further amino acids need not necessarily be complementary to the natural HSP70 amino acid sequence. The variability in length reflects the fact that different lengths variants can bind the MHC class II molecules. Non-limiting examples of HSP70 derived peptides according to the invention consist of, or comprise, SEQ ID NO: 1-5, or variants thereof, such as peptides which comprise 1, 2, 3, 4, 5, 6, 7, 8, 9 or 10 amino acid insertions or additions, replacements or deletions with respect to SEQ ID NO: 1-5 and which are still protective in vivo. Other preferred peptides are peptides consisting or, or comprising, SEQ ID NO: 17-47, or variants thereof, such as peptides which comprise 1, 2, 3, 4, 5 or more amino acid insertions or additions, replacements or deletions with respect to SEQ ID NO: 17-47 and which are still protective in vivo. Especially preferred peptides are those of SEQ ID NO: 56-132, i.e. an identical part thereof or an equivalent having at least 70%, preferably at least 80%, more preferably at least 90% amino acid identity with such a part. Obviously, the HSP70 peptides according to the invention are functional in vivo in treating and/or preventing arthritis, and functionality can be tested or determined as explained further below. In one embodiment, the peptides comprise or consist of no more than 30, 25, 20, 19, 18, 17, 16, 15, 14, 13, 12, 11 or 10 contiguous amino acids of a HSP70 protein or variant. Preferably the peptides to be used in the invention have at least 10, 11, 12, 13 or 14 amino acids, up to 19, 18, 17 or 16 contiguous amino acids. Most preferably the peptides have at least 11 to 30, more preferably at least 12 amino acids, up to less than 25 amino acids, most preferably from 15 to less than 19 amino acids.

A "panel" of HSP70 peptides refers to a collection of at least two, three, four, five, and so forth, up to at least 50, 100, 120, 130, 150, 200, 300 or more peptides which overlap by one or more amino acids (preferably at least by 3, 5, 8, 9, 10, 11 amino acids or more), so that the entire HSP70 protein is covered by the collection, i.e. alignment of the overlapping regions could reconstitute the entire HSP70 protein or protein variant. For example, a panel of 15-mer peptides which overlap by 10 amino acids results in a panel of 123 peptides. The panel of peptides will be smaller or larger with different peptide length and/or overlap. A subpanel will cover less than the entire HSP70 protein, such as at most 80%, 60%, 50%, 30%, 20% or less.

In principle, any HSP70 protein fragment may be used, such as any HSP70 protein fragment of a microbial (e.g. bacterial, such as from *Mycobacterium*, etc.) or a mammalian (e.g. rat, mouse, human etc.) origin. HSP70 proteins of a wide variety of organisms have been cloned and sequenced, as described above, and proteins and/or peptides can thus be produced by e.g. recombinant DNA techniques, synthesized chemically or be purified from natural sources using methods well known in the art. HSP70-derived peptides may be fragments of HSP70 proteins of any origin, e.g. bacterial, yeast, plant, synthetic, artificial, mammalian (rat, mouse, bovine, etc.) or human. When using full length HSP70 proteins (or a panel of peptides, e.g. covering the full length protein), it is one embodiment that the full length protein is not of human origin, especially when it is used for the treatment and/or prevention of ulcerative colitis. This embodiment, thus, comprises the use of full-length non-human HSP70 protein for the treatment or prevention of ulcerative colitis.

Preferably the HSP70 protein panel and/or HSP70 peptides comprise or consist of epitopes which are functional in vivo, i.e. they prevent or treat arthritis and/or other autoimmune diseases when administered in suitable concentrations and by a suitable route (such as intra-nasal). Such peptides are preferably capable of a) binding the MHC class II molecules of a subject (e.g. human), and, optionally (b) they are capable of activating regulatory T-cells (CD4+ cells) which are cross-reactive with the homologous "self" HSP70-peptide of the subject (e.g. human or animal) or of a mammalian model animal, such as mouse and (c) when administered to an animal or human subject the peptide(s) is/are able to treat and/or prevent arthritis and/or one or more other autoimmune diseases, or symptom severity and/or development (progression) of any of these. The above capabilities of the peptides can be tested as described in detail elsewhere herein, but basically capability a) can be determined by either identifying peptides from the scientific literature, which have been described to have this capability and/or by MHC class II binding assays in vitro or in vivo; capability b) can be tested by in vitro priming and capability c) can be tested by using e.g. animal models and/or in human trials. In animal models also humanised MHC transgenic animals can be used.

Thus, in one embodiment a peptide having a specific amino acid sequence is used as such, e.g. the composition comprises or consists of a plurality of molecules of one of SEQ ID NO: 1-5 and 10, or SEQ ID NO: 17-47 and/or 56-132, or other individual HSP70-derived peptides.

In another embodiment a mixture of two or more different HSP70-derived peptides are provided. These different peptides may be from the same HSP70 protein (e.g. derived from a bacterial HSP70, e.g. from mycobacterial HSP70, such as SEQ ID NO: 55) or from different HSP70 proteins, such as from homologues of different species, e.g. one peptide being from mouse or human HSP70 and one peptide being from bacterial HSP70. "Different" implies that the amino acid sequence of the peptides differs by at least one amino acid (by addition, replacement or deletion relative to the other peptide).

Also mixtures of one or more HSP70 peptides and/or a HSP70 panel may be used. In a preferred embodiment, a composition for the treatment and/or prevention of arthritis and/or other autoimmune diseases comprises or consists of at least one microbial and at least one a mammalian HSP70 peptide, whereby the bacterial and the mammalian peptide are preferably homologues of one another, i.e. they are very similar in their amino acid sequence (they are "variants" as defined above) and cross-reactive. For example, a preferred composition comprises peptides of SEQ ID NO: 3 (bacterial 'C1') and one or more of the mouse homologues (SEQ ID NO: 4 and/or 5, or other variants thereof, such as from other species, see SEQ ID NO: 47-54 and 56-132).

When referring to "a heat shock protein" it is understood that the protein occurs in bacteria, yeast, plant or mammalian cells in nature, but may be produced or isolated by various means. For example, it may be produced by recombinant DNA technology, whereby the nucleotide sequence encoding the protein (or protein fragment) is used to transform or transfect a host cell, which then produces the protein or protein fragment. Nucleic acid sequences (cDNA, RNA and genomic DNA) encoding HSPs are available in the art or may be made by chemical synthesis, and the methods for recombinant production of the protein or protein fragment (peptide) are routine. Similarly, nucleic acid hybridization techniques (for example using stringent hybridization conditions) may be used to isolate genes encoding HSPs. Alternatively, the protein or protein fragment may be purified or partially purified from natural sources (e.g. mammalian cells, bacteria or plants) or may be synthesized chemically. For example, the peptides can be synthesised by the well-known Merrifield solid-phase synthesis method in which amino acids are sequentially added to a growing chain. See Merrifield (1963), J. Am. Chem. Soc. 85:2149-2156; and Atherton et al., "Solid Phase Peptide Synthesis," IRL Press, London, (1989). Automatic peptide synthesisers are commercially available from numerous suppliers, such as Applied Biosystems, Foster City, Calif.

In the broadest sense, any HSP70 peptide sequences that have the capacity to bind MHC class II molecules of a subject is provided. This capacity can be tested using various methods known in the art. For example, a complete overlapping set of e.g. 15-mer peptides covering the whole HSP70 protein can be tested in MHC class II binding assays, see Peptide electrophoretic mobility shift assay, Mittelman A. et al., Degenerate binding of tyrosinase peptides to MHC II Ad/Ed molecules. *J. Exp. Ther. Oncol.* (2007) 6:231-9. See also competition based binding assay, described by Joosten, I. et al. (1994). Direct binding of autoimmune disease related T cell epitopes to purified Lewis rat MHC class II molecules. *Int. Immunol.* 6:751. See also US2004/224009. Preferably, such methods are used to test whether one or more peptides are capable of binding to MHC class II molecules.

"Fragments" refer herein to peptides comprising at least 6 or 7, more preferably at least 8 or 9, more preferably 10, 11, 12, 13, 14, 15, optionally 16, 17, 18, or more consecutive (contiguous) amino acids of any of the HSP70 protein. As already mentioned, this is relevant especially because MHC class II binding peptides have varying lengths and multiple length variants can bind similar MHC class II molecules. In one embodiment a fragment is not longer than 40, 30, preferably 25, 20, 19, 18, 17, 16 or 15 amino acids.

The HSP70 fragments (and mixtures) according to the invention are preferably "functional", i.e. they consist of or comprise one or more peptide sequences that have the capacity to treat and/or prevent arthritis and/or one or more other autoimmune diseases and/or IBD when administered in vivo. Thus, ultimately, in vivo animal models of arthritis and/or of another autoimmune disease should be used to test functionality as described in the Examples and as known in the art.

The peptides preferably are able to bind MHC class II molecules of a subject (see above). Although not all HSP70-derived peptides, which are able to bind MHC class II molecules, will be able to induce protective T cell responses, a pre-selection of potentially functional HSP70-derived peptides (T cell epitopes) can be made by selecting HSP70 sequences that are found in the clefts of MHC class II molecules, knowing that roughly 50% of MHC bound sequences will be utilised as T cell epitopes by the immune repertoire. Following this pre-selection based on MHC class II binding capacity, the functionality can then be further tested by testing the ability of the peptide(s) to induce T-cells (like with an in vitro human T-cell sensitization assay, e.g. see: page 3239 RH Column "Cellular Assay" and page 3243 LH column in Halder T, et al., Isolation of novel HLA-DR restricted potential tumor-associated antigens from the melanoma cell line FM3., *Cancer Res.*, 1997, 57:3238-44) and which are cross-reactive with homologous "self" peptides by analyzing them in the in vitro sensitization assay, and/or by testing the in vivo functionality in an animal model, whereby test animals are administered with potentially protective peptides and those peptides which significantly reduce or prevent the autoimmune disease (compared to suitable controls) in the animals are selected.

To test cross-reactivity, i.e. the capacity of selected peptides to induce T cells cross-reactive with homologous self-proteins, the following method can be used (see also Examples): T cells activated in vitro with the defined (e.g. microbial) HSP70 epitopes, can then be restimulated with the homologous self peptide (in the mouse model the mouse HSP), either as a recombinant protein or purified from stressed cells or tissue or as elevated levels of MHC-peptide complexes on stressed antigen presenting cells, or synthetically prepared. Any sign of activation (see above) can be taken as an indication of cross-reactivity of the test (e.g. microbial) epitope with the self protein/peptide. Initial testing can be carried out with a synthetic peptide based on the sequence of the self protein/peptide, but final proof for cross-reactivity with the protein/peptide itself, either in isolated form or expressed on cells, is preferably obtained in T cell activation tests with (stressed) antigen presenting cells (over) expressing and presenting the self HSP-peptide, in order to exclude cryptic epitopes.

An easy way of determining the most suitable fragment is to generate overlapping peptides (for example overlapping pentamers, hexamers, heptamers, or decamers; i.e. short consecutive amino acids) of a full length bacterial HSP protein or mammalian/human HSP protein and to screen these overlapping peptides for their protective effect. For example, by administration in a rodent model of an autoimmune disease such as arthritis, as described in the Examples.

In one embodiment a panel of peptides covering a complete HSP70 protein is used, as defined above, or a sub-panel. For example the mycobacterial HSP70 (SEQ ID NO: 55) consists of 625 amino acids in length. Fragments thereof, or of a variant thereof can be used. In another preferred embodiment a fragment comprising or consisting of at least about 6, 7, 8 or more consecutive amino acids of SEQ ID NO: 55, or a variant thereof, is used, for example SEQ ID NO: 1-5, or variants thereof. Also, a complete, preferably non-human HSP70 may be used, e.g. for the prevention or treatment of ulcerative colitis.

In yet another embodiment according to the invention, fragments (or panels) of HSP proteins for use according to the invention comprise all functional fragments derived from proteins having at least 35%, 40%, 45%, 50%, 60%, 70%, 80%, 90%, 95%, 98%, 99% or more (100%) amino acid sequence identity (over the full length of the protein) to any one of SEQ ID NO: 55 or 48-54 (also referred to as "variants" of SEQ ID NO: 55, or 48-54), irrespective of the origin of the protein and irrespective of whether it occurs naturally (in nature).

In these embodiments, it is not required that the protein occurs naturally in bacteria or mammals (e.g. humans), as herein variants of the naturally occurring HSP protein are used. Such variants may, of course, also occur naturally in bacteria or mammals. These variants (and fragments thereof) may be generated by methods known in the art, such as site directed mutagenesis, de novo chemical synthesis, recombinant expression of nucleic acid sequences comprising deletions, replacements, or additions of one or more nucleotides, gene shuffling techniques, etc. For example small modifications to a DNA sequence such as described above can be routinely made, i.e., by PCR-mediated mutagenesis (Ho et al., 1989, Gene 77, 51-59, White et al., 1989, Trends in Genet. 5, 185-189). More profound modifications to a DNA sequence can be routinely done by de novo DNA synthesis of a desired coding region using available techniques.

Preferred fragments of the bacterial HSP70 (as depicted in SEQ ID NO: 55) consist of or comprise the following amino acids:

amino acid 141-155 of SEQ ID NO: 55 (which is also depicted as SEQ ID NO: 3) and variants thereof;
amino acids 342-356 of SEQ ID NO: 55 (also depicted in SEQ ID NO: 1) and variants thereof;
bacterial homologues of SEQ ID NO: 17-47 (mammalian HSP70 fragments), or variants thereof; examples of such bacterial sequences are given in SEQ ID NO: 56-132;
any other fragment of at least 6, 7, 8, 9, 10, preferably at least 11, 12, 13, 14, 15, optionally at least 16, 17, 18, 20, 30, 40, 50 or more, consecutive amino acids of SEQ ID NO: 55 or variants thereof. Most preferred are fragments which are highly conserved among HSP70 proteins;
'variants' include homologues having at least 70 or at least 80% sequence homology; variants also include peptides having the sequence of SEQ ID NO: 3 or 1, wherein one or more, preferably up to five or more preferably one, two or three amino acids have been exchanged with the corresponding amino acids of SEQ ID NO: 56-71, or SEQ ID NO: 83-93, respectively.

Preferred fragments of mammalian homologue HSP70 proteins from e.g. mouse, rat, rabbit, bovine, human, etc. sources (e.g. as depicted in SEQ ID NO: 48-54 for human HSP70 proteins) consist of, or comprise the following amino acids:

mammalian homologues of SEQ ID NO: 1, such as for example SEQ ID NO: 2 (mouse homologues); or amino acids 366-380 of SEQ ID NO: 48 (human homologue hspa1a), or amino acids 368-382 of SEQ ID NO: 49 (human homologue hspa1l); amino acids 369-383 of SEQ ID NO: 50 (human homologue hspa2); amino acids 391-405 of SEQ ID NO: 51 (human homologue hspa5); amino acids 368-382 of SEQ ID NO: 52 (human homologue hspa6); amino acids 366-380 of SEQ ID NO: 53 (human homologue hspa8); amino acids 414-428 of SEQ ID NO: 54 (human homologue hspa9), or homologues of other mammalian HSP70 proteins or variants, such as sequences comprising at least 70% amino acid identity to SEQ ID NO: 1, or more (as defined above).

mammalian homologues of SEQ ID NO: 3, such as for example SEQ ID NO: 4 or 5 (mouse homologues); or amino acids 168-183 of SEQ ID NO: 48 (human homologue hspa1a), or amino acids 171-185 of SEQ ID NO: 49 (human homologue hspa1l); amino acids 170-184 of SEQ ID NO: 50 (human homologue hspa2); amino acids 195-209 of SEQ ID NO: 51 (human homologue hspa5); amino acids 171-185 of SEQ ID NO: 52 (human homologue hspa6); amino acids 169-183 of SEQ ID NO: 53 (human homologue hspa8); amino acids 216-230 of SEQ ID NO: 54 (human homologue hspa9), or homologues of other mammalian HSP70 proteins or variants, such as sequences comprising at least 70% amino acid identity to SEQ ID NO: 3, or more (as defined above).

amino acids or any other fragment of at least 6, 7, 8, 9, 10, 11, 12, 13, 14, 15, 16, 17, 18, 20, 30, 40, 50 or more, consecutive amino acids of any one of SEQ ID NO: 48-54 or variants thereof (such as homologues from other mammals). Most preferred are fragments which are highly conserved among HSP70 proteins.

SEQ ID NO: 17-47 and 56-132, or variants thereof, such as homologues thereof from other mammalian species or other mammalian HSP70 proteins 'variants' include homologues having at least 70 or at least 80% sequence homology; variants also include peptides having the sequence of SEQ ID NO: 4 or 5; or 2, wherein one or more, preferably up to five or more preferably one, two or three amino acids have been exchanged with the corresponding amino acids of SEQ ID NO: 56-72, or SEQ ID NO: 83-94, respectively.

In one embodiment it is preferred that only one protein fragment is used, while in another embodiment mixtures of protein fragments of different amino acid sequence may be used. Also, the whole HSP70 panel or sub-panel may be mixed or combined with one or more fragments of a HSP70 protein. Alternatively fragments of different HSP70 proteins may be mixed. For example, a HSP70 peptide from a bacterium may be mixed/combined or co-administered with one or more specific mammalian HSP70-derived peptides. Thus, also bacterial and mammalian functional fragments thereof, may be mixed. Equally mixtures of HSP70 derived fragments, of the same or different HSP70 protein, may be mixed. Mixtures comprise both single compositions, which comprise the two or more proteins and/or peptides or, alternatively, separate compositions (referred to as kits) which are co-administered (together, or one shortly after the other), so that only after administration the two or more proteins and/or fragments are combined in vivo, in one subject.

The mixture or kit may also comprise a panel of HSP70 peptides, or part of such a panel (sub-panel). For example, at least 3, 4, 5, or more overlapping peptides of each e.g. 10, 12, 15, 16 or more amino acids in length, which together could reconstitute at least part or even the full HSP70 protein, can be used together in one composition or co-administered so that they are combined in vivo. In case only part of the HSP70 protein is encompassed by the panel, it is preferred that the overlapping peptides make up at least 10, 20 or 25%, preferably at least 30, 40 or 50% of the full HSP70 protein. Also, preferably the peptides preferably overlap to form one or two contigs only. Thus, they may be from two regions of the full lengths protein, e.g. from the region including amino acid 150 of SEQ ID NO: 55 and including amino acid 350 of SEQ ID NO: 55. The peptides preferably overlap by at least one amino acid, more preferably by at least 2, 3, 4, or 5 amino acids.

In yet another embodiment of the invention protective epitopes or protein fragments consisting of or comprising protective epitopes are provided, whereby mammalian, such as mouse or human HSP70 derived peptides are used to prepare compositions (or medicaments) for the treatment and/or prophylaxis of arthritis and/or other autoimmune diseases in humans or animals, such as farm animals or companion animals. "Human heat shock 70 proteins" refer to proteins occurring naturally in *Homo sapiens*, such as those depicted in SEQ ID NO 48-54. Non-human, mammalian heat shock 70 proteins are variants of the human ones, comprising at least 50%, 60%, 70%, 80%, 90%, 95%, 98% or more identity to the human proteins (see definition elsewhere herein). Throughout the description, the embodiments described for bacterial HSP70-derived fragments apply equally to mammalian, especially mouse and human HSP70-derived fragments and vice versa.

Thus, in one embodiment thus also full length human HSP70 protein (or variants or a panel of peptides) may be used to treat human (or animal) subjects, especially to treat or prevent one or more IBDs selected from Crohn's disease, granulomatous colitis, ulcerative colitis, lymphocyte colitis, collagenous colitis and Coeliac disease. In another embodiment, the full length human HSP70 is preferably not used in human subjects for treating or preventing the IBD ulcerative colitis, as non-human HSP70 proteins are preferred for this purpose. In a different embodiment, preferably full length, non-human HSP70 (or variants or a panel of peptides) may be used to treat human or animal subjects, such as non-human mammalian HSP70 protein (e.g. mouse, rat, bovine, etc).

In another embodiment only bacterial HSP70 derived peptides are used, i.e. no mammalian peptides are used in the methods and compositions. In another embodiment only mammalian HSP70 derived peptides are used, i.e. no bacterial peptides are used in the methods and compositions.

In a further embodiment the methods and compositions relate to the use of treatment or prevention of one or more IBDs, wherein the IBDs are non-autoimmune diseases; in one embodiment the IBD is not ulcerative colitis.

As mentioned, fragments used are preferably "functional", i.e. they consist of or comprise one or more protective epitopes and are capable of inducing the production of cross-reactive T-cells when administered to a subject and, especially, to reduce or prevent arthritis or one or more symptoms associated with arthritis. Thus, to test functionality of a fragment, the activation of cross-reactive T cells may be measured as described above or as in the Examples and/or the in vivo functionality may be assessed in an animal model of an autoimmune disease, as described, e.g. in a model of arthritis or another autoimmune disease.

It is understood that the invention also concerns peptide analogues or proteins fragment comprising peptide analogues, which exhibit the immunological properties of the peptides described above, but which contain one or more chemical modifications. Such peptide analogues, also referred to as peptide mimetics, can e.g. consist of units corresponding to the amino acid residues of the peptides described above, wherein essentially the same side groups are present, but wherein the backbone contains modifications such as substitution of an amide group (CO—NH) by another group such as CH=CH, CO—O, CO—CH$_2$ or CH$_2$—CH$_2$. Other modifications, such as substitutions of an amino acid by a similar natural, or non-natural amino acid are also envisaged. In this respect, "similar" means having about the same size, charge and polarity; thus the aliphatic amino acids alanine, valine, norvaline, leucine, isoleucine, norleucine and methionine can be considered as similar; likewise the basic to neutral polar amino acids such as lysine, arginine, ornithine, citrulline, asparagine and glutamine are similar for the present purpose; the same applies to the acidic to neutral polar amino acids like asparagine, aspartate, glutamine, glutamate, serine, homoserine and threonine.

The peptides described above may be used as such, or may be coupled to a sequence which enhances their antigenicity or immunogenicity. Such sequences may include parts of toxoids or immunoglobulins. The peptides may also be used as complexes with MHC molecules and/or incorporated in liposomes. The peptides may also be covalently coupled to other molecules or whole cells as a vector for immuno-stimulation. The peptides may be in the form of monomers, dimers or multimers.

The invention also provides autologous T cells or other cells expressing a T cell receptor, or part thereof, from such T cells, activated by immunostimulation using a protein or peptide as described above.

The invention also concerns antibodies, in particular monoclonal antibodies directed at the peptides described above. The antibodies can be produced using known methods, e.g. by hybridoma technology. The antibodies may be used as a passive vaccine or as a diagnostic tool.

Methods for Identifying HSP70 Epitopes and Peptides

In a further embodiment a method for identifying HSP70-derived peptides suitable for the treatment and/or prevention of arthritis (especially rheumatoid arthritis and/or psoriatic arthritis and/or juvenile arthritis) and/or of another autoimmune diseases such as but not limited to atherosclerosis, multiple sclerosis, myasthenia gravis or symptoms of any of these, is provided, comprising:

Providing one or more HSP70-derived peptides ("test" peptide), preferably from a bacterial and/or mammalian HSP70 protein; and a) optionally determining whether the HSP70-derived peptide(s) is/are capable of binding MHC class II molecules, i.e. binding the MHC class II cleft, or being elutable from the MHC class II molecule;

b) optionally testing the capacity of the "test"-peptide(s) to induce peptide specific T-cell which are cross-reactive with the homologous self-peptide of a mammal (especially a human or animal model or cell lines) in a cross-reactivity assay and selecting those peptides which do show cross-reactivity; and c) optionally administering a composition comprising or consisting of one or more of the "test" peptides in an animal model of the autoimmune disease or the IBD to determine the in vivo protective activity, and comparing disease development and/or symptoms between treated and control animals, thereby verifying that the one or more peptides are suitable for treatment and/or prevention of the autoimmune disease or the IBD (and/or symptoms thereof), and d) using the one or more "test" peptides for the preparation of a medicament for the treatment and/or prevention of the autoimmune disease or IBD in humans or animals and in a method for treating and/or preventing the autoimmune disease in subjects, especially human or animal subjects, such as farm animals or companion animals.

In step (a) any fragment of a bacterial or mammalian HSP70 protein (including human HSP70 proteins) may be used. Many HSP70 amino acids sequences are available and peptides consisting of or comprising a fragment can be synthesized using standard peptide synthesis methods. Preferably, HSP70 proteins are aligned, e.g. from different bacterial origins and/or mammalian origins, and conserved amino acid regions are chosen. The peptide is referred to as the "test" peptide herein below.

In step (b) one preferably determines whether the "test" peptide can bind the MHC class II molecule of humans. The capability to bind can be analysed using various methods, for example using an MHC class II-peptide binding assays.

Steps (a) and (b) can also be interchanged, so that initially test peptides are identified which bind MHC class II molecules, for example by literature analysis, and then synthesizing the test peptide(s) for further use in steps (c), (d) and (e). As step (b) is optional, it can also be omitted.

The optional step (c) involves the analysis whether or not the test peptide(s) is/are able to activate regulatory T cells which are cross-reactive with the homologous self peptide or protein comprising the homologous self amino acids. This can be done by providing the homologous self peptide or protein (e.g. by aligning the "test" peptide of step (a) with the native HSP70 protein of the organism or cell line), and by then testing whether administration of the "self" peptide or protein to the T cells which were primed with the "test" peptide, leads to a T cell activation response, such as proliferation, presentation of activation markers and production of cytokines This can for example be done in vivo (animal models) as well as in vitro (using an in vitro T cell sensitization assay, see Halder T. et al, Isolation of novel HLA-DR restricted potential tumor-associated antigens from the melanoma cell line FM3., *Cancer Res.*, 1997, 57: 3238-44). Test peptides which show cross-reactivity are selected for further use, while peptides which do not show cross-reactivity are discarded.

In step (d) an animal model of the autoimmune disease (such as the arthritis model) or of the IBD (such as the TNBS induced colitis) is used, together with appropriate controls, to determine whether the administration of one or more amounts of the peptide(s) at one or more time points (prior to disease induction or after disease induction) have any effect on disease severity or development. Such animal models of various autoimmune diseases are available in the art, see e.g. the Proteoglycan induced arthritis model described in the Examples. Other arthritis models include for example type II collagen-induced arthritis, proteoglycan-induced arthritis, pristane-induced arthritis, and streptococcal cell wall-induced arthritis (Ref: P H Wooley, Animal models of rheumatoid arthritis, *Curr. Opin. Rheumatol.* 1991 Nr. 3(3): 407-20). Other IBD models include for example chemically induced, immunological, genetic and spontaneous models (see Pizarro T. T., et al., Mouse models for the study of Crohn's disease. *Trends Mol. Med.* 2003 9(5):218-22. Review). The animal model can also be used to determine what the effective concentration and optimal administration mode and administration regime is.

It is also possible to test the functionality and/or effective amounts of one or more HSP70 derived peptides by using transgenic rodents, such as mice, which have been transformed with human MHC class II genes, see for example Koehm S. et al., HLA-DRB1 alleles control allergic bronchopulmonary aspergillosis-like pulmonary responses in humanized transgenic mice, *J. Allergy Clin. Immunol.* 2007, Jun. 8 e-publication ahead of print; Chen Z., et al., Humanized transgenic mice expressing HLA DR4-DQ3 haplotype: reconstitution of phenotype and HLA-restricted T-cell responses, *Tissue Antigens* 2006 No. 68(3): 210-9; Brintnell W. et al., The influence of MHC class II molecules containing the rheumatoid arthritis shared epitope on the immune response to aggrecan G1 and its peptides, *Scand. J. Immunol.* 2007 Nr. 65(5): 444-52; and Mangalam A. et al., Role of MHC class II expressing CD4+ T cells in proteolipid protein (91-110)-induced EAE in HLA-DR3 transgenic mice, *Eur. J. Immunol.* 2006 Nr. 36(12): 3356-70.

In step (e) those peptides or mixtures of peptides which showed a positive effect on treatment and/or prevention of the disease symptoms or progression in step (d) are used to make compositions for clinical or animal trials and for commercial use.

The method may also be used for a panel of peptides covering the full lengths HSP70 proteins or a sub-panel, or mixtures of peptides. In the above method step (c) can optionally be done also with full length HSP70 protein(s), thus in vitro sensitization assay followed by measuring cross-reactivity with purified human hsp70 or stressed antigen presenting cells or with human hsp70 derived peptides. It can also be done in animal models. Cross-reactive T cell responses can then be analysed for induction of regulatory activities (e.g. cytokine like IL-10 production, suppressive activity of hsp specific T cells in co-culture assays).

Compositions and Uses According to the Invention

The proteins and/or peptides of the present invention are used to make pharmaceutical compositions comprising these, whereby the pharmaceutical compositions are useful for administration to mammals, particularly humans and/or animals, especially farm animals or companion animals, to treat and/or prevent arthritis, especially rheumatoid arthritis and/or psoriatic arthritis and/or juvenile arthritis, and/or other autoimmune diseases such as but not limited to atherosclerosis, multiple sclerosis, myasthenia gravis, or one or more (preferably all) symptoms of any of these, or to treat and/or prevent IBD (especially Crohn's disease, granulomatous colitis, ulcerative colitis, lymphocyte colitis, collagenous colitis and/or Coeliac disease), or one or more (preferably all) symptoms thereof, or to treat or prevent other inflammatory diseases, especially atopic dermatitis, food allergies, drug allergies and asthma or one or more symptoms thereof.

The amount of protein or peptide to be used may vary, depending on whether the composition is for the treatment or for the prophylaxis, and depending on the dosage form and frequency of administration. Suitable formulations are found in Remington's Pharmaceutical Sciences, Mack Publishing Company, Philadelphia, Pa., 18th ed. (1990), or in Remington: The Science and Practice of Pharmacy, 2005, Lippincott Williams & Wilkins, US; $21^{st}$ Rev Ed edition.

In one embodiment, the immunogenic peptides of the invention (or compositions comprising these) are administered prophylactically (prevention) or to an individual already suffering from the autoimmune disease or the inflammatory disease (treatment). The compositions are administered to a subject (e.g. a patient) in an amount sufficient to elicit an effective immune response. An amount adequate to accomplish this is defined as "therapeutically effective dose" or "immunogenically effective dose". Amounts effective for this use will depend on, e.g., the peptide composition, the manner of administration, the stage and severity of the disease being treated, the weight and general state of health of the subject, and the judgement of the prescribing physician, but generally range for the from about 0.1 µg to about 150 µg per kilogram (kg) of body weight per subject, or from about 1 µg to about 200 µg per kg of body weight, more commonly from about 1 µg to about 50 µg per kg of body weight per dose. A dose may be administered once a week, or once every other day or daily or even several times per day. Dosage units may be administered over a short period (e.g. a few weeks to months) or over longer time periods (several months to years).

The composition may be made in various dosage units, such as doses comprising e.g. 7 µg, 7.5 µg, 8 µg, 9 µg, 10 µg, 20 µg, 30 µg, 40 µg, 50 µg, 100 µg, 200 µg, 1000 µg, 2500 µg, 5000 µg or more of each HSP70-derived peptide (and optionally further also of a HSP70 panel or sub-panel).

Preferably, the pharmaceutical compositions are administered mucosally, most preferably oral or intra-nasally. However, in another embodiment other forms of administration are included, such as transdermal, inhalation, and parenteral. Especially preferred are oral and nasal formulations.

The proteins and/or peptides according to the invention may, for example, be dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as buffering agents, tonicity adjusting agents, wetting agents and the like, for example, sodium acetate, sodium lactate, sodium bicarbonate, sodium chloride, potassium chloride, calcium chloride, sorbitan monolaurate, and triethanolamine oleate.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and about 0.1 to 5% or 10%, more preferably 0.1-2%, of (preferably each) active ingredient. As noted above, the compositions are intended to induce an immune response to the peptides. Thus, compositions and methods of administration suitable for maximizing the immune response are preferred. For instance, peptides may be introduced into a host, including humans, linked to a carrier or as a homopolymer or heteropolymer of active peptide units. Alternatively, the "cocktail" of peptides can be used. A mixture of more than one peptide has the advantage of increased immunological reaction.

The compositions, especially oral dosage forms, may further comprise one or more protease inhibitors. Protease inhibitors are divided into four classes: serine protease inhibitors (including trypsin inhibitors), cysteine protease inhibitors, aspartic protease inhibitors, and metalloproteinase inhibitors. Suitable protease inhibitors are available in the art (e.g. from Sigma-Aldrich). A preferred inhibitor is a trypsin inhibitor, such as a plant derived trypsin inhibitor (soybean trypsin inhibitor, lima bean trypsin inhibitor, corn trypsin inhibitor, etc.) or animal derived trypsin inhibitor (trypsin inhibitor from chicken or turkey egg white, from bovine pancreas, etc).

The compositions may also include an adjuvant. A number of adjuvants are well known to one skilled in the art. Suitable adjuvants include incomplete Freund's adjuvant, alum, aluminium phosphate, aluminium hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1',2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

The concentration of immunogenic peptides of the invention in the pharmaceutical formulations can vary widely, i.e. from less than about 0.1% (e.g. 0.01% wt/vol) to about 2% or more by weight, and will be selected primarily by fluid volumes, viscosities, etc., in accordance with the particular mode of administration selected.

Further guidance regarding formulations that are suitable for various types of administration can be found in Remington's Pharmaceutical Sciences, Mace Publishing Company, Philadelphia, Pa., 18th ed. (1990, supra). For a brief review of methods for drug delivery, see, Langer, Science 249:1527-1533 (1990). Both of these references are incorporated herein by reference in their entirety.

Transdermal delivery systems include patches, gels, tapes and creams, and can contain excipients such as solubilizers, permeation enhancers (e.g. fatty acids, fatty acid esters, fatty alcohols and amino acids), hydrophilic polymers (e.g. polycarbophil and polyvinyl pyrrolidine and adhesives and tackifiers (e.g. polyisobutylenes, silicone-based adhesives, acrylates and polybutene) Transmucosal delivery systems include patches, tablets, suppositories, pessaries, gels, and creams, and can contain excipients such as solubilizers and enhancers (e.g. propylene glycol, bile salts and amino acids), and other vehicles (e.g. polyethylene glycol, fatty acid esters and derivatives, and hydrophilic polymers such as hydroxypropylmethyl cellulose and hyaluronic acid). Injectable delivery systems include solutions, suspensions, gels, microspheres and polymeric injectables, and can comprise excipients such as solubility-altering agents (e.g. ethanol, propylene glycol and sucrose) and polymers (e.g. polycapryl lactones, and PLGA's). Implantable systems include rods and discs, and can contain excipients such as PLGA and polycapryl lactone.

Other delivery systems that can be used for administering the pharmaceutical composition of the invention include intranasal delivery systems such as sprays and powders, sublingual delivery systems and systems for delivery by inhalation. For administration by inhalation, the pharmaceutical compositions of the present invention are conveniently delivered in the form of an aerosol spray presentation from presurised packs or a nebuliser, with the use of a suitable propellant, e.g., dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of, e.g., gelatin for use in an inhaler or insufflator may be formulated containing a powder mix of the peptides of the invention and a suitable powder base such as lactose or starch. The pharmaceutical compositions of the invention may be further formulated for administration by inhalation as e.g. described in U.S. Pat. No. 6,358,530. Also other vaccination or administration methods may be used, such as particle bombardment (biolistics), whereby DNA or RNA encoding the epitope(s), i.e. the peptides and/or proteins according to the invention, is coated onto gold particles and these are used to bombard the subjects tissue, see e.g. van Drunen et al. *Methods Mol. Med.* 2006; 127:91-105; Gaffal et al. *Eur. J. Cell. Biol.* 2006, Available online 22 Aug. 2006) or liposome delivery. Thus, in one embodiment, DNA or RNA encoding the proteins and/or peptides according to the invention are provided (e.g. plasmids comprising the DNA or RNA), as are compositions comprising these.

In another aspect the invention relates to a method for producing a pharmaceutical composition comprising the peptides or proteins of the invention. The method comprises at least the steps of mixing the peptides or proteins of the invention with a pharmaceutically acceptable carrier and further constituents like adjuvant as described above. Also gold particles coated with one or more peptides and/or proteins according to the invention are provided, for use in biolistic applications.

Also provided is a method for the treatment or prevention of arthritis (especially rheumatoid arthritis and/or psoriatic arthritis and/or juvenile arthritis) and/or other autoimmune diseases such as atherosclerosis, multiple sclerosis, myasthenia gravis, or one or more (preferably all) symptoms of any of these in a human subject or inflammatory bowel diseases (IBD), comprising administering to a person in need thereof a therapeutically or prophylactically effective amount of one or more peptides as described above. In a preferred embodiment the administration is mucosally, preferably orally and/or nasally, at a regular interval.

It is noted that the therapeutic and prophylactic (protective) treatments described herein are not limited to the complete abolishment or complete prevention of disease, but in one embodiment also refer to a significant reduction in severity of one or more arthritis symptoms and/or symptoms of one or more other autoimmune diseases in the treated subject group compared to the control group, as described in the examples for arthritis. For example one or more symptoms associated with the arthritis and/or another autoimmune disease and/or the IBD, such as the weight loss (clinical state), colon shortening, and/or histomorphological changes etc., may be significantly reduced in the treated group. A significant reduction should be statistically significant, and the skilled person can easily determine whether this is the case. For example, a reduction in one or more symptoms by at least about 1%, 2%, 5%, 10%, 20% or more, compared to the control group, may be significant.

Arthritis symptoms include for example redness and swelling of the paws or weight loss in animals. In humans generally accepted disease activity criteria/accepted response criteria may be assessed, such as for example arthritis response criteria described in Health Technology Assessment 2002, Vol. 6, No. 21, p83, which include for example "tender joint count", "swollen joint count", "patient assessment of pain", and other criteria for assessing disease symptoms and severity. For other autoimmune disease similar standard criteria for evaluating symptoms and disease severity are available in the art.

It is noted that the therapeutic and prophylactic (protective) treatments described herein are not limited to the complete abolishment or complete prevention of disease, but in one embodiment also refer to a significant reduction in severity of one or more IBD symptoms in the treated subject group compared to the control group, as described in the examples. For example one or more symptoms associated with the IBD, such as the weight loss (clinical state), colon shortening, and/or histomorphological changes etc. may be significantly reduced in the treated group. A significant reduction should be statistically significant, and the skilled person can easily determine whether this is the case. For example, a reduction in one or more symptoms by at least about 1%, 2%, 5%, 10%, 20% or more, compared to the control group, may be significant.

Table 1 below shows the result of the literature study of MHC class II bound/eluted mammalian HSP70-derived peptides. The peptides are useful for the treatment or prevention of arthritis or IBD in humans or other animals. The peptides to be used according to the invention preferably have at least 70% amino acid identity with the sequences of the table. Also, homologous peptides from other species, especially bacterial species can be advantageously used.

TABLE 1

Peptides derived from mammalian HSP70 family members that have been eluted from MHC Class II molecules

| Sequence and SEQ ID | MHC class II type | MHC source | Potential Peptide source | Protein source ($) | Reference |
|---|---|---|---|---|---|
| IIANDQGNRTTPSY (SEQ ID NO: 17) | I-Ak | mouse | hspa8 (28-41) hspa2 (29-42) hspa11 (30-43) hspa1a (28-41) hspa1b (28-41) | m m m m m | Nelson et. al., (1992), PNAS, 89:7380-83 |
| ITPSYVAFTPEGERL (SEQ ID NO: 18) | I-Ab | mouse | hspa5 (62-76) | m | Dongre et al. (2001), Eur. J. Immunol., 31:1485-1494 |
| TPSYVAFTDTERLIG (SEQ ID NO: 19) | HLA-DR7 | human | hspa8 (38-52) hspa2 (39-53) hspa11 (40-54) Hspa1a (38-52) | h h h h | Chicz et al. (1993), J.Exp. Med., 178:27-47 |
| TPSYVAFTDTERLIGDA (SEQ ID NO: 20) | HLA-DR7 | human | as above | h | Chicz et al. (1993), J.Exp. Med., 178:27-47 |
| DAAKNQLTSNPEN (SEQ ID NO: 21) | I-Ag7 | mouse | hspa5 (79-91) | m | Suri et al., (2005), J. Clin. Invest., 115:2268-2276 (supl) |
| NPTNTVFDAKRLIGRRFD (SEQ ID NO: 22) | HLA-DRB1*1104 | human | hspa8 (62-79) | h | Verreck et al. (1996) Immunogenetics, 43:392-397 |

TABLE 1-continued

Peptides derived from mammalian HSP70 family members that have been eluted from MHC Class II molecules

| Sequence and SEQ ID | MHC class II type | MHC source | Potential Peptide source | Protein source ($) | Reference |
|---|---|---|---|---|---|
| QDIKFLPFKVVEKKTKPY (SEQ ID NO: 23) | BoLA-DRB3*1201 (in mouse line) | Bovine | hspa5 (111-128) | m | Sharif et al. (2003) Anim. Genet., 34:116-123 |
| LNVLRIINEPTAAAIAYG (SEQ ID NO: 24) | HLA-DRB*0401 (in rat line) | human | hspa8 (167-184) | r | Muntasell et al. (2004) J. Immunol., 173:1085-1093 |
| (NVLRIINEPTAAAIAYG) (SEQ ID NO: 25) | | | hspa1a (167-184) hspa1l (169-186) hspa2 (168-185) | r r r | |
| NVLRIINEPTAAAIAYG (SEQ ID NO: 26) | HLA-DRB1*0401/ DRB4*0101 | human | hspa8 (168-184) hspa1a (168-184) hspa1l (170-186) hspa2 (169-185) hspa6 (170-186) | h h h h h | Dengjel et al., (2005), PNAS, 102:7922-7927. table 1 |
| NVLRIINEPTAAAIA (SEQ ID NO: 27) | multiple HLA mix | human | hspa8 (168-184) hspa1a (168-184) hspa1l (170-186) hspa2 (169-185) hspa6 (170-186) | h h h h h | Halder et al. (1997) Cancer Res., 57:3238-3244 |
| NVMRIINEPTAAAIAYG (SEQ ID NO: 28) | multiple HLA mix | human | hspa5 (194-210) | h | Halder et al. (1997) Cancer Res., 57:3238-3244 |
| VMRIINEPTAAAIAYG (SEQ ID NO: 29) | HLA-DRB1*0401/ DRB4*0101 | human | hspa5 (195-210) | h | Dengjel et al., (2005), PNAS, 102:7922-7927 (supl. tbl 3) |
| IINEPTAAAIAYGLD (SEQ ID NO: 30) | HLA-DQ6 (B*602) | human | hspa8 (172-186) hspa2 (173-187) hspa1l (174-188) hspa1a (172-186) hspa5 (198-212) | h h h h h | Sanjeevi et al. (2002), Ann. N.Y. Acad. Sci., 958:317-320 |
| NRMVNHFIAEFKRK (SEQ ID NO: 31) | I-Ek | mouse | hspa8 (236-249) | m | Marrack et al. (1993) J. Exp. Med., 178:2173-2183 |
| RMVNHFIAEFKRKH (SEQ ID NO: 32) | I-Ek | mouse | hspa8 (236-249) | m | Freed et al. (2000), J. Immunol., 164:4697-4705 |
| VNHFIAEFKRKHKKD (SEQ ID NO: 33) | HLA-DR11/w52 | human | hspa8 (238-252) | h | Newcomb and Cresswell (1993), J.Imm., 150:499-507 |
| XDFYTSITRAXFEE (SEQ ID NO: 34) | HLA-DR11/w52 | human | hspa8 (291-304) hspa1a (291-304) hspa1l (293-306) hspa2 (294-307) hspa6 (294-306) | h h h h h | Newcomb and Cresswell (1993), J.Imm., 150:499-507 |
| EGEDFSETLTRAKFEEL (SEQ ID NO: 35) | BoLA-DRB3*1201 (in mouse line) | bovine | hspa5 (315-331) | m | Sharif et al. (2003) Anim. Genet., 34:116-123 |
| ADLFRGTLDPVEK (SEQ ID NO: 36) | HLA-DQ6 (B*0604) | human | hspa8 (307-319) | h | Sanjeevi et al. (2002), Ann. N.Y. Acad. Sci., 958:317-320 |

TABLE 1-continued

Peptides derived from mammalian HSP70 family members that have been eluted from MHC Class II molecules

| Sequence and SEQ ID | MHC class II type | MHC source | Potential Peptide source | Protein source ($) | Reference |
|---|---|---|---|---|---|
| TIPTKQTQTFTTYSDNQP (SEQ ID NO: 37) | RT1.B1 | rat | hspa8 (419-436)<br>hspa1a (419-436) | r<br>r | Reisiz et al. (1996) Intern. Immunol., 8:1825-1832 |
| VPTKKSQIFSTASDNQPTVT (SEQ ID NO: 38) | HLA-DRB1*0401/ DRB4*0101 | human | hspa5 (443-462) | h | Dengjel et al., (2005), PNAS, 102:7922-7927 (supl. tbl 3) |
| GERAMTKDNNLLG (SEQ ID NO: 39) | HLA-DR4Dw4 | human | hspa8 (445-457)<br>hspa1a (445-457)<br>hspa11 (447-459)<br>hspa2 (448-460)<br>hspa6 (447-459) | h<br>h<br>h<br>h<br>h | Friede et al.(1996), BBA, 1316:85-101 |
| GERAMTKDNNLLGKFE (SEQ ID NO: 40) | HLA-DRB1*0401/ DRB4*0101 | human | hspa8 (445-460)<br>hspa1a (445-460) | h<br>h | Dengjel et al., (2005), PNAS, 102:7922-7927 tbl 1 |
| GERAMTKDNNLLGRFE (SEQ ID NO: 41) | HLA-DRB1*0401/ DRB4*0101 | human | hspa6 (447-462) | h | Dengjel et al., (2005), PNAS, 102:7922-7927 (supl. tbl 3) |
| ANGILNVSAVDKSTGKE (SEQ ID NO: 42) | HLA-DRB*0401 | human | hspa8 (482-499) | h | Lippolis et al. (2002), J. Imm., 169:5089-97 |
| GILNVSAVDKSTGK (SEQ ID NO: 43) | HLA-DRB*0401 | human | hspa8 (484-497) | h | Lippolis et al. (2002), J. Imm., 169:5089-97 |
| GILNVSAVDKSTGKE (SEQ ID NO: 44) | HLA-DRB1*0401/ DRB4*0101 | human | hspa8 (484-498) | h | Dengjel et al., (2005), PNAS, 102:7922-7927 tbl 1 |
| CNEIINWLDKNQ (SEQ ID NO: 45) | HLA-DR4Dw10 | human | hspa8 (574-585) | h | Friede et al.(1996), BBA, 1316:85-101 |
| ISWLDKNQTAEKEEFE (SEQ ID NO: 46) | HLA-DQ8 (transgenic in NOD!) | human | hspa8 (578-593) | m | Suri et al., (2005), J. Clin. Invest., 115:2268-2276 (suppl) |
| YGSGGPPPTGEEDTSEKDEL (SEQ ID NO: 47) | I-Ag7 | mouse | hspa5 (636-655) | m | Suri et al., (2005), J. Clin. Invest., 115:2268-2276 (suppl) |

$: Species from which the HSP70 protein originates: m mouse; h human; r rat

Suitable HSP70 sequences for selection of peptides according to the invention are listed in Table 2. The sequences are based on the peptides from table 1 which have a medium or high degree of conservation. The source species are indicated: 'mamm' means mammalian, including human, 'Yeast' means *Saccharomyces cerevisiae* (SSA3 and SSB2 proteins), 'Mycob' means *Mycobacterium* including *M. tuberculosis* (*leprae* and *gilvum* being identical in the corresponding regions). Corresponding sequences from other species and other HSP70 proteins can be readily identified by comparison with available sequences of these other species or proteins. Preferred peptides have at least 12, more preferably at lest 13, most preferably at least 14 or even 15 amino acids, up to at most 19, more preferably at most 18, most preferably at most 17 or even 16 amino acids from the sequences of table 2. In addition to the specific sequences of table 2, also those peptides are covered by the invention wherein 1, 2, 3 or up to 4 amino acids are exchanged by a highly conserved amino acid, or by the corresponding amino acids from a peptide of the same group 56-72, 73-82, 83-94, 95-105, 106-119 or 120-132. For example, peptides based on SEQ ID NO: 72, wherein the second leucine is replaced by methionine (SEQ 57), alanine (from SEQ 62), glutaminic acid (from SEQ 66, 69 or 71), or lysine (from SEQ 80) or the third leucine by isoleucine (from e.g. SEQ 56) are also covered. Sets of highly conserved amino acids are e.g. V, L, I and M; R and K; D and E; N and Q; D and N; E and Q; S and T; G and A; F, W and Y; and the like. Most preferred are peptides are those missing the first two amino acids and/or the last two or three of the sequences of Table 2. Especially preferred are mycobacterial peptides with at most three, more preferably two or one, highly conserved substitutions or exchanges as described above, or an identical (partial) sequence. In a mycobacterial peptide based on C1, it is preferred that at least one of V at position 145 (V-145) and L-153 is preserved; similarly for B1, at least one of V-344, G-354 and V-355 is retained; and for B2, at least one of E-31, T-35 and V-39 (or I or T) is retained.

TABLE 2

Conserved peptides based on HSP70 family members eluted from MHC Class II molecules.

| | SEQ ID No. | Region of *Mycob.* HSP70 | Includes | Species |
|---|---|---|---|---|
| LNVLRIINEPTAAAIAYGLD | 56 | | | human, bovine, mouse, dog, pig, rat, soy, *Candida albicans*, *Arabidopsis thaliana*, *Chaenorhabditis elegans* |
| LNVMRIINEPTAAAIAYGLD | 57 | | | Mamm, *Gallus gallus*, *Zea mais*, *Arabidopsis thaliana* |
| LNVLRVINEPTAAALAYGLD | 58 | | | Mamm |
| LKVLPIINEATAAAIAYGLD | 59 | | | Human HSP70 7 |
| FNVLRLIHEPSAALLAYGIG | 60 | | | Human, mouse HSP70 14 |
| LNVLRIINEPTAAALAYGLD | 61 | | | *Drosophila melanogaster* |
| LNVARIINEPTAAAIAYGLD | 62 | | | *Arabidopsis thaliana* |
| MNVLRIINEPTAAAIAYGLD | 63 | | | Yeast SSA3 |
| LNVLRIINEPTAAAIAYGLG | 64 | | | *Candida albicans*, Yeast SSB2 |
| LNVLRVVNEPTAAALAYGLE | 65 | | | *Candida albicans* |
| LEVERIVNEPTAAALAYGLD | 66 | | | *Lactobacillus lactis*, *Streptococcus thermophilus* |
| LNVQRIINEPTASALAYGLD | 67 | | | *Lactobacillus delbrueckii*; *Lb. acidophilus* |
| LNVQRIINEPTASALAFGLN | 68 | | | *Lactobacillus helveticus* |
| LEVERIINEPTAAALAYGLD | 69 | | | *Bacillus subtilis* |
| LEVKRIINEPTAAALAYGLD | 70 | | | *Escherichia coli* |
| LQVERIINEPTAAALAYGLD | 71 | | | *Mycoplasma mycoides* |
| LNVLRIVNEPTAAALAYGLD | 72 | 139-158 | C1 | *Mycob* |
| IIANDQGNRTTPSYVAFTDT | 73 | | | human, bovine |
| IIANDQGNRITPSYVAFTPE | 74 | | | mamm |
| IIANDQGNRTTPSYVAFTDS | 75 | | | *Arabidopsis thaliana* |
| IIANDQGNRTTPSYVAFTDT | 76 | | | Yeast SSA3 |
| IIANEQGNRVTPSFVAFTPQ | 77 | | | Yeast SSB2 |
| VIPNPEGNRTTPSVAFKDG | 78 | | | *Bacillus halodurans* |
| VIANAEGNRTTPSVVAFKNG | 79 | | | *Bacillus subtilis* |
| VVANSEGSRTTPSIVAFARN | 80 | 26-45 | B2 | *Mycob. tuberc.; avium; paratuberculosis.; bovis* |
| VVANSEGSRTTPSTVAFARN | 81 | 26-45 | | *Mycob. leprae* |
| VVANSEGSRTTPSVVAFARN | 82 | 26-45 | | *Mycob. gilvum; smegmatis* |
| NPDEAVAYGAAVQAAILMGD | 83 | | | human, bovine, avian |
| NPDEAVAYGAAVQAAILIGD | 84 | | | mamm |
| NPDEAVAYGAAVQAGVLSGD | 85 | | | mamm |
| NPDEAVAYGAAVQAAVLMGD | 86 | | | mamm |
| NPDEAVAYGAAVQAAILSGD | 87 | | | mamm |

TABLE 2-continued

Conserved peptides based on HSP70 family members eluted from MHC Class II molecules.

| | SEQ ID No. | Region of *Mycob.* HSP70 | Includes | Species |
|---|---|---|---|---|
| NPDEAVAIGAAIQGGVLAGD | 88 | | | mamm |
| NPDEAVAYGAAVQGAILSGE | 89 | | | *Arabidopsis thaliana* |
| NPDEAVAYGAAVQAAILTGD | 90 | | | *Candida albicans*<br>Yeast SSA3 |
| NPDEAVAYGAAVQGAILTGQ | 91 | | | Yeast SSB2 |
| NPDEVVALGAAVQAGVLTGD | 92 | | | *Bacillus halodurans* |
| NPDEVVAMGAAVQGGVLAGE | 93 | | | *Mycoplasma mycoides* |
| NPDEVVAVGAALQAGVLKGE | 94 | 340-359 | B1 | *Mycob* |
| TIPTKQTQIFTTYSDNQPGV | 95 | | | human, bovine |
| TIPTKQTQTFTTYSDNQSSV | 96 | | | mamm |
| VVPTKKSQIFSTASDNQPTV | 97 | | | mamm |
| TIPTKQTQTFTTYSDNQPGV | 98 | | | human, rat |
| TIPTKKSQVFSTAADGQTQV | 99 | | | mamm |
| TIPTKKEQVFSTYSDNQPGV | 100 | | | *Arabidopsis thaliana* |
| TIPTKKSETFSTYADNQPGV | 101 | | | Yeast SSA3 |
| TVPTIKRRTFTTVSDNQTTV | 102 | | | Yeast SSB2 |
| TIPTSKSQIFSTAADNQPSV | 103 | | | *Bacillus halodurans* |
| TIPAKRTQIFSTATDNQPAV | 104 | | | *Mycoplasma mycoides* |
| TIPTKRSETFTTADDNQPSV | 105 | 391-410 | | *Mycob.* |
| EGERAMTKDNNLLGRFELSG | 106 | | | human |
| EGERAMTRDNNLLGRFELSG | 107 | | | bovine |
| EGERAMTKDNNLLGRFDLTG | 108 | | | mamm |
| EGERAMTKDNNLLGKFDLTG | 109 | | | mamm |
| EGERPLTKDNHLLGTFDLTG | 110 | | | mamm |
| EGERAMTKDNNLLGKFELTG | 111 | | | mamm |
| QGEREMAGDNKLLGQFTLIG | 112 | | | mamm |
| EGERARTKDNNLLGKFELSG | 113 | | | *Arabidopsis thaliana* |
| EGERTRTKDNNLLGKFELSG | 114 | | | Yeast SSA3 |
| QGERVNCKENTLLGEFDLKN | 115 | | | Yeast SSB2 |
| QGEREMAADNKTLGRFQLTD | 116 | | | *Bacillus halodurans* |
| QGERAMAADNKSLGQFQLTG | 117 | | | *Mycoplasma mycoides* |
| QGEREIAAHNKLLGSFELTG | 118 | 416-435 | | *Mycob. tuberc., avium, paratuberc.* |
| QGEREIASHNKLLGSFELTG | 119 | 416-435 | | *M. leprae, gilvum, smegmatis* |
| DIDANGILNVTATDKSTGKA | 120 | | | human, bovine |
| DIDANGILNVTATDKSTGKV | 121 | | | mamm |
| DIDANGILNVTAADKSTGKE | 122 | | | mamm |

TABLE 2-continued

Conserved peptides based on HSP70 family members eluted from MHC Class II molecules.

| | SEQ ID No. | Region of *Mycob.* HSP70 | Includes | Species |
|---|---|---|---|---|
| EIDVNGILRVTAEDKGTGNK | 123 | | | mamm |
| DIDANGILSVTATDRSTGKA | 124 | | | mamm |
| DIDANGILNVSAVDKSTGKE | 125 | | | mamm |
| DIDANGIVHVSAKDKGTGRE | 126 | | | mamm |
| DIDANGILNVSAEDKTTGQK | 127 | | | *Arabidopsis thaliana* |
| DIDANGILNVSALEKGTGKS | 128 | | | Yeast SSA3 |
| EVDANGILKVTAVEKSTGKS | 129 | | | Yeast SSB2 |
| DIDANGIVNVKAKDLGTNKE | 130 | | | *Bacillus halodurans* |
| EIDANGIVSVSAKDKNTNEE | 131 | | | *Mycoplasma mycoides* |
| DIDANGIVHVTAKDKGTGKE | 132 | 451-470 | (C4) | *Mycob.* |

Sequences

SEQ ID NO 1: Mycobacterial HSP70 peptide "B1"

SEQ ID NO 2: mouse HSP70 homologue peptide "mB1"

SEQ ID NO 3: Mycobacterial HSP70 peptide "C1"

SEQ ID NO 4 and 5: Mouse HSP70 homologue peptide "mC1a" and "mC1b"

SEQ ID NO 6-16: Mycobacterial HSP70 peptides used in the Examples

SEQ ID NO 17-47: list of MHC class II presented mammalian HSP70 peptides

SEQ ID NO 48-54: human HSP70 proteins

SEQ ID NO 55: *Mycobacterium* HSP70 protein.

SEQ ID NO 56-132: Preferred sequences of conserved HSP70 regions.

Figure Legends

FIG. 1—T-cell proliferation of Example 1 (HSP70 epitope mapping)

FIG. 2—Cytokine production of Example 1 (HSP70 epitope mapping)

FIG. 3—a) and b) Murine DSS colitis experimental schedules

FIG. 4 to FIG. 7—Suppressive effect of full length Mycobacterial HSP70 protein on DSS Colitis (Example 3); FIG. 4 (colon length—peroral group), FIG. 5 (weight change—peroral group), FIG. 6 (Clinical state—peroral group) and FIG. 7 (histological grade—peroral group).

FIG. 8 to FIG. 11—Suppressive effect of full length Mycobacterial HSP70 protein on DSS Colitis (Example 4); FIG. 8 (Colon length—peroral group), FIG. 9 (weight change—peroral group), FIG. 10 (Clinical state—peroral group) and FIG. 11 (histological grade—peroral group).

FIG. 12—Murine DSS colitis experimental schedule

FIG. 13—Disease onset of Example 5

FIG. 14—Maximum body weight loss of Example 5

FIG. 15—Colon length data of Example 5

FIG. 16—IL10 release from distal colon samples of Example 5

FIG. 17—Murine TNBS colitis experimental schedule

FIG. 18—Effects on body weight of Example 6

FIG. 19—Effects on IL10 production by draining lymph node cells (CLN); (CD3/CD28 restimulation).

FIG. 20—A), B) and C) Experimental schedules (3A: Schedule of administration of full length mycobacterial HSP70) (3B: Schedule of administration of peptides or peptide mixtures) (3C: Schedule of administration of peptide mixture)

FIG. 21—Arthritis score after administration of full length mycobacterial HSP70 protein; *$p<0.05$ (Mann-Whitney U test).

FIG. 22—Arthritis score after administration of a mixture of peptides C1 and mC1a (designated "C1 mix")

FIG. 23—Arthritis score after administration of a peptide "B1"

FIG. 24—Antigen specific T-cell proliferation assay results. After sacrifice of the mice, spleen cells were isolated and in vitro restimulated for 72 hours with antigen followed by 18 hour incubation with 3H. Stimulation index (CPM antigen/CPM medium stimulated cells) was calculated and depicted per in vivo treatment group. CPM=counts per minute of radioactive tritium.

FIG. 25—Antigen-specific IFN-gamma production

In addition to antigen specific proliferation IFN-γ production was measured by ELISA. Supernatants, of in vitro restimulated spleen cells, were taken after 72 hours of culture.

FIG. 26—Antigen specific IL-10 production

In addition to antigen specific proliferation IL-10 production was measured by ELISA. Supernatants, of in vitro restimulated spleen cells, were taken after 72 hours of culture.

FIG. 27—Arthritis score after administration of a mixture of peptides C1 and mC1a (designated "C1 mix")

FIG. 28—Experimental schedule

FIG. 29—arthritis score after treatment with peptides C1 or mC1 a;

* $p<0.05$ (Mann-Whitney U test)

** $p<0.01$ (Mann-Whitney U test)

FIG. 30—Peptide-specific response in human cells (Example 12)

(A) Peptide-specific proliferation of PBMC isolated from the blood of healthy donors was determined by measuring [$^3$H] incorporation after 96 hours incubation. mC1b induced increased proliferation of PBMC. Results are expressed as mean stimulation index (CPM Antigen/CPM background).

(B) In one JIA patient peptide-specific production of IL-10, TNFα and IFNγ was addressed by intracellular staining and FACS analysis, in SFMC after eight days culturing in the presence of peptides as described in materials and methods. During the last 6 hours fresh medium, peptides and APC were added. Data are expressed as % positive cells from CD3$^+$CD4$^+$ population.

The following non-limiting Examples describe the protective and therapeutic use of antigenic proteins and peptides of the invention. Unless stated otherwise in the Examples, all molecular techniques are carried out according to standard protocols as described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols, USA and in Volumes I and II of Brown (1998) Molecular Biology LabFax, Second Edition, Academic Press (UK).

EXAMPLES

Example 1

Mapping of Bacterial HSP70 Peptides Recognized by HSP70 Specific T Cells, Including T Cells that Cross-react with Self HSP70

HSP70-specific regulatory T cells, from HSP immunized mice, are a limited source of regulatory T cells (Tregs). Besides that, HSP-specificity is depending on immunization and will be variable. To achieve an alternative source, and a more precisely defined population of Hsp-specific regulatory T cells we started HSP70 epitope mapping.

Spleen cells from Balb/c mice immunized with whole Mycobacterial HSP70 (SEQ ID NO: 55 (intraperitoneally and subcutaneously a total of 100 μg in 200 μl 10 mg/ml dimethyl dioctadecyl ammonium bromide (DDA) as adjuvant in PBS), were analyzed for T cell responses against a complete set of 123 overlapping 15-mer peptides covering the whole protein according to procedures previously described (Wendling et al. (2000) J. Immunol. 164: 2711-2717).

In this way we identified 13 Hsp70 peptides that were more or less recognized by Hsp70 specific T cells and possibly involved in activation of Hsp-specific regulatory T cells.

To define the epitopes more precisely, we divided the 13 peptides, based on the degree of sequence identity between bacterial and the homologous mouse Hsp70s, in three pools (pool A: non-conserved peptides, pool B: conserved peptides comprising at least about 80% amino acid identity to the mouse homologue, and pool C: highly conserved peptides comprising >86% amino acid identity to the mouse homologue, see below) and immunized 10-12 weeks old Balb/c mice twice with a 2 week interval (intraperitoneally and subcutaneously) with the peptide pools. 10 days after the second immunization primed spleen and draining lymph node cells were re-stimulated in vitro with all the 13 individual peptides after which we measured T-cell proliferation (tritium incorporation), IFNγ, IL10, IL4 and IL5 production (cytokine production).

We identified three (out of the thirteen) peptides that induced clear responses (see FIG. 1): three peptides induced increased proliferative T-cell responses and IFNγ (peptides A1, B1, C1) and two peptides induced augmented IL-10 production (peptide A1, C1). None of the peptides induced detectable IL4 or IL5.

Cross reactivity was determined with the corresponding mouse homologue peptides. Peptides B1 and C1 were found to have induced cross reactive T cell responses to their corresponding mouse homologue peptides (with respect to both proliferation and cytokine production (see responses to mouse homologue peptides mB1, mC1a, mC1b).

The peptides containing T cell epitopes are used to generate peptide-specific T cell lines and hybridomas. These T cell lines are used both in vitro and in vivo as a source of Hsp specific regulatory T cells. Further, activation of the lines and hybridomas is used to study the effect of Hsp manipulation of antigen presenting cells on Hsp peptide specific T-cell activation. Peptides C1 and mC1a have been used in the TNBS colitis studies.

| pool A (not conserved) | pool B (conserved) | pool C (highly conserved) |
|---|---|---|
| A1 = KPFQSVIADTGISVS (SEQ ID NO: 6, SEQ ID NO: 55, 291-305) | B1 = DEVVAVGAALQAGVL (SEQ ID NO: 1, SEQ ID NO: 55, 342-356) | C1 = VLRIVNEPTAAALAY (SEQ ID NO: 3, SEQ ID NO: 55, 141-155) |
| A2 = YTAPEISARILMKLK (SEQ ID NO: 7, SEQ ID NO: 55, 86-100) | B2 = EGSRTTPSIVAFARN (SEQ ID NO: 10, SEQ ID NO: 55, 31-45) | C2 = ILVFDLGGGTFDVSL (SEQ ID NO: 14, SEQ ID NO: 55, 166-180) |
| A3 = AEGGSKVPEDTLNKV (SEQ ID NO: 8, SEQ ID 55, 530-544) | B3 = MQRLREAAEKAKIEL (SEQ ID NO: 11, SEQ ID NO: 55, 231-245) | C3 = RGIPQIEVTFDIDAN (SEQ ID NO: 15, SEQ ID NO: 55, 441-455) |
| A4 = AQAASQATGAAHPGG (SEQ ID NO: 9, SEQ ID NO: 55, 585-599) | B4 = GGKEPNKGVNPDEVV (SEQ ID NO: 12, SEQ ID NO: 55, 331-345) | C4 = QIEVTFDIDANGIVH (SEQ ID NO: 16, SEQ ID NO: 55, 445-459) |
| | B5 = LDVTPLSLGIETKGG (SEQ ID NO: 13, SEQ ID NO: 55, 366-380) | |

Figure 2B:
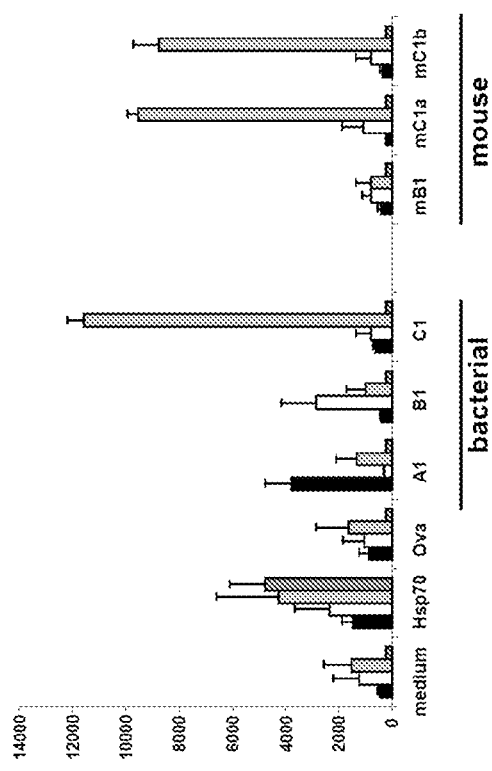

Results are shown in FIGS. 1 and 2, and are summarized below:

TABLE 3

Summary Hsp70 epitope mapping

| Peptide | T-cell proliferation response | IFN-gamma | IL-10 | Cross-reactivity of bacterially primed T-cells with mouse homologue peptide |
|---|---|---|---|---|
| A1 (SEQ ID NO: 6) | + | + | + | no |
| B1 (SEQ ID NO: 1) | + | + | − | yes |
| C1 (SEQ ID NO: 3) | ++ | ++ | ++ | yes |

Mycobacterial peptides:

```
A1 = mycobacterial hsp70 peptide      SEQ ID NO: 6
(KPFQSVIADTGISVS) -

B1 = mycobacterial hsp70 peptide      SEQ ID NO: 1
(DEVVAVGAALQAGVL) -

C1 = mycobacterial hsp70              SEQ ID NO: 3
(VLRIVNEPTAAALAY) -
```

Mouse homologues:

```
mB1 = mouse Grp75 peptide (hspa9a)    SEQ ID NO: 2
(DEAVAIGAAIQGGVL) - mC1a = mouse Grp75 (hspa9a) peptide   SEQ ID NO: 4
(VLRVINEPTAAALAY) - mC1b = mouse hsp70 (hspa1a/hspa8)     SEQ ID NO: 5
peptide (VLRIINEPTAAAIAY)
```

Conclusions

The above shows that conserved HSP70 peptides, e.g. B1 and C1 and their mammalian homologues, induce a T cell response and that the bacterially peptide primed T cells cross react with self HSP70 peptides/proteins in the mammal (mouse). Also cytokine production (IFN gamma and IL-10 production) is induced, also by the corresponding mouse homologue peptides.

Example 2

The DSS Model and the TNBS Model of Colitis

The DSS Model of Colitis

A model of colitis that is at least partially related to a change in epithelial cell barrier function is the colitis induced by the physical agent, dextran sodium sulphate (DSS). This model has been frequently used to study the efficacy of potential therapeutic agents because of its ease to induce via administration of DSS in drinking water and because DSS induces a consistent level of colitis with a defined onset. The mechanisms of inflammation in this form of colitis are, at least initially, the activation of non-lymphoid cells such as macrophages and the release of pro-inflammatory cytokines Changes in epithelial barrier function can be found early (several days before the onset of frank inflammation) and thus may set the stage for macrophage activation.

In the acute stages of DSS colitis the T cell response consists of a polarized Th1 response, but in later and more chronic phases of the inflammation, a mixed Th1/Th2 response occurs. In either case, DSS elicits the secretion of large amounts of TNF-alpha and IL-6, which are mainly responsible for the tissue damage in the disease. The protocols used were adapted from Verdu E F et al, *Clin. Exp. Immunol.* 2000, 120:46-50.

The TNBS Model of Colitis

The TNBS model of colitis can be carried out in multiple ways. One of the best and most representative variant for studying the role of the adaptive immune responses in IBD is the one used here, which is a protocol of skin sensitization followed by intracolonic instillation with TNBS (Te Velde A A. et al., *Inflamm. Bowel Dis.* 2006, 12:995-999. Our protocol was a modification (adaptation to local conditions) of the protocol described by Arita M et al. (*Proc Natl. Acad. Sci. USA.* 2005, 102:7671-6).

Example 3

Suppressive Effect of Administration of Full Length Mycobacterial HSP70 Protein on DSS Colitis in BALB/c Mice (Prague Study—1$^{st}$ Part)

This is a first part of one experiment. Due to animal number limitations the experiment was split up in two parts. In each part there were five mice per group.

Protocol

Fifteen conventional female Balb/c female mice (7 to 9 weeks old) were randomly separated in 4 groups (five mice each). To evaluate the efficacy of per oral treatment, the antigens (full length Mycobacterial HSP70 protein) were administered together with 1 mg of Soybean trypsin inhibitor (SBTI, Sigma) dissolved in 50 μl of 0.15 M sodium bicarbonate, by gavage 4 times in one week interval. After one week the mice received 3% dextran sodium sulfate (DSS) in their drinking water continuously for up to 7 days. Colitis was evaluated on day 35 by a clinical activity score, by colon length and histological score.

Figure 3A:
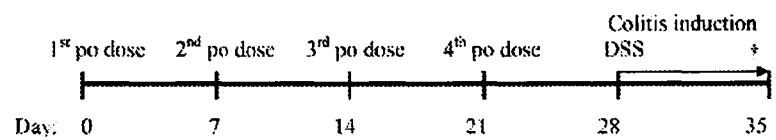
Figure 3B:
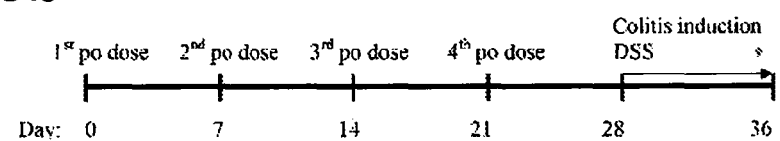

For the experiment schedule, see FIG. 3 (schedule A).

Group A1 (PBS+DSS):
  treated: 100 μl of sterile PBS/SBTI intragastrically (Control group)

Figure 4:
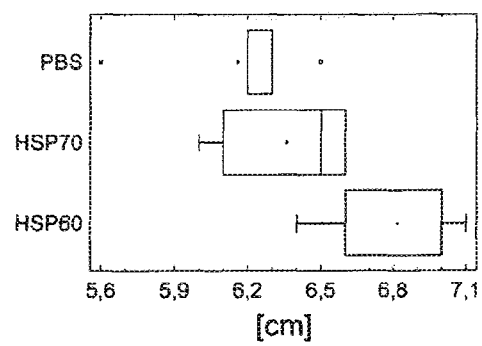
Figure 5:
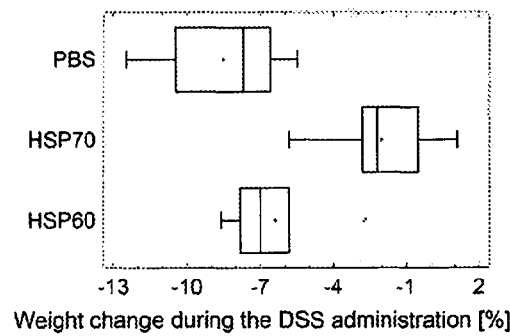
Figure 6:
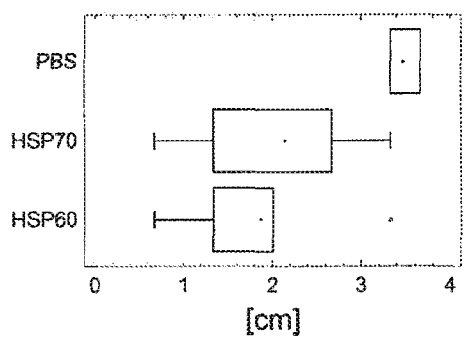
Figure 7:
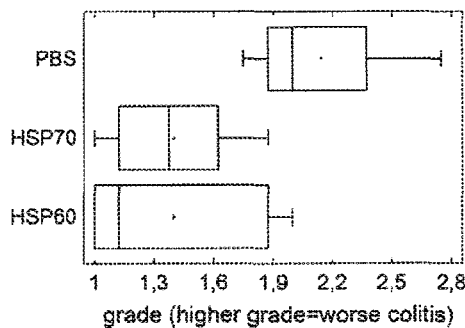

Group B1 (HSP60+DSS):
  treated: HSP60 30 μg/mouse in 100 μl of sterile PBS/SBTI (1:1) intragastrically Group C1 (HSP70+DSS):
  treated: HSP70 30 μg/mouse in 100 μl of sterile PBS/SBTI (1:1) intragastrically Results Results are shown in the tables below and in FIG. 4 (colon length), FIG. 5 (weight change), FIG. 6 (Clinical state) and FIG. 7 (histological grade).

Colon Length:
Summary Statistics

|       | Count | Average | Variance | Standard deviation | Minimum | Maximum | Range |
|-------|-------|---------|----------|--------------------|---------|---------|-------|
| PBS   | 5     | 6.16    | 0.113    | 0.336155           | 5.6     | 6.5     | 0.9   |
| HSP60 | 5     | 6.82    | 0.092    | 0.303315           | 6.4     | 6.6     | 0.6   |
| HSP70 | 5     | 6.36    | 0.083    | 0.288097           | 6.0     | 7.1     | 0.7   |
| Total | 15    | 6.45    | 0.164    | 0.405087           | 5.6     | 7.1     | 1.5   |

Multiple Range Tests

| Contrast     | Difference | P value | CI 95%                    |
|--------------|------------|---------|---------------------------|
| PBS-HSP70    | −0.2       | 0.3420  | −0.656567 to 0.256567     |
| PBS-HSP60    | *−0.66     | 0.0115  | −1.12693 to −0.193069     |
| HSP70-HSP60  | *−0.46     | 0.0394  | −0.891415 to −0.0285851   |

*denotes a statistically significant difference. ($p < 0.05$)

Weight Change
Summary Statistics

|       | Count | Average | Variance | Standard deviation | Minimum | Maximum | Range |
|-------|-------|---------|----------|--------------------|---------|---------|-------|
| PBS   | 5     | −8.56   | 8.308    | 2.88236            | −12.5   | −5.5    | 7.0   |
| HSP60 | 5     | −6.38   | 5.302    | 2.30261            | −8.6    | −2.7    | 5.9   |
| HSP70 | 5     | −2.04   | 6.743    | 2.59673            | −5.8    | 1.1     | 6.9   |
| Total | 15    | −5.66   | 13.684   | 3.69919            | −12.5   | 1.1     | 13.6  |

Multiple Range Tests

| Contrast     | Difference | P value | CI 95%                    |
|--------------|------------|---------|---------------------------|
| PBS-HSP70    | *−6.52     | 0.0056  | −10.5209 to −2.51909      |
| PBS-HSP60    | −2.18      | 0.2229  | −5.98457 to 1.62457       |
| HSP70-HSP60  | *4.34      | 0.0233  | 0.760853 to 7.91915       |

*denotes a statistically significant difference. ($p < 0.05$)

Clinical state:

| | Parameter* | Score |
|---|---|---|
| Weight loss | >5% | 0 |
| | 5-10% | 2 |
| | 10-20% | 3 |
| | >20% | 4 |
| Stool consistency | well formed pellets | 0 |
| | pasty and semiformed stools that don't stick to the anus | 2 |
| | liquid stools that did stick to the anus | 4 |
| Bleeding | no blood in hemoccult | 0 |
| | positive hemoccult (Okult viditest rapid, Vidia s.r.o.) | 2 |
| | gross bleeding | 4 |

Total score is calculated by adding the score for each parameter and divided by 3.

*Cooper et al.: Clinicopathologic study of dextran sulfate sodium experimental murine colitis. Lab Invest 69: 238-249, 1993, and Hermann et al.: Specific Type IV Phosphodiesterase Inhibitor Rolipram Mitigates Experimental Colitis in Mice JPET 292: 22-30, 2000

Summary Statistics

|       | Count | Average | Variance  | Standard deviation | Minimum | Maximum | Range |
|-------|-------|---------|-----------|--------------------|---------|---------|-------|
| PBS   | 5     | 3.4666  | 0.0334668 | 0.182939           | 3.333   | 3.667   | 0.334 |
| HSP60 | 5     | 1.8666  | 0.977422  | 0.988647           | 0.667   | 3.333   | 2.666 |
| HSP70 | 5     | 2.1334  | 1.19987   | 1.09538            | 0.667   | 3.333   | 2.666 |
| Total | 15    | 2.4889  | 1.15648   | 1.0754             | 0.667   | 3.667   | 3.0   |

Multiple Range Tests

| Contrast | Difference | P value | CI 95% |
| --- | --- | --- | --- |
| PBS-HSP70 | *1.3332 | 0.0277 | 0.187908 to 2.47849 |
| PBS-HSP60 | *1.6 | 0.0074 | 0.563121 to 2.63688 |
| HSP70-HSP60 | 0.4 | 0.6966 | −1.78852 to 1.25492 |

*denotes a statistically significant difference. ($p < 0.05$)

Histological Grade

Summary Statistics

| | Count | Average | Variance | Standard deviation | Minimum | Maximum | Range |
| --- | --- | --- | --- | --- | --- | --- | --- |
| PBS | 5 | 2.15 | 0.167187 | 0.408886 | 1.75 | 2.75 | 1.0 |
| HSP60 | 5 | 1.4 | 0.128125 | 0.357946 | 1.0 | 1.875 | 0.875 |
| HSP70 | 5 | 1.4 | 0.245312 | 0.49529 | 1.0 | 2.0 | 1.0 |
| Total | 20 | 1.65 | 0.288393 | 0.537022 | 1.0 | 2.75 | 1.75 |

Multiple Range Tests

| Contrast | Difference | P value | CI 95% |
| --- | --- | --- | --- |
| PBS-HSP70 | *0.75 | 0.0150 | 0.189576 to 1.31042 |
| PBS-HSP60 | *0.75 | 0.0311 | 0.0876491 to 1.41235 |
| HSP70-HSP60 | 0.0 | 1.0000 | −0.63021 to 0.63021 |

*denotes a statistically significant difference. ($p < 0.05$)

Conclusions

The above results show that full length HSP70 protein has a suppressive effect on colitis when administered orally, prophylactically (prior to disease induction).

Example 4

Suppressive Effect of Full Length Mycobacterial HSP70 on DSS Colitis in BALB/c Mice (Prague Study—2$^{nd}$ Part)

These results address only the second part of the experiment (see Example 3 for first part). This part has five mice per group.

Protocol

Fifteen conventional female Balb/c female mice (7 to 9 weeks old) were randomly separated in 4 groups (five mice each). To evaluate the efficacy of per oral treatment, the antigens (full length Mycobacterial HSP70 protein) were administered together with 1 mg of Soybean trypsin inhibitor (SBTI, Sigma) dissolved in 50 µl of 0.15 M sodium bicarbonate, by gavage 4 times in one week interval. After one week the mice received 3% dextran sodium sulphate (DSS) in their drinking water continuously for up to 8 days. Colitis was evaluated on day 36 by a clinical activity score, by colon length and histological score.

For the Experimental schedule, see FIG. 3, schedule B.

Groups

Group A2 (PBS+DSS):
  treated: 100 µl of sterile PBS/SBTI intragastrically (Control)

Figure 8:
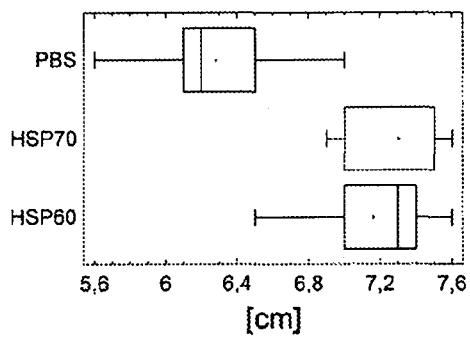
Figure 9:
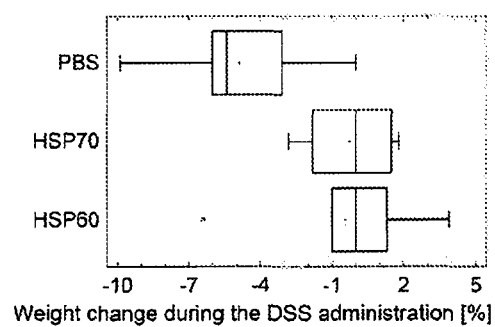
Figure 10:
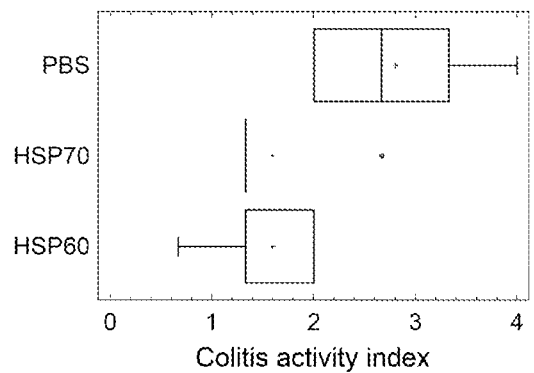
Figure 11:
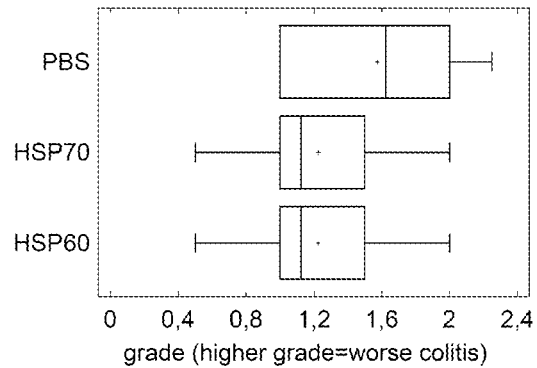

Group B2 (HSP60+DSS):
  treated: HSP60 30 µg/mouse in 100 µl of sterile PBS/SBTI (1:1) intragastrically Group C2 (HSP70+DSS):
  treated: HSP70 30 µg/mouse in 100 µl of sterile PBS/SBTI (1:1) intragastrically Results Results are shown below and in FIG. 8 (Colon length), FIG. 9 (weight change), FIG. 10 (Clinical state) and FIG. 11 (histological grade).

Colon Length:

HSP70 prevents colon shortening compared to PBS when administered perorally.

Summary Statistics

| | Count | Average | Variance | Standard deviation | Minimum | Maximum | Range |
| --- | --- | --- | --- | --- | --- | --- | --- |
| PBS | 5 | 6.28 | 0.267 | 0.51672 | 5.6 | 7.0 | 1.4 |
| HSP70 | 5 | 7.3 | 0.105 | 0.324037 | 6.9 | 7.6 | 0.7 |
| HSP60 | 5 | 7.16 | 0.183 | 0.427785 | 6.5 | 7.6 | 1.1 |
| Total | 15 | 6.91 | 0.377 | 0.613964 | 5.6 | 7.6 | 2.0 |

Multiple Range Tests

| Contrast | Difference | P value | CI 95% |
| --- | --- | --- | --- |
| PBS-HSP70 | *−1.02 | 0.00570944 | −1.649 to −0.391004 |
| PBS-HSP60 | *−0.88 | 0.0189015 | −1.5718 to −0.188197 |
| HSP70-HSP60 | 0.14 | 0.57574 | −0.693442 to 0.413442 |

*denotes a statistically significant difference. ($p < 0.05$)

Weight Change:
Summary Statistics

|  | Count | Average | Variance | Standard deviation | Minimum | Maximum | Range |
|---|---|---|---|---|---|---|---|
| PBS | 5 | −4.88 | 13.427 | 3.66429 | −9.9 | 0.0 | 9.9 |
| HSP60 | 5 | −0.26 | 4.058 | 2.01445 | −2.8 | 1.8 | 4.6 |
| HSP70 | 5 | −0.44 | 14.473 | 3.80434 | −6.4 | 3.9 | 10.3 |
| Total | 15 | −1.86 | 14.0226 | 3.74467 | −9.9 | 3.9 | 13.8 |

Multiple Range Tests

| Contrast | Difference | P value | CI 95% |
|---|---|---|---|
| PBS-HSP70 | *−4.62 | 0.0386771 | −8.9323 to −0.3077 |
| PBS-HSP60 | −4.44 | 0.0969649 | −9.88726 to 1.00726 |
| HSP70-HSP60 | 0.18 | 0.927806 | −4.61941 to 4.25941 |

*denotes a statistically significant difference. (p < 0.05)

Histological Grade:
Summary Statistics

|  | Count | Average | Variance | Standard deviation | Minimum | Maximum | Range |
|---|---|---|---|---|---|---|---|
| PBS | 5 | 1.575 | 0.325 | 0.570088 | 1.0 | 2.25 | 1.25 |
| HSP60 | 5 | 1.225 | 0.316 | 0.561805 | 0.5 | 2.0 | 1.5 |
| HSP70 | 5 | 1.225 | 0.316 | 0.561805 | 0.5 | 2.0 | 1.5 |
| Total | 15 | 1.342 | 0.302 | 0.549892 | 0.5 | 2.25 | 1.75 |

Multiple Range Tests

| Contrast | Difference | P value | CI 95% |
|---|---|---|---|
| PBS-HSP70 | 0.35 | 0.356811 | −0.475426 to 1.17543 |
| PBS-HSP60 | 0.35 | 0.356811 | −0.475426 to 1.17543 |
| HSP70-HSP60 | 0.0 | 1.0 | −0.819364 to 0.819364 |

Conclusions

Administration of Mycobacterial HSP70 protein significantly mitigates the symptoms of colitis compared to PBS (p=0.0057, 0.0387 and 0.0831 for colon length, weight loss and clinical state respectively). The results are similar to those obtained during the first part of the experiment (see Example 3).

Both Examples 3 and 4 together

Evaluation of acute dextran sodium sulphate (DSS)-induced colitis in perorally treated BALB/c mice. Values are expressed as means±standard deviations

| Experimental group | n | Colon length (cm) | Disease activity index | Histological grade |
|---|---|---|---|---|
| PBS/SBTI[a] | 10 | 6.22 ± 0.42 | 3.13 ± 0.69 | 1.86 ± 0.56 |
| HSP60/SBTI | 10 | 6.99 ± 0.39** | 1.73 ± 0.78** | 1.31 ± 0.51* |
| HSP70/SBTI | 10 | 6.83 ± 0.57* | 1.87 ± 0.88** | 1.31 ± 0.45* |

[a]Soybean trypsin inhibitor (Sigma-Aldrich), 1 mg/dose dissolved in 50 µl of 0.15 moles/litre sodium bicarbonate buffer (pH 8.0).
*Significantly different (P < 0.05) from value for control group as calculated by Student's t test.
**Significantly different (P < 0.01) from value for control group as calculated by Student's t test.

Example 5

Suppressive Effect of Full Length Mycobacterial HSP70 Protein on Induction of DSS Colitis in BALB/C Mice (Utrecht Study)

Figure 12:
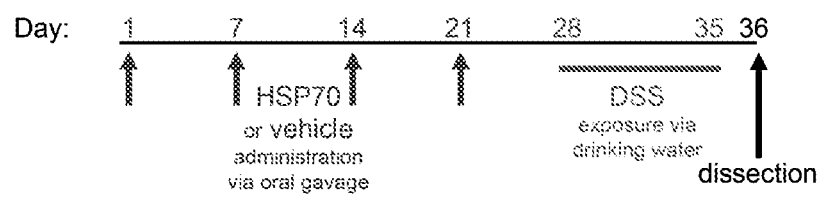

FIG. 12 shows the study setup. Vehicle refers to PBS.
Treatment:
Group A: 100 µl PBS (Control)
Group B: 30 µl Mycobacterial HSP70 protein in 100 µl PBS [SEQ ID NO: 55]

This study is performed with female BALB/c mice aged 7 weeks at the start of the experiment. Groups of mice (n=10) were treated 4 times (days 7, 9, 11, 14) with 30 µg HSP70 in 100 µl PBS (Mt hsp70; batch 031205; 2.1 Endotoxin Units/mg) or vehicle (100 µl PBS), administered via oral gavage. 10 minutes prior to gavage animals received 2 mg soybean trypsin inhibitor (SBTI) in 0.15M sodium bicarbonate, pH 8.0. Colitis was induced by administering drinking water supplemented with 3% DSS during 7 days.

Disease onset was followed by determination of body weight and stool consistency, resulting in clinical state as explained in the table below.

At dissection, colon length was recorded

Colons were cut longitudinally and divided into parts to determine:

histology on formalin-fixed paraffin sections

MPO activity in homogenates (indicative for neutrophilic infiltrations)

Ex-vivo cytokine release (TNFα, IL10) from distal colon sample.

Total score is calculated by the adding the score for each parameter and divided by 3.

Figure 13:
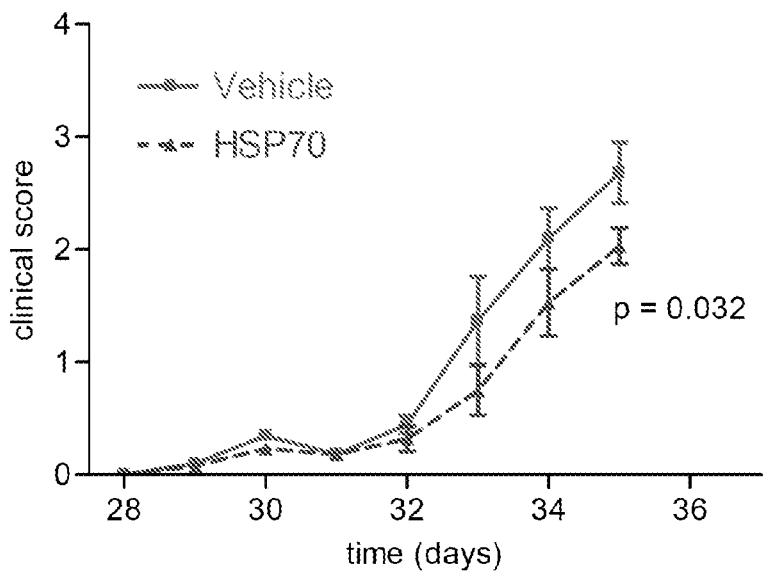

FIG. 13 shows disease progression. Pre-treatment with HSP70 protein resulted in decreased disease severity. Disease onset is based on clinical score calculated as listed above.

Determination of Clinical Score

| Parameter | | Score |
|---|---|---|
| Body weight loss | <3% | 0 |
| | 3-5% | 1 |
| | 5-10% | 2 |
| | 10-20% | 3 |
| | >20% | 4 |
| Stool consistency | Well formed pellets | 0 |
| | Easy to smear | 1 |
| | Loose stool | 2 |
| | Watery or no stool | 4 |
| Bleeding | No blood | 0 |
| | Blood within faeces | 2 |
| | Gross bleeding | 4 |

Figure 14:
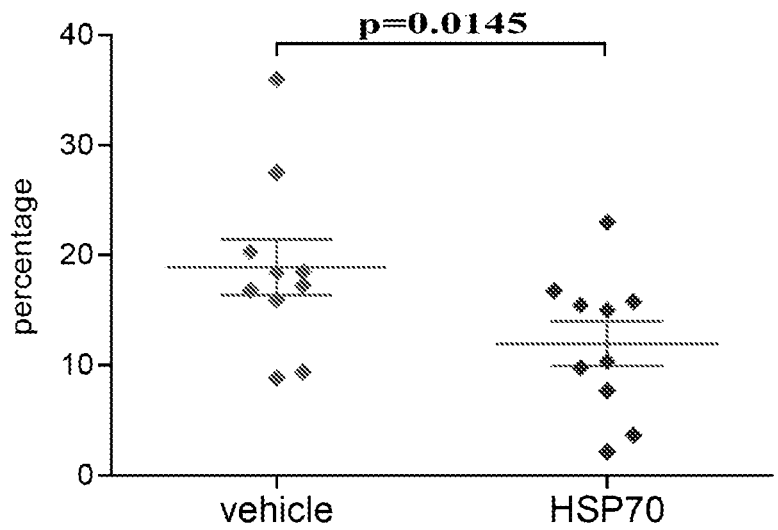

FIG. 14 shows weight loss. HSP70 treatment resulted in significantly less body weight loss due to colitis induction. Maximum body weight loss was determined on day 36.

Figure 15:
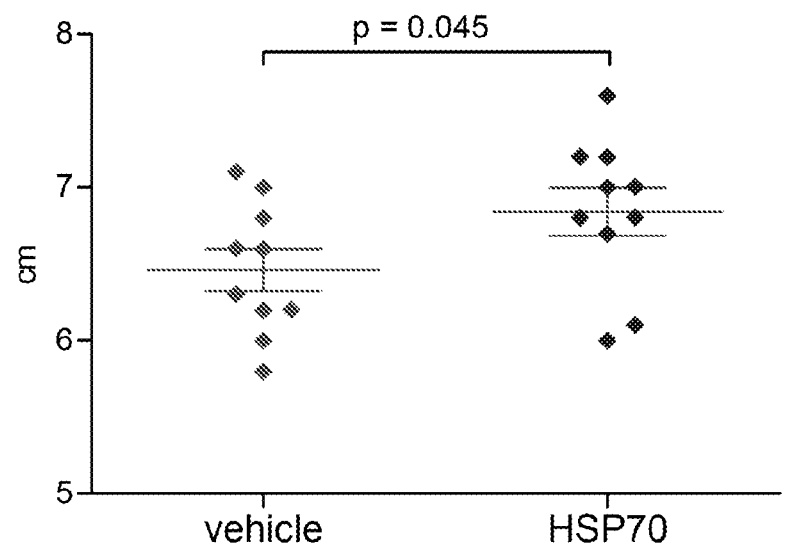

FIG. 15 shows Colon length. Colon length is less decreased upon pretreatment with HSP70 protein. Colonic inflammation normally results in reduced colon length.

Figure 16:
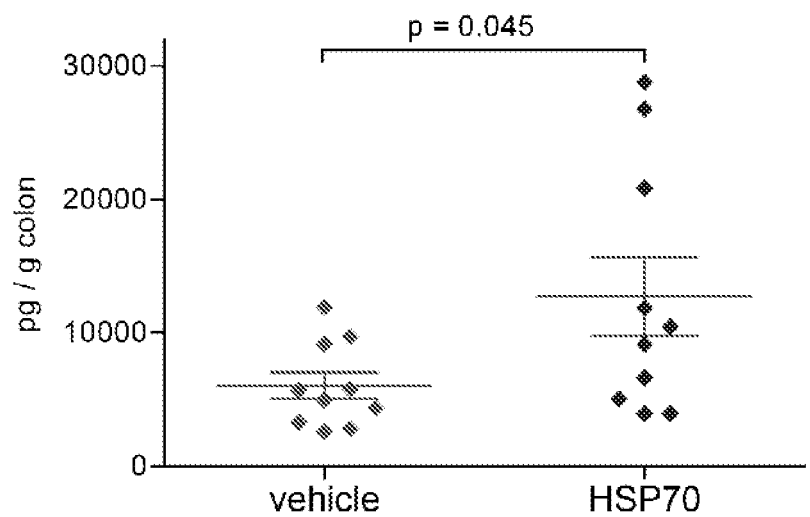

FIG. 16 shows that HSP70 treatment increased (interleukin 10) IL10 release. Distal colon samples were incubated for 24 h and IL10 content in supernatant was measured using a specific ELISA. IL10 release from distal colon sample in healthy BALB/c mice is 450±328 pg/g colon.

Summary of the Results

| | Maximum body weight loss (percentage) | | | | P value |
|---|---|---|---|---|---|
| treatment | average | st. dev | SEM (n) | day | compared to vehicle |
| Vehicle | −18.88 | 8.00 | 2.53 | 36 | |
| HSP70 | −11.94 | 6.43 | 2.03 | 36 | 0.0145 |

| | Colon Length (cm) | | | P value |
|---|---|---|---|---|
| treatment | average | st. dev | SEM (n) | compared to vehicle |
| Vehicle | 6.5 | 0.4 | 0.1 | |
| HSP70 | 6.8 | 0.5 | 0.2 | 0.0445 |

| | Colon Weight (g/6 cm) | | | P value |
|---|---|---|---|---|
| treatment | average | st. dev | SEM (n) | compared to vehicle |
| Vehicle | 186 | 18 | 6 | |
| HSP70 | 196 | 22 | 7 | 0.095 |

| | IL 10 (pg/g colon) | | | P value |
|---|---|---|---|---|
| treatment | average | st. dev | SEM (n) | compared to vehicle |
| Vehicle | 6028 | 3187 | 1008 | |
| HSP70 | 12742 | 9373 | 2964 | 0.0445 |

Statistics: Non parametric Kruskal Wallis test, followed by Mann-Whitney post-hoc test (1-tailed).

Example 6

Suppressive Effect of Full Length Mycobacterial HSP70 Protein, or Mycobacterial and Mouse HSP70 Peptide Homologues, in TNBS Colitis in BALB/C Mice Aim: to investigate if HSP70 protein or peptide pre-treatment results in attenuated TNBS-induced colitis.

Study Outline:

Female BALB/c mice (Charles River-Germany), 10-12 weeks of age at start of the experiment, were either treated intragastrically or intranasally with full HSP70 [SEQ ID NO: 55] or HSP70 peptides (Mycobacterial HSP70 derived peptide "C1" shown in SEQ ID NO: 3 and mouse homologue peptide "mC1a" of SEQ ID NO: 4) prior to disease induction. Mice received 4×30 µg HSP70 intragastrically, in a period of 4 weeks. Stomach contents were neutralized by administering soybean trypsin inhibitor (SBTI) 10 minutes prior to oral HSP70 administration.

Intranasal treatment was performed with 4×30 µg HSP70 or 4×(67 µg peptide C1 (Mycobacterial tub. HSP70 peptide 141-155, VLRIVNEPTAAALAY) mixed with 33 µg peptide mC1a (=mouse Grp75 (hspa9) peptide 216-230, VLRVINEPTAAALAY)), in a period of 1 week.

Next, mice were sensitized by painting the shaved abdomen with 1 mg of TNBS in 100 µl 50% ethanol on two consecutive days, followed by a rectal challenge with 1 mg TNBS in 100 µl 40% ethanol, after 6 days. Mice were dissected 3 days later, and colonic inflammation was determined based on colon length, weight and morphology. Furthermore, cytokine production within colon and draining caudal lymph nodes (CLN) were determined.

Treatment Groups (n=10):
A. Oral PBS, sensitization TNBS, challenge TNBS (control group)
B. Oral (full length) HSP70, sensitization TNBS, challenge TNBS (oral group)
C. Intranasal (full length) HSP70, sensitization TNBS, challenge TNBS (intranasal group)
D. Intranasal peptide, sensitization TNBS, challenge TNBS (peptide group, C1 and mC1a)

Figure 17:
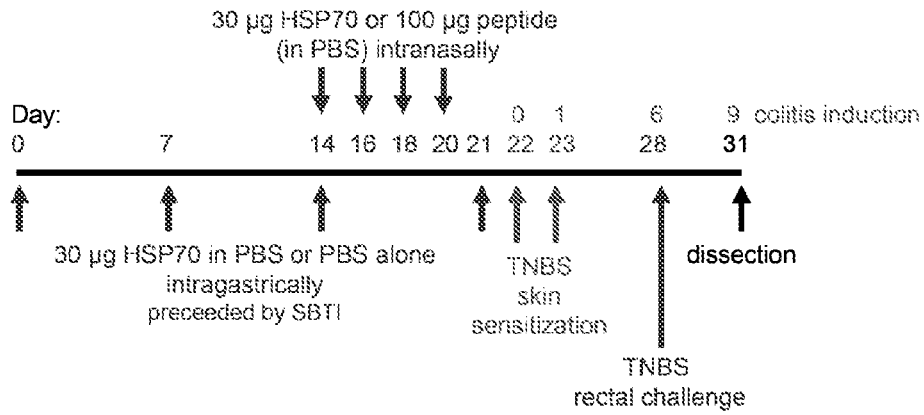

The experimental setup is shown in FIG. 17.

Results

Figure 18A:
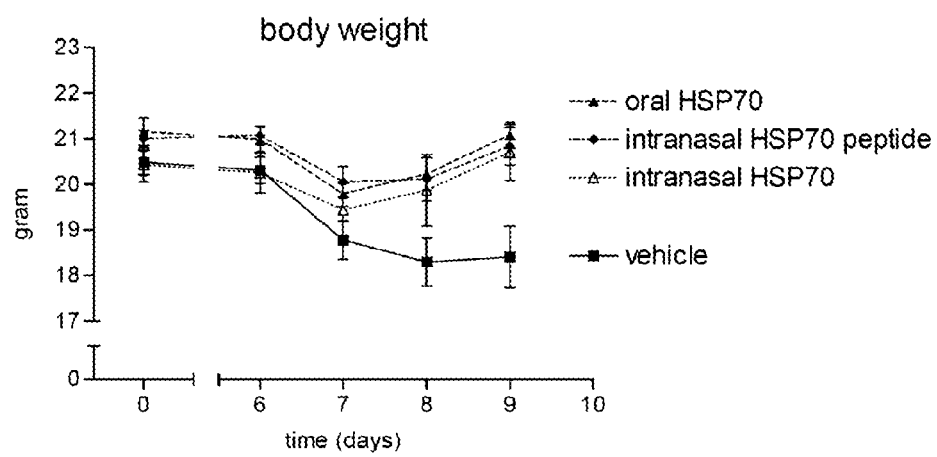
Figure 18B:
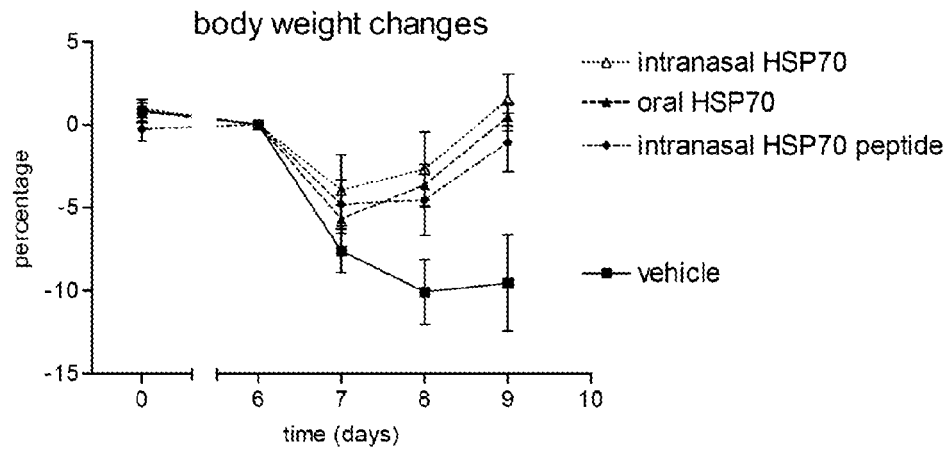
Figure 19:
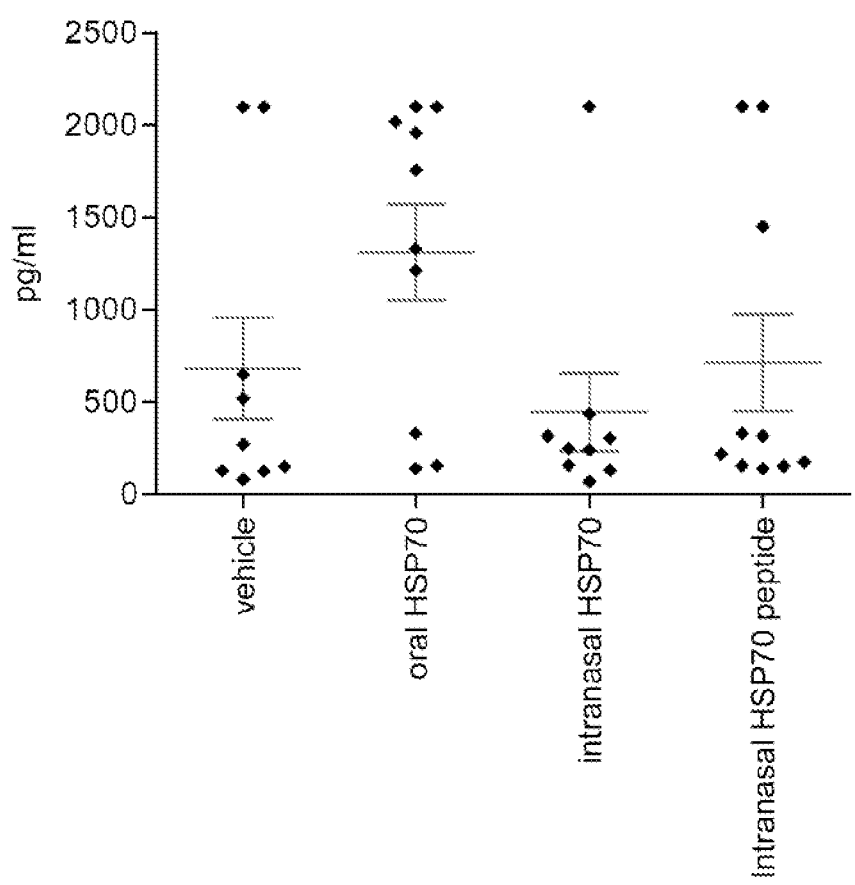

The result on body weight is shown in FIG. 18, and on IL10 production in FIG. 19.

Conclusions

The above results show that both full length HSP70 protein (either orally or intranasally given) as well as the combination of HSP70 peptides (intranasally given) have a suppressive effect on TNBS induced colitis, prophylactically (prior to disease induction). The suppressive effect of orally given full length HSP70 is associated with elevated IL-10 responses in the caudal lymphnodes.

Example 7

The Proteoglycan-induced Arthritis Model

The proteoglycan induced arthritis model (PGIA) is a murine model of rheumatoid arthritis and is described to be a T-cell dependent and antibody mediated model. In the model arthritis is induced by two times injection of human proteoglycan (hPG) in a synthetic adjuvant dimethyldioctadecylammonium (DDA), see Hanyecz A. et al., Achievement of a synergistic adjuvant effect on arthritis induction by activation of innate immunity and forcing the immune response toward the Th1 phenotype. Arthritis Rheum. 2004 50(5):1665-76.

Because arthritis is induced by immunization with a synthetic adjuvant, instead of complete Freund's adjuvant (CFA), the role of interfering immune responses, induced by microbial Hsp's present in CFA, can be excluded. Due to cross reactive responses, between the human and the mouse (self) PG, a chronic and relapsing arthritis develops. After disease development, arthritis severity is scored by clinical assessment of thickness, redness and deformation of the joints on a scale of 1-4 per paw.

Example 8

Suppressive Effect of Mycobacterial Full Length HSP70 Protein on Proteoglycan Induced Arthritis Protocol Ten female Balb/c mice, retired breeders obtained from Charles River, were randomly divided in two groups. To evaluate the effect of intra nasal treatment with Mycobacterial HSP70 (SEQ ID NO: 55) on PGIA 30 µg Hsp70 in 10 µl PBS was administered on day −7, −5 and −3 before disease induction. PGIA was induced by two times i.p. injection with 400 µg hPG and 2 mg DDA in 200 µl PBS. Subsequently developed arthritis scores were assessed by clinical evaluation as described in Example 7.

Figure 20A:
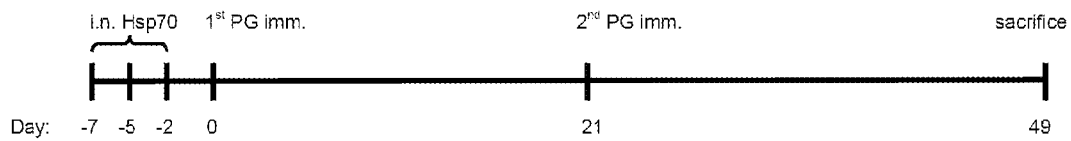
Figure 21:
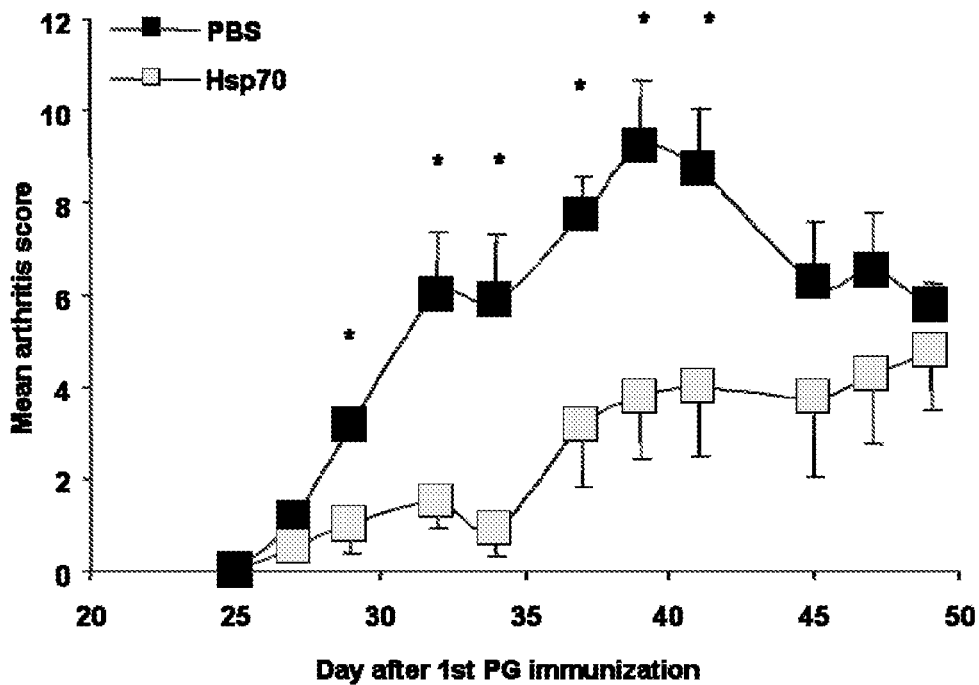

The experimental schedule is shown in FIG. 20A.
Group A: (PBS):
  Treated with 10 µl PBS intranasally (3×)
Group B (Hsp70):
  Treated with 30 µg Hsp70 in 10 µl PBS intranasally (3×)
  Results are shown in FIG. 21.
The results confirm previous studies showing that full length HSP70 can suppress arthritis development.

Example 9

Suppressive Effect of HSP70-Derived Peptides on Proteoglycan Induced Arthritis (First Experiment)

Protocol

Fifteen female Balb/c mice, retired breeders obtained from Charles River, were randomly divided in three groups (five mice per group). To evaluate the effect of intranasal treatment with Hsp70-derived peptides "B1" (SEQ ID NO: 1) and a mixture of C1 (SEQ ID NO: 3) and mC1a (SEQ ID NO: 4) (designated herein as "C1mix") on PGIA 100 µg peptide in 10 µl PBS was administered on day −7, −5 and −3 before disease induction. Ovalbumin peptide 323-339 (pOva) was used as a control peptide. PGIA was induced by two times i.p. injection with 400 µg hPG and 2 mg DDA in 200 µl PBS. Subsequently developed arthritis scores were assessed by clinical evaluation.

Figure 20B:
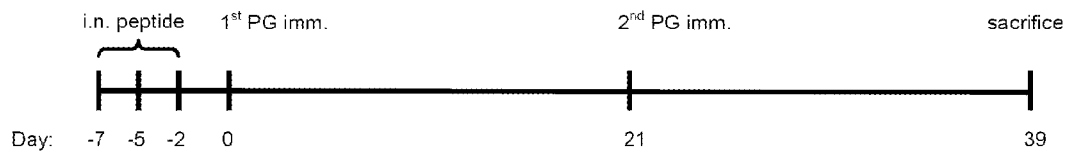
Figure 22:
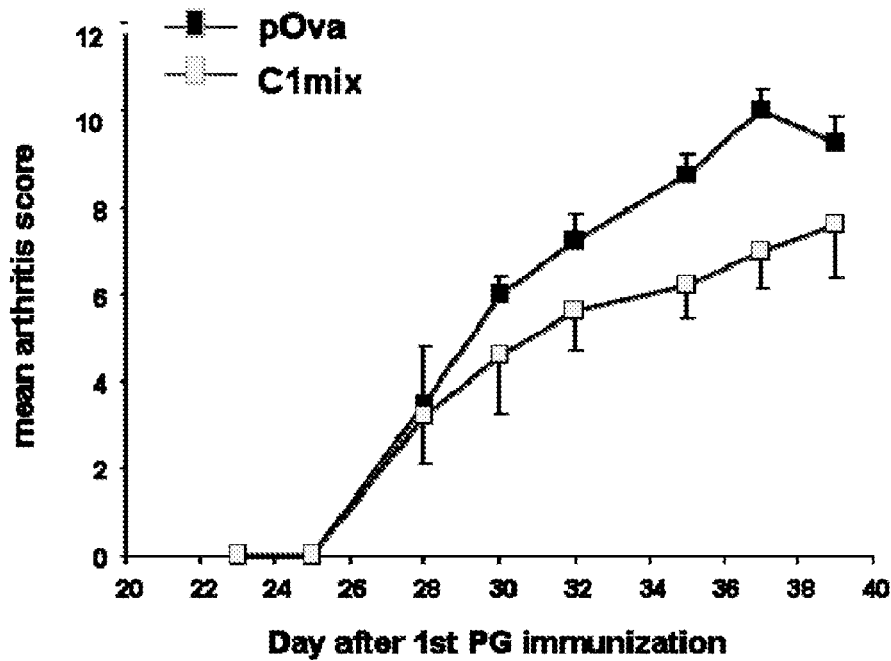
Figure 23:
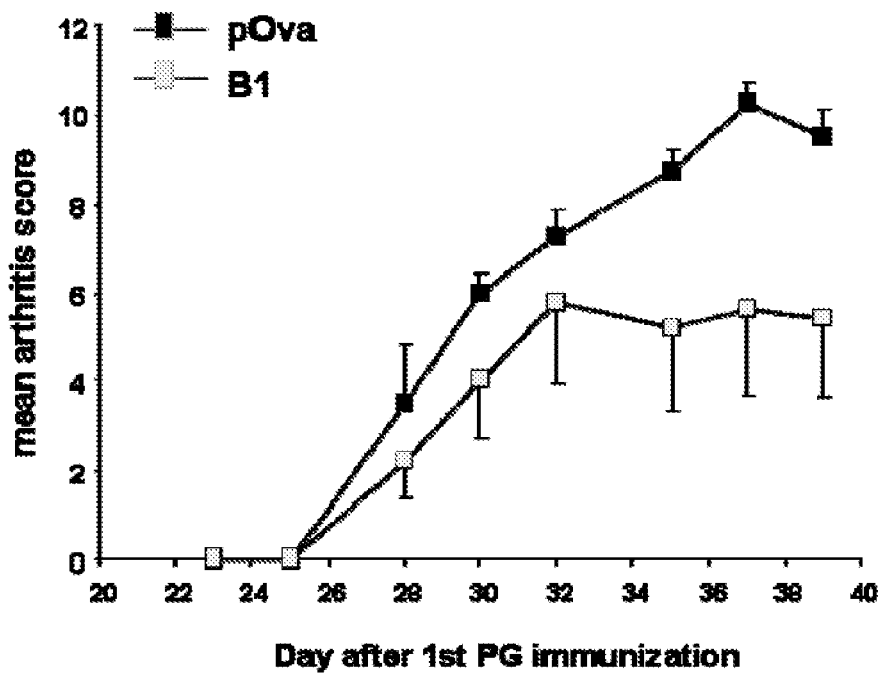
Figure 24:
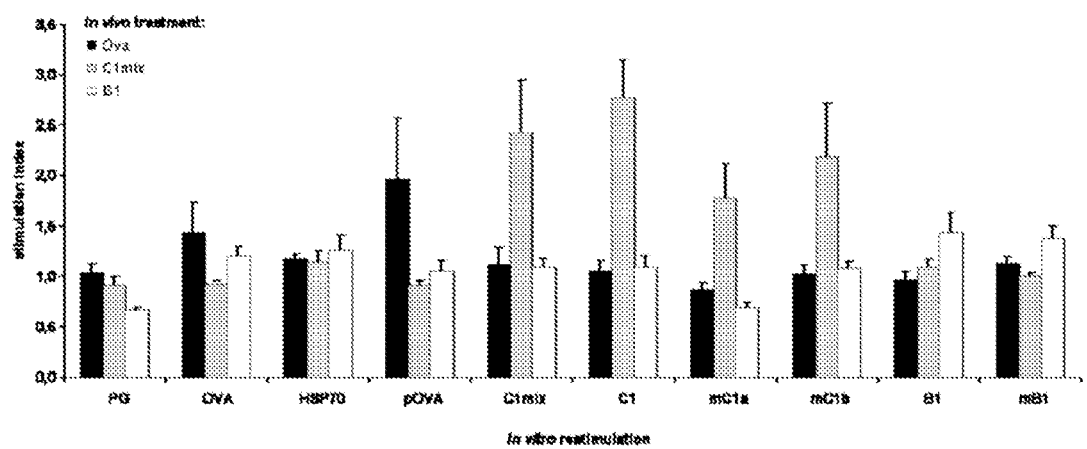

The experimental schedule is shown in FIG. 20B.
Group A: (pOva):
  Treated with 100 µg pOva in 10 µl PBS intranasally (3×)
Group B (B1):
  Treated with 100 µg B1 in 10 µl PBS intranasally (3×)
Group C(C1):
  Treated with 100 µg of a mixture of C1mix in 10 µl PBS intranasally (3×)
  Results of the arthritis scoring are shown in FIGS. 22, 23.
After sacrifice of the mice, spleen cells were isolated and in vitro restimulated for 72 hours with antigen followed by 18 hour incubation with 3H. Stimulation index (CPM antigen/CPM medium stimulated cells) was calculated and depicted per in vivo treatment group (see FIG. 24)

Figure 25:
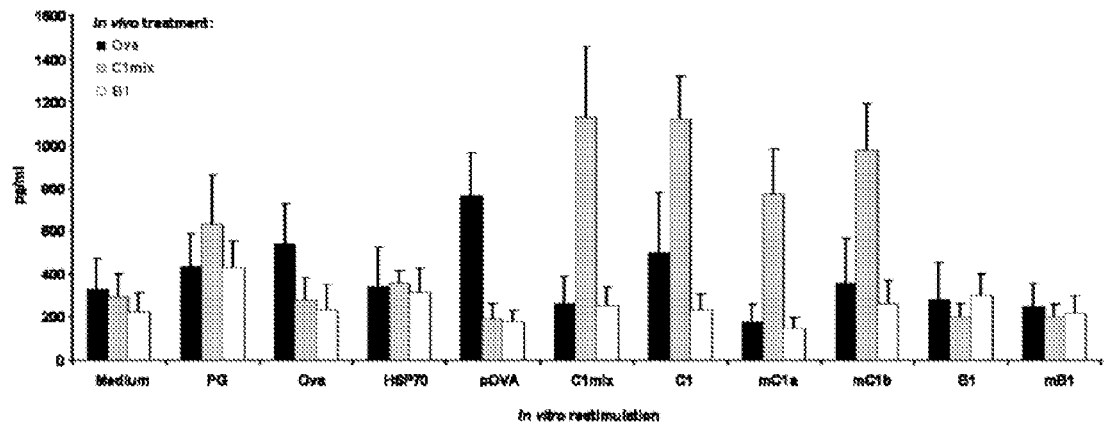
Figure 26:
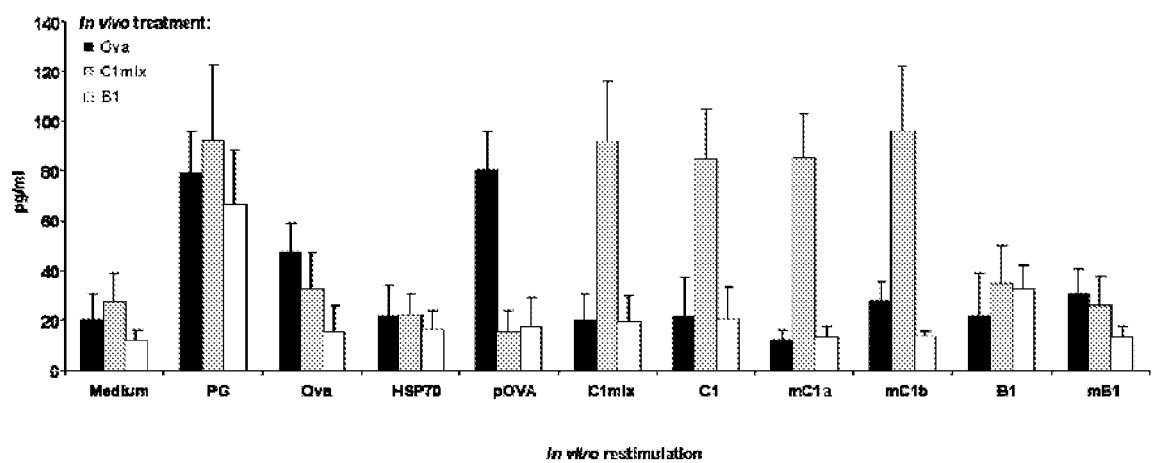

In addition to antigen specific proliferation IFN-gamma and IL10 production were measured by ELISA. Supernatants, of in vitro restimulated spleen cells, were taken after 72 hours of culture (see FIGS. 25 and 26).

The results show that treatment with both the C1mix as well as with the B1 peptide resulted in a reduction of disease severity. Intranasal administration of the peptides also induced peptide specific and cross-reactive T cell responses (proliferation, IFN gamma and IL10 production) to these peptides.

Example 10

Suppressive Effect of HSP70-Derived Peptides on Proteoglycan Induced Arthritis (Second Experiment)

Twelve female Balb/c mice, retired breeders obtained from Charles River, were randomly divided in two groups (six mice per group). To evaluate the effect of intra nasal treatment with Hsp70 derived mC1 a on PGIA 100 µg peptide in 10 µl PBS was administered on day −14, −11, −7 and −4 before disease induction. Ovalbumin peptide (pOva) was used as a control peptide. PGIA was induced by two times i.p. injection with 400 µg hPG and 2 mg DDA in 200 µl PBS. Subsequently developed arthritis scores were assessed by clinical evaluation.

Figure 20C:
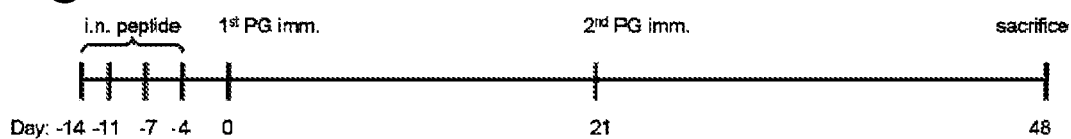
Figure 27:
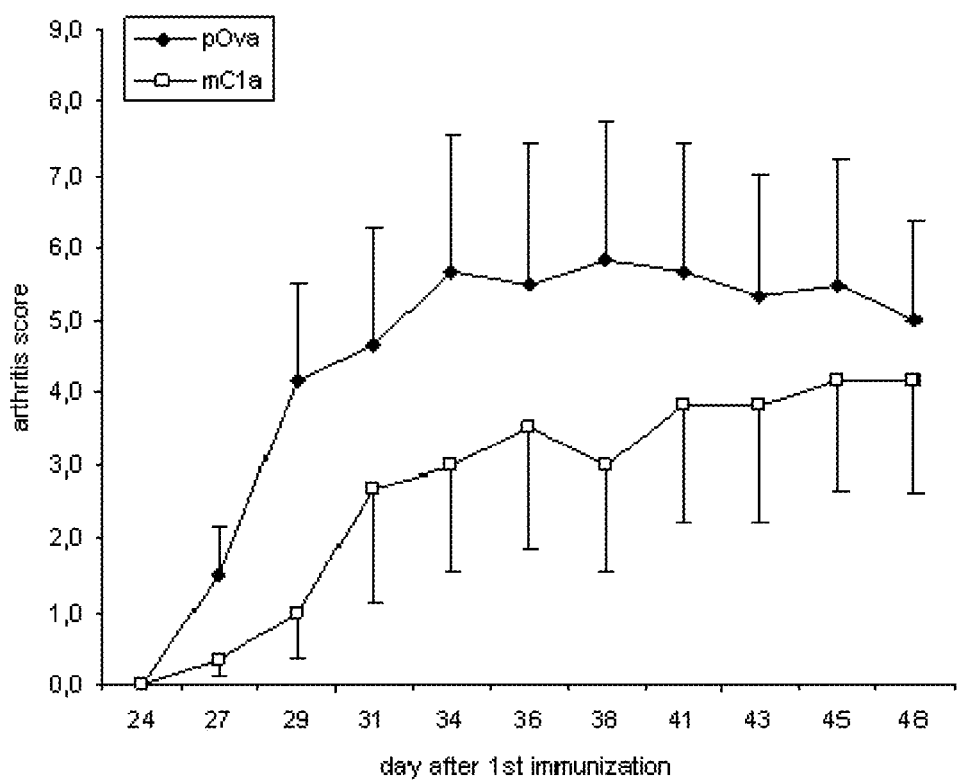

The experimental schedule is shown in FIG. 20C.
Group A: (pOva):
  Treated with 100 µg pOva in 10 µl PBS intranasally (4×)
Group B (mC1a):
  Treated with 100 µg mC1a in 10 µl PBS intranasally (4×)
  Results are shown in FIG. 27.
The results show that administration of peptide mC1a suppressed disease activity.

Example 11

Suppressive Effect of HSP70-Derived Peptides on Proteoglycan Induced Arthritis (PGIA)

Eighteen female Balb/c mice, retired breeders obtained from Charles River, were randomly divided in three groups (six mice per group). To evaluate the effect of intranasal (i.n.) treatment with Hsp70 derived peptides C1 and its mouse homologue mC1a on PGIA 100 µg peptide in 10 µl PBS was administered on day −7, −5 and −3 before disease induction (see FIG. 28). Ovalbumin peptide (pOva) was used as a control peptide. PGIA was induced by two times i.p. injection with 300 µg hPG and 2 mg DDA in 200 µl PBS. Subsequently developed arthritis scores were assessed by clinical evaluation.
Group A: (pOva): Treated with 100 µg pOva in 10 µl PBS intranasally
Group B (C1): Treated with 100 µg C1 in 10 µl PBS intranasally
Group C (mC1a): Treated with 100 µg mC1a in 10 µl PBS intranasally
  Results are shown in FIG. 29. The results show that intranasal administration of the individual peptides C1 and mC1a resulted in a significant reduction of disease activity.

Example 12

Peptide-specific Response in Human PBMC and SFMC

Peptide specific responses were studied in mononuclear cells obtained from the blood of healthy controls or the synovial fluid of a JIA and a RA patient. The patients were visiting the outpatient clinic of the departments of Rheumatology & Clinical Immunology and Pediatrics of the University Medical Center Utrecht (Utrecht, The Netherlands). The RA patient fulfilled diagnostic criteria of the American College of Rheumatology criteria for RA (ref). Cells were isolated by ficoll (Pharmacia, Uppsala, Sweden) density gradient centrifugation of heparinized blood or synovial fluid and cultured in RPMI 1640 supplemented with 2 mmol/L glutamine, 100 U/ml penicillin and streptomycin (Gibco BRL, Gaithersburg, Md. USA) and 10% AB-positive heat-inactivated human serum (Sanquin Blood Bank, Utrecht, the Netherlands) in 96 wells round bottom plates (Nunc, Roskilde, Denmark) at $2*10^5$ cells in 200 µl per well. Cultures were in triplicate stimulated with peptides at 20 µg/ml for 96 hours at 37° C. in 5% $CO_2$ with 100% relative humidity. For determination of peptide-specific proliferation of PBMC, during the last 16 hours 1 µCi (37 kBq) [$^3$H]-thymidine was added to each well and incorporation was measured. Data are expressed as stimulation index calculated as mean CPM of cells cultured with peptide divided by mean CPM of cells cultured without peptide.

Peptide-specific response of SFMC was measured by intracellular staining and FACS analysis. Therefore, cells were cultured in the presence of the peptide as described for PBMC. After 96 hours 100 µl of the medium was replaced by fresh culture medium and 40 IU/ml IL-2 was added. At day eight, cells were spun down, medium was aspirated and 200 µl new medium with fresh irradiated APC of the same donor was added ($7.5*10^5$ irradiated at 3500 rad) During 6 hours cells were cultured with or without the peptides and addition of the costimulatory mAbs CD28 and CD49 (0.5 µg/ml each) at 37° C. In the last 4 hours Golgistop (BD Biosciences) was added. Harvested cells were washed and surface stained as described previously (ref) with anti-CD3-Peridinin-chlorophyll-protein Complex (PerCP), anti-CD4-allophycocyanin (APC) and anti-CD69-fluorescein isothiocyanate (FITC) and subsequently fixed in Cytofix/cytoperm solution (BD Biosciences) followed by intracellular staining with phycoerythrin (PE) conjugated mAbs against either IL-10, IFNγ or TNFα. All antibodies were obtained from Becton Dickinson. Data are expressed as % positive cells of the $CD3^+CD4^+$ population.

Results (m)C1 Peptide Specific Responses in Human PBMC and SFMC

In humans HSP-specific T cell responses have been reported to be associated with a benign form of disease. Moreover, $CD4^+$ T cells recognizing Hsp60 have been shown in the inflamed joint. Migration of Hsp-specific T cells to the site of inflammation is probably important for their proper functioning. At the C1 region the mC1a and the mC1b peptides are completely identical to the human peptides. For that reason, the (m)C1-specific T cell response in humans was studied. First, PBMCs were isolated from healthy controls and peptide-specific proliferation was measured by [$^3$H] thymidine incorporation. Stimulation with the mC1b peptide significantly increased the proliferation compared to the A5 control peptide showing that the peptide was presented on the human HLA and could be recognized by human T cells. Next, to test if the (m)C1 peptides could be recognized, locally in the joint under inflammatory conditions, synovial fluid mononuclear cells (SFMC) were isolated and stimulated with the peptides as described in materials and methods. At day 8 new medium with peptides and fresh irradiated APC were added for additional 6 hour stimulation followed by analysis of peptide-induced production of IL-10, IFNγ, and TNFα by intracellular staining and FACS analysis. In agreement with the proliferation data obtained in healthy controls stimulation with the mC1b increased the production of IL-10, IFNγ and TNFα and surface expression of CD69 in the $CD3^+CD4^+$ population. Also, stimulation with the C1 peptide increased CD69 and cytokine expression. In contrast the control A5 as expected did not induce a peptide-specific response. In summary this showed that the C1 and especially the mC1b peptide were recognized by human T cells both in healthy controls and in the inflamed joint and thereby supporting the possibility of using the peptides in humans.

Figure 30A:
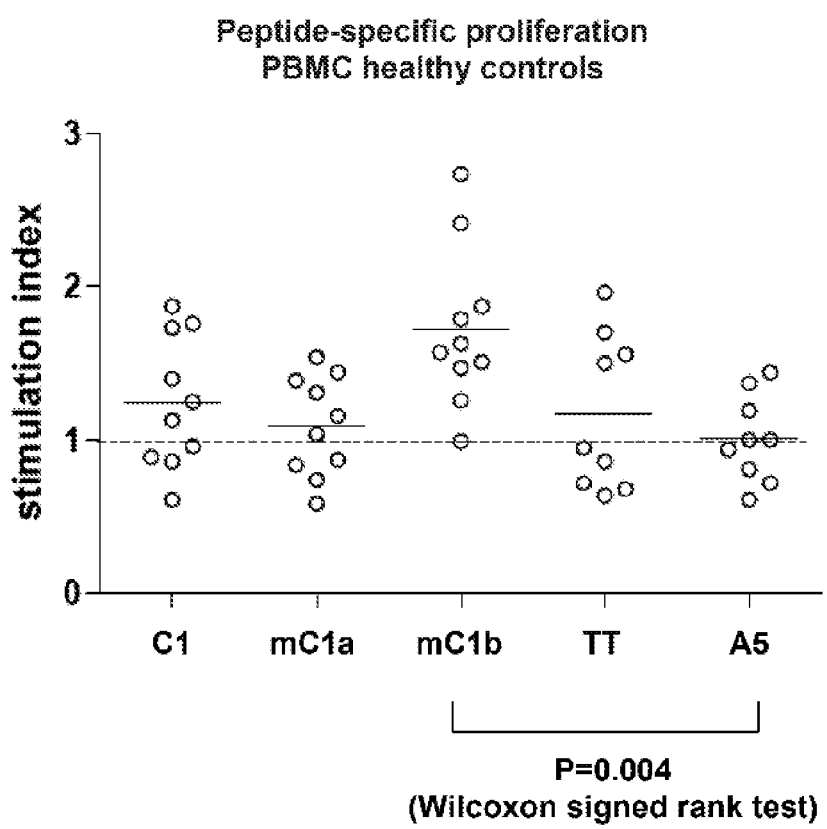
Figure 30B:
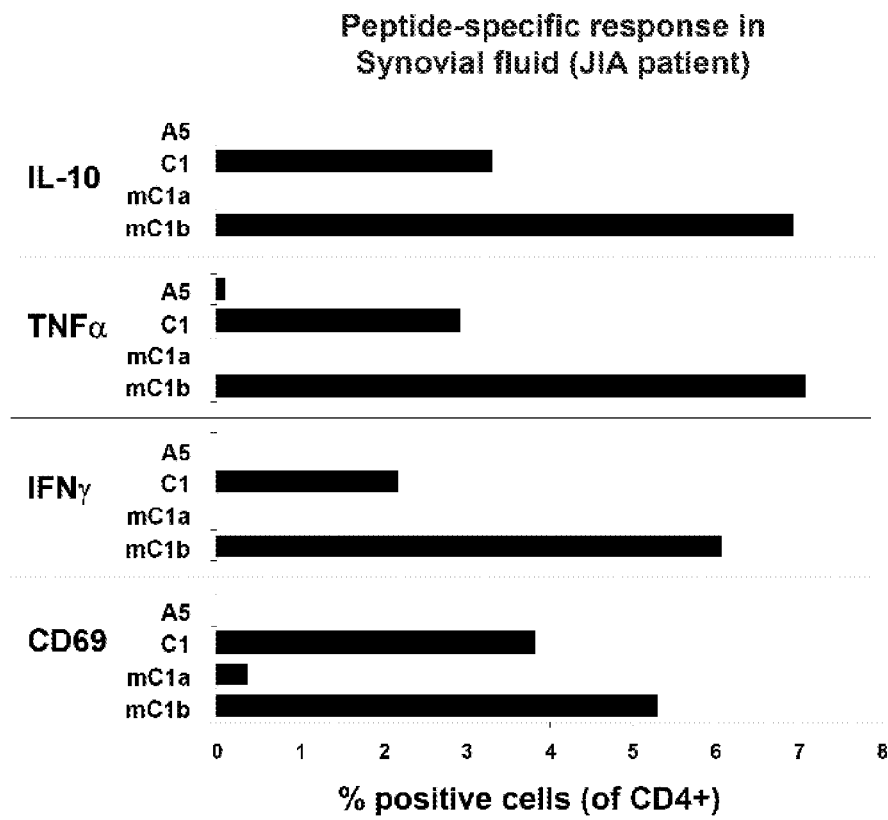

The results are presented in FIG. 30.

The invention claimed is:

1. An isolated peptide having a length from 15 to less than 19 amino acids comprising the amino acid sequence selected from the group consisting of SEQ ID NO:3 and SEQ ID NO:4.

2. A pharmaceutical composition comprising the peptide according to claim 1.

3. The peptide according to claim 1 consisting of the amino acid sequence of SEQ ID NO:3 or SEQ ID NO:4.

4. A method for the treatment of an inflammatory disease, comprising administering to a subject in need thereof an effective amount of a peptide according to claim 1.

5. The method according to claim 4, wherein the inflammatory disease is an autoimmune disease.

6. The method according to claim 5, wherein the autoimmune disease is selected from the group consisting of arthritis, atherosclerosis, multiple selerosis and myasthenia gravis.

7. The method according to claim 6, wherein the arthritis is selected from the group consisting or rheumatoid arthritis, psoriatic arthritis and juvenile arthritis.

8. The method according to claim 4, wherein the inflammatory disease is an inflammatory bowel disease.

9. The method according to claim 8, wherein the inflammatory bowel disease is selected from the group consisting of Crohn's disease, Granulomatous Colitis, Lymphocyte Colitis, Collagenous Colitis, Ulcrerative Colitis and Coeliac Disease.

10. A pharmaceutical composition comprising the peptide of claim 3.

11. A method for the treatment of an inflammatory disease, comprising administering to a subject in need thereof an effective amount of a peptide according to claim 3.

12. The method according to claim 11, wherein the inflammatory disease is an autoimmune disease.

13. The method according to claim 12, wherein the autoimmune disease is selected from the group consisting of arthritis, atherosclerosis, selerosis and myasthenia gravis.

14. The method according to claim 13, wherein the arthritis is selected from the group consisting or rheumatoid arthritis, psoriatic arthritis and juvenile arthritis.

15. The method according to claim 11, wherein the inflammatory disease is an inflammatory bowel disease.

16. The method according to claim 15, wherein the inflammatory bowl disease is selected from the group consisting of Crohn's disease, Granulomatous Colitis, Lymphocyte Colitis, Collagenous Colitis, Ulcrerative Colitis and Coeliac Disease.

* * * * *